US009169485B2

(12) United States Patent
Nunn et al.

(10) Patent No.: US 9,169,485 B2
(45) Date of Patent: Oct. 27, 2015

(54) RECOMBINANT ETHANOLOGENIC BACTERIA COMPRISING A UREASE GENE

(75) Inventors: David Nunn, Carlsbad, CA (US); Andrew MacDonald, Katy, TX (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 13/378,917

(22) PCT Filed: Jun. 23, 2010

(86) PCT No.: PCT/US2010/039586
§ 371 (c)(1),
(2), (4) Date: Feb. 17, 2012

(87) PCT Pub. No.: WO2011/005554
PCT Pub. Date: Jan. 13, 2011

(65) Prior Publication Data
US 2013/0029393 A1  Jan. 31, 2013

Related U.S. Application Data

(60) Provisional application No. 61/219,596, filed on Jun. 23, 2009.

(51) Int. Cl.
C12P 7/06 (2006.01)
C12N 1/20 (2006.01)
C12N 9/78 (2006.01)
C12N 9/88 (2006.01)
C12N 15/52 (2006.01)
C12N 9/80 (2006.01)
C12N 9/00 (2006.01)
C12P 7/10 (2006.01)

(52) U.S. Cl.
CPC  *C12N 15/52* (2013.01); *C12N 9/80* (2013.01); *C12N 9/88* (2013.01); *C12N 9/93* (2013.01); *C12P 7/10* (2013.01); *Y02E 50/16* (2013.01); *Y02E 50/17* (2013.01)

(58) Field of Classification Search
CPC ..... C12N 1/20; C12N 9/80; C12Y 305/01005
USPC .......................................... 435/252.33, 227
See application file for complete search history.

(56) References Cited

U.S. PATENT DOCUMENTS

2007/0037265 A1  2/2007  Zhou et al.
2007/0202585 A1*  8/2007  Yukawa et al. ............... 435/168

FOREIGN PATENT DOCUMENTS

WO       2007-005646 A2   1/2007
WO       2007-084477 A1   7/2007
WO  WO 2008/021141 A2 *  2/2008

OTHER PUBLICATIONS

Cussac et al., "Expression of Helicobacterpylori Urease Genes in *Escherichia coli* Grown under Nitrogen-Limiting Conditions", J. Bacteriol. 174:2466-2473, 1992.*
Wood, B. "Improving *Klebsiella oxytoca* for Ethanol Production From Lignocellulosic Biomass", Dissertation, University of Florida, 2005.*
Gao et al. "Preparation and properties of microencapsulated genetically engineered bacteria cells for oral therapy of uremia", Chinese Science Bulletin 49:1117-1121, 2004.*
"Sequence of the *Klebsiella* aerogenes Urease Genes and Evidence for Accessory Proteins Facilitating Nickel Incorporation", J. Bacteriol. 172:5837-5843, 1990.*
Liu et al., J. Bacteriol. 189:7593-7599, 2007.*
Form PCT/IB/326, WO, Jan. 12, 2012, IPRP for PCT/US2010/039586.
Supplementary European Search Report for corresponding European Application Ser. No. 10797588, Nov. 22, 2012 (10 pages).
Ohta K et al: "Meabolic Engineerng of *Kebsiella*-Oxyoca M5A1 for Ehanol Poducton fom Xylose and Glucose", Applied and Environmental Microbiology, vol. 57, No. 10, 1991, pp. 2810-2815.
Yomano L P et al: "Reengineerng *Escherchia coli* for ehanol poducton", Biotechnology Leters, Sprnger Netherlands, Dordrecht, vol. 30, No. 12, Sep. 5, 2008, pp. 2097-2103.
Ohta K et al: "Genetic Improvement of *Escherichia coli* for Ethanol Production: Chromosomal Integration of Zymomonas Mobilis Genes Encoding Pyruvate Decarboxylase and Alcohol Dehydrogenase II", Applied and Environmental Microbiollogy, American Society for Microbiology, US, vol. 57, No. 4, Apr. 1, 1991, pp. 893-900.
Zhang Xueli et al: "Poducton of Lalanine by meabolicaly engineeed *Escherchia coli*", Applied Micobiology and Biotechnology, vol. 77, No. 2, Nov. 2007, pp. 355-366.
Grabar T B et al: "Methylglyoxal Bypass Identified as Source of Chiral Contamination in 1(+) and d(−) -lactate Fermentations by Recominant *Escherichia coli*", Biotechnology Letters, Springer Netherlands, Dordrecht, vol. 28, No. 19, Jul. 26, 2006, pp. 1527-1535.
Giro F M et al: "Hemiceluloses for Fuel Ehanol: A review", Bioresoure Technoloogy, Esever BV, GB, vol. 101, No. 13, Jul. 1, 2010, pp. 4775-4800.
Form PCT/ISA/210, WO, Aug. 14, 2008, ISR for PCT/US2010/039586.
L.P.Yomamo et al., Deletion of methylglyoxal synthase gene (mgsA) increased sugar co-metabolism in ethanol—producing *Escherichia coli*. Biotechnol. Lett. May 2009, vol. 31, No. 9, pp. 1389-1398.
Brent E. Wood, et al., Development of Industrial-Medium-Required Elimination of the 2,3-Butanediol Fermentation Pathway to Maintain Ethanol Yield in an Ethanologenic Strain of *Klebsiella oxytoca*. Biotechnol. Prog. 2005, vol. 21, No. 5, pp. 1366-1372.
Montserrat Orencio-Trejo, et al., Metabolic regulation analysis of an ethanologenic *Escherichia coli* strain based on RT-PCR and enzymatic activities. Biotechnology for Biofuels. 2008, vol. 1, No. 8, pp. 1-13.

* cited by examiner

*Primary Examiner* — David J Steadman
(74) *Attorney, Agent, or Firm* — DLA Piper LLP (US)

(57) ABSTRACT

The invention provides recombinant ethanologenic bacteria, methods of making the bacteria and methods of producing ethanol using the bacteria.

12 Claims, 38 Drawing Sheets

Figure 1

CCCTTCGGCATGGCAAAACTGGTTGGCGGCATTTGCTTCTCTCTGGGGCTGATTCTTTG
TGTTGTCTGCGGAGCCGATCTCTTTACTTCCACAGTGTTGATTGTTGTTGCTAAGGCGA
GTGGGCGCATCACCTGGGGTCAGTTGGCGAAAAACTGGCTAAATGTCTATTTTGGCAAC
CTGGTCGGCGCACTGCTGTTTGTACTTTTAATGTGGCTTTCCGGCGAGTATATGACCGC
AAATGGTCAATGGGGACTAAACGTCCTACAAACCGCCGACCACAAAGTGCACCATACTT
TTATTGAGGCCGTCTGCCTTGGTATCCTGGCAAACCTGATGGTATGTCTGGCAGTATGG
ATGAGTTATTCTGGCCGTAGCCTGATGGACAAAGCGTTCATTATGGTGCTGCCGGTCGC
GATGTTTGTTGCCAGCGGTTTTGAGCACAGTATCGCAAACATGTTTATGATCCCGATGG
GTATTGTAATCCGCGACTTCGCATCTCCGGAATTCTGGACCGCTGTCGGTTCTGCACCG
GAAAATTTTTCTCACCTGACCGTGATGAACTTCATCACTGATAACCTGATTCCGGTTAC
GATCGGTAATATTATCGGCGGTGGTTTGTTGGTTGGGTTGACATACTGGGTCATTTACC
TGCGTGAAAACGATCACCATTAATGGTTGTCGAAGTACGCAGTAAATAAAAAATCCACT
TAAGAAGGTAGGTGTTACATGTCCGAGCTTAATGAAAAGTTAGCCACAGCCTGGGAAGG
TTTTACCAAAGGTGACTGGCAGAATGAAGTAAACGTCCGTGACTTCATTCAGAAAAACT
ACACTCCGTACGAGGGTGACGAGTCCTTCCTGGCTGGCGCTACTGAAGCGACCACCACC
CTGTGGGACAAAGTAATGGAAGGCGTTAAACTGGAAAACCGCACTCACGCGCCAGTTGA
CTTTGACACCGCTGTTGCTTCCACCATCACCTCTCACGACGCTGGCTACATCAACAAAG
CGTTGGAAAAGTTGTTGGTCTACAGACTGAAGCTCCGCTGAAACGTGCTCTTATCCCG
TTCGGTGGTATCAAAATGATCGAGGGTTCCTGCAAAGCGTACAACCGCGAACTGGACCC
GATGATCAAAAAAATCTTCACTGAATACCGTAAAACTCACAACCAGGGCGTGTTCGACG
TTTACACTCCGGACATCCTGCGTTGCCGTAAATCCGGTGTTCTGACCGGTCTGCCAGAT
GCTTATGGCCGTGGCCGTATCATCGGTGACTACCGTCGCGTTGCGCTGTACGGTATCGA
CTACCTGATGAAAGACAAATACGCTCAGTTCACCTCTCTGCAGGCTGATCTGGAAAACG

Figure 1 (cont'd)

```
    GCGTAAACCTGGAACAGACTATCCGTCTGCGCGAAGAAATCGCTGAACAGCACCGCGCT
    CTGGGTCAGATGAAAGAAATGGCTGCGAAATACGGCTACGACATCTCTGGTCCGGCTAC
 5  CAACGCTCAGGAAGCTATCCAGTGGACTTACTTCGGCTACCTGGCTGCTGTTAAGTCTC
    AGAACGGTGCTGCAATGTCCTTCGGTCGTACCTCCACCTTCCTGGATGTGTACATCGAA
    CGTGACCTGAAAGCTGGCAAGATCACCGAACAAGAAGCGCAGGAAATGGTTGACCACCT
    GGTCATGAAACTGCGTATGGTTCGCTTCCTGCGTACTCCGGAATACGATGAACTGTTCT
    CTGGCGACCCGATCTGGGCAACCGAATCTATCGGTGGTATGGGCCTCGACGGTCGTACC
10  CTGGTTACCAAAAACAGCTTCCGTTTCCTGAACACCCTGTACACCATGGGTCCGTCTCC
    GGAACCGAACATGACCATTCTGTGGTCTGAAAAACTGCCGCTGAACTTCAAGAAATTCG
    CCGCTAAAGTGTCCATCGACACCTCTTCTCTGCAATATGAGAACGATGACCTGATGCGT
    CCGGACTTCAACAACGATGACTACGCTATTGCTTGCTGCGTAAGCCCGATGATCGTTGG
    TAAACAAATGCAGTTCTTCGGTGCGCGTGCAAACCTGGCGAAAACCATGCTGTACGCAA
15  TCAACGGCGGCGTTGACGAAAAACTGAAAATGCAGGTTGGTCCGAAGTCTGAACCGATC
    AAAGGCGATGTCCTGAACTATGATGAAGTGATGGAGCGCATGGATCACTTCATGGACTG
    GCTGGCTAAACAGTACATCACTGCACTGAACATCATCCACTACATGCACGACAAGTACA
    GCTACGAAGCCTCTCTGATGGCGCTGCACGACCGTGACGTTATCCGCACCATGGCGTGT
    GGTATCGCTGGTCTGTCCGTTGCTGCTGACTC
20
```

Figure 2

AGCGTTCAGCGACCCGATGATCTTCGGTACTGATTTGCGCCAGTGATGCCTGGCTGGCT
GGAAAGTGGTACACAAAGGTCGGTTTTTCTTTGCCAATATTTGGCTCTACGCCAAAGGT
AAACAGCAATTGTAGCAGCGTGTCGCGGTCTTCTTCGGTATCAGCAACATTGCTCAAAT
CCAGTTTCGCTGCGACTTCCCGCAGTTGCGTTTTGTCGGCAGAGAGCGGGTCAATTTCC
AGATAACGCAAGAAAGCTTGTTGATAAGAAAGGCTTTCTGCTGCCGGGCAGTCCAGCAC
CTGTTGTAAGAGATCGTCCACCTCGTTCATCAACCGGTACATATCATAGTGCGGTCGAT
ACCACTCCAGCATAGTGAACTCAGGGTTGTGATAACGCCCCATCTCTTCATTACGGAAG
CTGCGGCACAGCTGGAATACCGGCCCACAACCGGCAACCAGCAGGCGTTTCATATGGTA
TTCCGGGCTGGTCATTAACCAGAGATTCATCCCCTGCGAATGCCCGGGGCCAACGAAAC
GTGTCTCAAACGGGACCAAATGAATATCGGTTACCGTCGCCTGGCTCATACAAGGCGTT
TCCACCTCCAGCACTCCACGATCGGCAAAGAAACGACGGATCTCCGCCATAATCGCCGC
GCGTTTTAATAAGTTAGGAATGGATGCGCTCGGCTGCCAGGATGCCGTTTCGCTCATAG
TTAAATCTCCAGTTTTTGACAAGGGCACGAAGTCTACTCGCAACGCGACGGCGAGACAA
ATTTTACGCAGGAATCAAACAGCGGTGGGCAGTGACTAAAAAAAGCACGATCTGATGGT
TTAGTAATTAAATTAATCATCTTCAGTGATAATTTAGCCCTCTTGCGCACTAAAAAAAT
CGATCTCGTCAAATTTCAGACTTATCCATCAGACTATACTGTTGTACCTATAAAGGAGC
AGTGGAATAGCGTTCGCAGACCGTAACTTTCAGGTACTTACCCTGAAGTACGTGGCTGT
GGGATAAAAACAATCTGGAGGAATGTCTCTAGATAACGCATCGCCAATGTAAATCCGGC
CCGCCTATGGCGGGCCGTTTTGTATGGAAACCAGACCCTATGTTCAAAACGACGCTCTG
CGCCTTATTAATTACCGCCTCTTGCTCCACATTTGCTGCCCCTCAACAAATCAACGATA
TTGTGCATCGCACAATTACCCCGCTTATAGAGCAACAAAAGATCCCGGGTATGGCGGTG
GCGGTAATTTATCAGGGTAAACCTTATTACTTTACCTGGGGCTATGCGGACATCGCCAA
AAAGCAGCCCGTCACACAGCAAACGTTGTTTGAGTTAGGTTCGGTCAGCAAAACATTTA

Figure 2 (cont'd)

CTGGCGTGCTTGGTGGCGACGCTATTGCTCGAGGGGAAATCAAGTTAAGCGATCCCACA
ACAAAATACTGGCCTGAACTTACCGCTAAACAGTGGAATGGGATCACACTATTACATCT
CGCAACCTACACTGCTGGCGGCCTGCCATTGCAGGTGCCGGATGAGGTGAAATCCTCAA
GCGACTTGCTGCGCTTCTATCAAAACTGGCAGCCTGCATGGGCTCCAGGAACACAACGT
CTGTATGCCAACTCCAGTATCGGTTTGTTCGGCGCACTGGCTGTGAAGCCGTCTGGTTT
GAGTTTTGAGCAGGCGATGCAAACTCGTGTCTTTCAGCCACTCAAACTCAACCATACGT
GGATTAATGTACCGCCCGCAGAAGAAAAGAATTACGCCTGGGGATATCGCGAAGGTAAG
GCAGTGCATGTTTCGCCTGGGGCGTTAGATGCTGAAGCTTATGGTGTGAAGTCGACCAT
TGAAGATATGGCCCGCTGGGTGCAAAGCAATTTAAAACCCCTTGATATCAATGAGAAAA
CGCTTCAACAAGGGATACAACTGGCACAATCTCGCTACTGGCAAACCGGCGATATGTAT
CAGGGCCTGGGCTGGGAAATGCTGGACTGGCCGGTAAATCCTGACAGCATCATTAACGG
CAGTGACAATAA

Figure 3

```
GCGTTGCCCTTACCCGCTTGCCCCTGGGTCAGCACACTCAGTCGTCCGCTGACCAGAGC
GTTCTCGAGCCCTGCCTGCCAGTTGTCGACTTTGACACCCAGTCGGCCACTCAAAGGAA
AACCTGCATACGGCCAGCTCCAGCGACCATCGCTTACGGTCAATTGTTGACGAGTAATT
TGCCACGGCAAATCGAGCAACGGATCGCCGTTATCCCGTGCCAGCACGATCAATTGCCC
GCTATTTTCCTGCCAGTCCAGCTCTGCATCCACCAGTGACGGTTCCTGCGGCAAGTTTA
ACGTCGCAGTAGCATGCCCACTTACAGGAAGTCCATCCGGCACGAGCGGCATAGTAAAT
TCCCCCACCAGTTTAACCGGCGGCTGATTTTCAAACGCGACGACATCCAGTTCGCTGAC
TGTAAGTTGTTGCCCTTTCAGCTGGCCTTGAAATTTAACTTTTTCGCCCTGATAACGCA
GTTGCTGGATATCAGAGGTTAATGCGAGAGAGTTTTCCCTGCCATTCCTGCCAGGGA
GAAAAAATCAGTTTATCGATATTGATCCAGGTGTTAGGCAGCATGGCCTGCCACTGCGC
GAGTGTTTTTGGAGCGGCTGGCGATTGCTCCGTCTGCGGCAATTTCGCCAGACAAGCAG
AATCAAGTTCTACCGTGCCGACGTTCAATAACCAGCGGCTGGGATGTGAAAGGCTGGCG
TTGGTGATATGCGCAAGCTGACAATCTCCCACCAGATAACGGAGATCGGGAATGATTAA
ACCTTTACGCGTAATGCGTGGGCTTTCATCTAATGCAATACGTGTCCCGAGCGGTAGCC
AGATGCCCGCCAGCGTGGGAACCCACAGCCCGAGCGTCATCAGCAGCGTCAACGGCACA
AGAATAATCAGTAATAACAGCGCGAGAACGGCTTTATATTTACCCAGCATGGGTAGTTA
ATATCCTGATTTAGCGAAAATTAAGCATTCAATACGGGTATTGTGGCATGTTTAACCG
TTCAGTTGAAGGTTGCGCCTACACTAAGCATAGTTGTTGATGAATTTTTCAATATCGCC
ATAGCTTTCAATTAAATTTGAAATTTTGTAAAATATTTTAGTAGCTTAAATGTGATTC
AACATCACTGGAGAAAGTCTAGATAATCTTGCCGCTCCCCTGCATTCCAGGGGAGCTGA
TTCAGATAATCCCCAATGACCTTTCATCCTCTATTCTTAAAATAGTCCTGAGTCAGAAA
CTGTAATTGAGAACCACAATGAAGAAAGTAGCCGCGTTTGTTGCGCTAAGCCTGCTGAT
GGCGGGATGTGTAAGTAATGACAAAATTGCTGTTACGCCAGAACAGCTACAGCATCATC
```

Figure 3 (cont'd)

```
GCTTTGTGCTGGAAAGCGTAAACGGTAAGCCCGTGACCAGCGATAAAAATCCGCCAGAA
ATCAGCTTTGGTGAAAAAATGATGATTTCCGGCAGCATGTGTAACCGCTTTAGCGGTGA
AGGCAAACTGTCTAATGGTGAACTGACAGCCAAAGGGCTGGCAATGACCCGTATGATGT
GCGCTAACCCGCAGCTTAATGAACTCGATAACACCATTAGCGAAATGCTGAAAGAAGGT
GCACAAGTGGATCTGACCGCGAACCAGTTAACGCTGGCGACCGCGAAACAGACATTAAC
TTATAAGCTGGCGGATTTAATGAATTAATAGCTGCCACAGCTCCCGGCGGCAAGTGACT
GTTCACTACAGCGTTTGCCGTTGGGTAATGCACACATCCCAATCGCCGTACCATCCAGT
TGACGGGCAACAGAAAGCGAACCGCCGATCATTGCACAATTTGCTTCTCCACTACTGGA
CATCGACGCTTTTAAACCTGGCGCTACGTGCGCCGCAGTCGCCTGCTGAACAGGTTCAC
TACTACACGCCGACAACAATAAAGCGGCACACCCTACCCAAAACGCTGCTCGCATCTTT
TCTTCCTCTGATCTTCAAGCCAAACGACACCGCCATAAATAATAGGCAGCACAGAGGGC
GACGTCGAGAGCTGTCCTGCGCGTTGCCCCGCATTTTTACTTTTTTATGGCTATTTTTT
TGCCCTCTGTTTGATCAAAACATTCATTACGCTGATGTGGGGACACAAAAGCGAAAAT
GCAGAAGAAAGCCATTTGCTAAAATTGAAAGATT
```

Figure 4

AGGAAATGGCCGAAACCTTTGACCCGCGAGTCTATGGTTGCCGCATTAACCTGGAACAT
CTGCGCGGCATCCTGCCTGACGGTATTTTTAAGCGTTATGGCGATGTGGCCGAACTGAA
GGCCGAAAAGATTGACGATGATTCGGCGCTGAAAGGCAAATGGGCGCTGTTTGCGAAAA
TCACCCCGACCGATGACCTTATCGCGATGAACAAGGCCGCGCAGAAGGTCTATACCTCA
ATGGAAATTCAGCCGAACTTTGCCAACACCGGCAAATGTTATCTGGTGGGGCTGGCCGT
CACCGATGACCCGGCAAGCCTCGGCACGGAATACCTGGAATTCTGCCGCACGGCAAAAC
ACAACCCCCTGAACCGCTTCAAATTAAGCCCTGAAAACCTGATTTCAGTGGCAACGCCG
GTTGAGCTGGAATTTGAAGACCTGCCTGAAACCGTGTTCACAGCCCTGACCGAAAAGGT
GAAATCCATTTTTGGCCGCAAACAGGCCAGCGATGACGCCCGTCTGAATGACGTGCATG
AAGCGGTGACCGCTGTCGCTGAGCATGTGCAGGAAAAACTGAGCGCCACTGAGCAGCGC
CTTGCTGAGATGGAAACCGCCTTTTCCGCACTTAAGCAGGATGTGACTGACAGGGCGGA
TGAAACCAGTCAGGCATTCACCCGCCTGAAAAACAGTCTCGACCACACCGAAAGTCTGA
CCCAGCAGCGCCGCAGCAAAGCCACCGGCGGTGGCGGTGACGCCCTGATGACGAACTGC
TGACCGGCGTCAGTCAGTCCGGGAAAACCTTCACGATTAACCCTTAATTTCAGGAAAAA
CTTAACCGATGACGAGTCCCGCACAGCGCACATGATGCGGGTCTCGGCAGCGATGACCG
CGCAGCGGGAAGCCGCCCCGCTGCGACATGCAACTGTCTATGAGCAGATGCTGGTTAAG
CTCGCCGCAGACCAGCGCACACTGAAAGCGATTTATTCAAAAGAGCTTAAGGCCGCGAA
AAAACGCGAACTGCTGCCGTTCTGGTTGCCGTGGGTGAACGGCGTGCTGGAGCAGGGCA
AAGGTGCACAGGATGACATTCTGATGACGGTCATGCTGTGGCGTCTGGATACCGGCGAT
ATTGCCGGTGCGCTGGAGATTGCCCGTTATGCCCTGAAGTACGGTCTGACCATGCCGGG
TAAACACCGCCGCACCCCGCCGTACATGTTCACCGAGGAGGTGGCGCTTGCGGCCATGC
GCGCCCACGCTGCCGGTGAGTCTGTGGATACCCGCCTGCTGACGGAGACCCTTGCACTG
ACCGCCACGGCAGACATGCCTGATGAAGTGCGCGCAAAGCTGCACAAAATCACCGGTCT

Figure 4 (cont'd)

```
    GTTTCTGCGTGACGCTGGTGATGCCGCCGGTGCGCTGGCTCACCTGCAACGTGCGACAC
    AGCTCGACTGTCAGGCAGGCGTCAAAAAGAGATTGAACGACTGGAGCGGGAGCTGAAA
 5  CCGAAGCCGGAGCCGCAGCCCAAAGCGGCCACCCGCGCCCTGCGTAAGACCCGGAGCGT
    GACACCGGCAAAACGTGGACGCCCGAAAAAGAAAGCCAGTTAACAACCGAATGCGCCCC
    GCGCCAGGGCGGCACGCCGGTCAGTGAGGGTGAATCACCTGACGCTGTACCGGCGTCCA
    CCGCCCGACTTTTCAGAGGTAGTCATGATGACGCTGATTATTCCGCGAACGGAGGCTCC
    CGTGTCCGGTGAGGGTACGGTGGTCATCCCGCAACCGGCAGGCGACGAGCCGGTGATTA
10  AAAACACGTTCTTTTTTCCCGATATCGACCCGAAGCGCGTCCGGGAACGTATGCGCCTT
    GAGCAGACCGTCGCCCCCGCCCGTCTGCGTGAGGCCATCAAGTCAGGCATGGCGGAGAC
    GAATGCGGAGCTGTACGAGTACCGCGAACAGAAAATTGCCGCCGGTTTTACGCGTCTGG
    CGGACGTTCCGGCGGACGACATCGACGGTGAAAGCATCAAAGTTTTTACTACGAGCGC
    GCCGTGTGTGCGATGGCGACCGCGTCGCTTTATGAGCGTTACCGCGGCGTGGATGCCAG
15  TGCGAAAGGCGACAAGAAGGCTGACAGCATTGACAGCACCATTGATGAGCTGTGGCGGG
    ATATGCGCTGGGCGGTGGCGCGTATCCAGGACAAGCCGCGCTGCATCGTGAGTCAAATC
    TGATGAAGACCTTTGCGCTACAGGGCGACACGCTCGACGCCATTTGTGTCCGGTATTAC
    GGGCGCACTGAGGGCGTGGTCGAGGCCGTGCTCGCCGCAAATCCGGGACTGGCTGAACT
    GGGTGCGGTGCTGCCACACGGCACCGCCGTCGAACTGCCCGACGTTCAGACCGCGCCCG
20  TGGCTGAAACTGTCAATCTGTGGGAGTAACGCATGACAGCAGAAGAAAAAGCGTCC
```

Figure 5

GCAGTGGGAGCACGCTTAGGCGTGTGACTGCGTACCTTTTGTATAATGGGTCAGCGACT
TATATTCTGTAGCAAGGTTAACCGAATAGGGGAGCCGAAGGGAAACCGAGTCTTAACTG
GGCGTTAAGTTGCAGGGTATAGACCCGAAACCCGGTGATCTAGCCATGGGCAGGTTGAA
GGTTGGGTAACACTAACTGGAGGACCGAACCGACTAATGTTGAAAAATTAGCGGATGAC
TTGTGGCTGGGGGTGAAAGGCCAATCAAACCGGGAGATAGCTGGTTCTCCCCGAAAGCT
ATTTAGGTAGCGCCTCGTGAAYTCATCTCCGGGGGTAGAGCACTGTTTCGGCAAGGGGG
TCATCCCGACTTACCAACCCGATGCAAACTGCGAATACCGGAGAATGTTATCACGGGAG
ACACACGGCGGGTGCTAACGTCCGTCGTGAAGAGGGAAACAACCCAGACCGCCAGCTAA
GGTCCCAAAGTCATGGTTAAGTGGGAAACGATGTGGGAAGGCCCAGACAGCCAGGATGT
TGGCTTAGAAGCAGCCATCATTTAAAGAAAGCGTAATAGCTCACTGGTCGAGTCGGCCT
GCGCGGAAGATGTAACGGGGCTAAACCATGCACCGAAGCTGCGGCAGCGACGCTTATGC
GTTGTTGGGTAGGGGAGCGTTCTGTAAGCCTGYGAAGGTGTRCTGTGAGGYATGCTGGA
GGTATCAGAAGTGCGAATGCTGACATAAGTAACGATAAAGCGGGTGAAAAGCCCGCTCG
CCGGAAGACCAAGGGTTCCTGTCCAACGTTAATCGGGGCAGGGTGAGTCGACCCCTAAG
GCGAGGCCGAAAGGCGTAGTCGATGGGAAACAGGTTAATATTCCTGTACTTGGTGTTAC
TGCGAAGGGGGACGGAGAAGGCTATGTTGGCCGGGCGACGGTTGTCCCGGTTTAAGCG
TGTAGGCTGGTTTTCCAGGCAAATCCGGAAAATCAAGGCTGAGGCGTGATGACGAGCTC
GAGAGGAGGAAAAAAAATGTCTTACACTGTTGGTACCTATCTGGCGGAACGTCTGGTT
CAAATCGGTCTGAAACATCATTTCGCGGTAGCTGGCGATTATAACCTGGTCCTGCTGGA
CAATCTGCTGCTGAATAAGAACATGGAACAAGTGTACTGTTGCAATGAGCTGAACTGTG
GCTTCTCTGCTGAGGGCTACGCGCGTGCGAAAGGCGCCGCTGCGGCTGTTGTTACCTAC
TCCGTTGGCGCACTGTCTGCATTCGATGCTATTGGTGGCGCCTATGCCGAGAACCTGCC
GGTGATCCTGATCTCCGGCGCTCCAAACAACAACGATCACGCCGCAGGCCATGTTCTGC

Figure 5 (cont'd)

ACCACGCTCTGGGCAAGACTGATTACCACTATCAGCTGGAGATGGCTAAGAACATTACC
GCAGCTGCCGAAGCAATCTACACTCCTGAAGAAGCGCCGGCAAAAATCGACCACGTAAT
TAAGACCGCCCTGCGTGAAAAGAAACCGGTGTATCTGGAGATCGCGTGTAACATCGCGT
CCATGCCGTGCGCTGCGCCGGGTCCGGCGTCCGCCCTGTTCAACGACGAAGCCTCTGAC
GAAGCATCTCTGAATGCGGCAGTAGAGGAAACTCTGAAATTCATCGCTAACCGCGATAA
AGTTGCCGTACTGGTGGGCTCTAAGCTGCGTGCTGCGGGCGCTGAAGAGGCGGCGGTGA
AATTCGCTGACGCACTGGGTGGCGCAGTCGCTACCATGGCAGCGGCAAAATCTTTCTTT
CCGGAGGAAAACCCGCACTATATCGGTACTAGCTGGGGCGAAGTTTCTTATCCTGGCGT
AGAGAAAACCATGAAGGAAGCGGATGCGGTAATCGCACTGGCGCCGGTTTTCAACGACT
ATAGCACCACCGGCTGGACCGATATCCCGGACCCGAAGAAACTGGTACTGGCCGAACCG
CGTTCTGTTGTTGTTAACGGCATCCGTTTCCCATCTGTTCATCTGAAAGACTACCTGAC
TCGTCTGGCTCAGAAGGTATCTAAGAAAACTGGTGCGCTGGACTTCTTTAAATCCCTGA
ATGCAGGCGAACTGAAGAAAGCGGCCCCAGCTGATCCGTCTGCGCCACTGGTGAACGCG
GAGATCGCTCGTCAGGTGGAGGCGCTGCTGACTCCGAACACCACTGTCATCGCCGAGAC
GGGCGACAGCTGGTTCAACGCTCAGCGCATGAAGCTGCCTAACGGTGCTCGTGTCGAGT
ACGAAATGCAGTGGGGTCATATTGGCTGGTCCGTACCGGCAGCCTTCGGCTACGCTGTA
GGTGCTCCGGAACGTCGTAACATTCTGATGGTAGGTGATGGCAGCTTCCAGCTGACTGC
TCAGGAGGTAGCTCAGATGGTACGTCTGAAACTGCCGGTAATTATCTTCCTGATCAACA
ACTACGGCTACACGATCGAGGTGATGATCCACGATGGTCCGTATAACAACATTAAAAAC
TGGGACTACGCTGGTCTGATGGAGGTATTCAATGGCAACGGCGGTTACGACTCTGGTGC
CGGCAAAGGCCTGAAGGCTAAGACCGGTGGTGAACTGGCCGAGGCTATCAAAGTTGCGC
TGGCGAACACTGATGGTCCGACCCTGATCGAGTGTTTCATCGGTCGTGAGGACTGCACC
GAAGAGCTGGTTAAATGGGGCAAGCGTGTGGCGGCTGCGAACTCCCGCAAACCGGTTAA

Figure 5 (cont'd)

CAAGCTGCTGTAAAGGAGGAAAAAAAAATGAAAGCGGCTGTGATCACCAAAGACCACAC
TATTGAAGTAAAAGATACCAAACTGCGCCCGCTGAAATATGGCGAGGCTCTGCTGGAAA
TGGAATACTGCGGTGTGTGTCATACCGATCTGCACGTTAAGAACGGTGATTTCGGCGAC
GAAACCGGCCGCATCACTGGCCACGAGGGCATTGGCATTGTGAAACAGGTCGGTGAGGG
TGTTACCTCCCTGAAGGTTGGTGACCGTGCGTCTGTTGCTTGGTTCTTCAAGGGCTGCG
GTCATTGTGAATATTGTGTCTCTGGCAACGAAACCCTGTGCCGTAACGTAGAAAACGCG
GGCTACACGGTGGATGGCGCTATGGCCGAAGAATGCATCGTCGTAGCAGACTACAGCGT
TAAGGTACCGGACGGCCTGGACCCTGCGGTTGCATCTAGCATCACGTGCGCAGGCGTTA
CCACCTATAAGGCTGTGAAAGTTTCCCAAATCCAGCCAGGCCAATGGCTGGCTATCTAC
GGCCTGGGTGGTCTGGGCAACCTGGCACTGCAATATGCTAAAAATGTTTTCAATGCGAA
AGTAATCGCAATTGACGTGAACGATGAGCAACTGGCTTTCGCGAAGGAGCTGGGTGCTG
ACATGGTAATTAACCCGAAAAACGAGGATGCTGCGAAAATCATTCAGGAAAAGTTGGC
GGTGCTCACGCAACGGTTGTTACGGCTGTTGCGAAAAGCGCCTTTAACAGCGCGGTAGA
AGCGATCCGTGCGGGTGGTCGCGTTGTTGCTGTCGGTCTGCCGCCTGAGAAGATGGACC
TGAGCATCCCTCGTCTGGTCCTGGACGGTATTGAGGTACTGGGTAGCCTGGTAGGCACG
CGTGAGGACCTGAAAGAAGCATTCCAATTTGCAGCCGAAGGTAAAGTAAAACCGAAGGT
TACTAAACGCAAGGTTGAAGAAATCAACCAGATTTTCGATGAAATGGAACACGGCAAAT
TCACTGGTCGTATGGTAGTTGATTTTACGCATCATTGAAGGAGGAAAAAAAATGGCGT
CCAGCACTTTCTACATCCCATTCGTAAACGAGATGGGTGAGGGCTCCCTGGAAAAAGCT
ATTAAAGACCTGAACGGCTCTGGCTTCAAGAACGCGCTGATCGTAAGCGACGCATTCAT
GAACAAGTCCGGTGTTGTGAAACAAGTAGCGGATCTGCTGAAGGCCCAGGGCATCAACT
CCGCTGTATACGATGGTGTAATGCCGAACCCAACCGTGACCGCCGTACTGGAGGGCCTG
AAAATCCTGAAAGACAACAACTCCGATTTCGTGATCTCCCTGGGCGGTGGTTCTCCGCA

Figure 5 (cont'd)

CGATTGTGCCAAGGCAATCGCACTGGTAGCTACTAACGGCGGTGAAGTCAAAGACTACG

AGGGCATTGACAAGTCTAAGAAACCGGCGCTGCCGCTGATGAGCATTAACACCACTGCG

GGCACTGCAAGCGAGATGACCCGTTTCTGCATCATCACCGACGAGGTGCGCCATGTAAA

AATGGCAATTGTGGACCGCCACGTAACTCCAATGGTGTCTGTGAACGATCCGCTGCTGA

TGGTAGGTATGCCGAAAGGCCTGACTGCTGCTACGGGTATGGACGCACTGACTCACGCG

TTTGAGGCCTACTCCTCTACCGCTGCGACTCCGATTACTGATGCGTGCGCGCTGAAAGC

GGCGTCCATGATTGCGAAAAACCTGAAAACCGCGTGTGATAACGGTAAAGACATGCCAG

CCCGTGAGGCGATGGCCTATGCGCAGTTCCTGGCGGGTATGGCTTTCAACAATGCCAGC

CTGGGTTACGTACACGCTATGGCTCACCAACTGGGTGGCTACTATAACCTGCCGCACGG

TGTGTGCAACGCCGTGCTGCTGCCGCATGTTCTGGCATATAACGCGTCTGTCGTGGCCG

GTCGCCTGAAGGATGTTGGTGTAGCAATGGGCCTGGACATCGCCAACCTGGGTGACAAA

GAGGGCGCTGAAGCGACGATCCAGGCGGTGCGTGACCTGGCCGCGTCTATTGGCATTCC

GGCGAACCTGACTGAACTGGGCGCGAAAAAGGAGGACGTACCTCTGCTGGCAGATCACG

CTCTGAAAGACGCATGCGCTCTGACTAACCCGCGCCAGGGTGACCAGAAAGAAGTTGAG

GAACTGTTCCTGAGCGCATTCTAATCTAGATCACACAGGAAACCATGAAGGGTGTGAAA

GAAGTAATGAAAATCTCTCTGGAAATGGACTGTACCGTGAACGGTGACAAATTCAAAAT

CACTGGTGACGGCACCGGCGAGCCGTACGAGGGTACCCAGACCCTGCATCTGACTGAAA

AAGAGGGCAAACCGCTGACCTTTTCCTTCGATGTACTGACCCCGGCATTCCAATATGGC

AACCGCACTTTCACTAAGTATCCGGGCAACATCCCGGACTTCTTCAAACAGACCGTCTC

CGGCGGTGGCTATACTTGGGAACGTAAAATGACTTACGAGGACGGCGGCATCTCTAACG

TTCGTTCCGATATCAGCGTAAAAGGTGACAGCTTCTACTATAAAATCCACTTTACCGGT

GAGTTTCCACCGCACGGCCCGGTCATGCAGCGCAAGACTGTCAAGTGGGAGCCGTCCAC

TGAAGTTATGTATGTGGATGACAAATCTGATGGCGTACTGAAAGGCGACGTTAACATGG

Figure 5 (cont'd)

```
     CGCTGCTGCTGAAAGATGGCCGCCACCTGCGCGTTGACTTCAACACCTCTTACATTCCG
     AAGAAGAAAGTAGAGAACATGCCGGACTACCATTTCATTGATCACCGTATCGAGATCCT
5    GGGTAACCCTGAAGATAAGCCGGTGAAACTGTACGAATGCGCGGTGGCCCGCTATTCTC
     TGCTGCCGGAAAAGAACAAATAATCTAGAAAAAGCCAGATTATTAATCCGGCTTTTAGA
     TCTAGCAACAAATGCCCTGCTTCCAGGAAAAGCCTCTAAGCATCAGGTAACATCAAATC
     GTACCCCAAACCGACACAGGTGGTCAGGTAGAGAATACCAAGGCGCTTGAGAGAACTCG
     GGTGAAGGAACTAGGCAAAATGGTGCCGTAACTTCGGGAGAAGGCACGCTGATATGTAG
10   GTGAGGTCCCTCGCGGATGGAGCTGAAATCAGTCGAAGATACCAGCTGGCTGCAACTGT
     TTATTAAAAACACAGCACTGTGCAAACACGAAAGTGGACGTATACGGTGTGACGCCTGC
     CCGGTGCCGGAAGGTTAATTGATGGGGTTAGCGCAAGCGAAGCTCTTGATCGAAGCCCC
     GGTAAACGGCGGCCGTAACTATAACGGTCCTAAGGTAGCGAAATTCCTTGTCGGGTAAG
     TTCCGACCTGCACGAATGGCGTAATGATGGCCAGGCTGTCTCCACCCGAGACTCAGTGA
15   AATTGAACTCGCTGTGAAGATGCAGTGTACCCGCGGCAAGACGGAAAGACCCCGTGAAC
     CTTTACTATAGCTTGACACTGAACATTGAGCCTTGATGTGTAGGATAGGTGGGAGGCTT
     TGAAGTGTGGACGCCAGTCTGCATGGAGCCGACCTTGAAATACCACCCTTTAATGTTTG
     ATGTTCTAACGTTGACCCGTAATCCGGGTTGCGGACAGTGTCTGGTGGGTAGTTTGACT
     GGGGCGGTCTCCTCCTAAAGAGTAACGGAGGAGCACGAAGGTTGGCTAATCCTGGTCGG
20   ACATCAGGAGGTTAGTGCAATGGCATAAGCCAGCTTGACTGCGAGCGTGACGGCGCGAG
     CAGGTGCGAAAGCAGGTCATAGTGATCCGGTGGTTCTGAATGGAAGGGCCATCGCTCAA
     CGGATAAAAGGTACTCCGGGGATAACAGGCTGATACCGCCCAAGAGTTCATATCGACGG
     CGGTGTTTGGCACCTCGATGTCGGCTCATCACATCCTGGGGCTGAAGTAGGTCCCAAGG

CGCCCAGAACGCCATTATGCATGACGGCAAAGCCTCAGAAGGCGATATTCAGGGCCACG

TTGATGGCTGGATCAAAGCCCACCAGCAGCAGTTCGATGGCTGGGTGAATGAGGCGCTG

GCAGCGCAGAAGTAACTCGAGCTACTACTATCTAGAGGACTCTATGCACGGCACCGTGT

TAGCACAGAATAAAAAAGGCTGGCAGGCCACGCTGGACCTCCAGTTTCAATTTCTCGGC

GGGAAAACCACGCTCGCCTCCCGTCGCCATGTCGGTCCCCTCACCGTTCAGCGCCCGTT

TTATCCCGAAGCAGAGACCTGCCACCTCTATCTGCTTCATCCGCCCGGCGGCATCGTCG

GCGGCGATGAGCTCACCATTAGCGCGACCATTGATGCCGATTGCCATACCCTGATCACC

ATGCCCGGCGCCAGCAAGTTTTATCGCAGCAGCGGCGCGCAGGCGCGGCTTCAGCAAAC

CCTGACGCTGGCCGAAAACTCGACGCTCGAGTGGCTGCCGCAGGACGCGATCTTCTTTC

CCGGCGCCAACGCCGCTTTGTCTACCGCCTTTCATCTCGCCGCCTCCAGCACGCTGCTG

GCCTGGGACCTGCTGTGCCTTGGCCGACCGGTTATCGGCGAAGCTTTTAGCCACGGCGC

GCTCGCCAATCGGCTGGAAGTGTGGGTCGACGGCTCTCCGCTGCTGATTGAGCGCCTGA

GCCTGGCCGATGGACAGCTGGCCTGCGTCGCACAGCAGCCGTGGGTGGGAACGATGCTG

TTCTACCCGGCGAACGAAACGCTGCTGGAAGGCGTACGCGAAAAGCTTACGCCGCTGGC

AAATTACGCCGGCGCTACGCTCACCGACGGCCTGCTAACGGTACGTTTTTTAAGCGATG

ATAATCTGCTTTGCCAGCGGGCGATGCGCGATATCTGGCAATTCATGCGCCCGCATCTG

ACCGGCAAATCTCCGGTACTTCCCCGAATCTGGCTGACTTAAGAGAACGCTATGGAACT

GACACCCAGAGAAAAGACAAGCTGTTGCTGTTTACCGCCGCACTGGTGGCGGAGCGTC

GCCTGGCCCGCGGCCTGAAGCTCAACTATCCCGAATCCGTGGCCCTGATTAGCGCCTTT

ATTATGGAAGGCGCGCGCGATGGCAAAAGCGTCGCCGAGCTGATGGAAGAGGGACGCCA

CGTCCTGAGCCGTGACCAGGTCATGGAAGGCGTGCCGGAAATGATCCCCGATATCCAGG

TCGAAGCCACCTTCCCGGACGGCTCGAAGCTGGTCACCGTTCATAATCCGATAATCTGA

GGTAGCGTGATGATCCCTGGAGAATATCAGATAAAGCCCGGACAGATAGCCCTCAACGC

Figure 6 (cont'd)

TGGCCGCGCAACCTGCAGCATTATTGTTGAAAATCACGGCGACCGGCCGATTCAGGTCG
GCTCGCATTACCACTTCGCCGAGGTCAACCCGGCGCTGAAGTTCGATCGCCAGCAGGCG
ACCGGCTATCGGCTGAATATCGCTGCCGGCACCGCAGTGCGCTTCGAGCCGGGTCAAAA
ACGCGAGGTGGAGCTGGTGGCGCTGGCCGGAACCCGTGCGGTGTACGGTTTTCGCGGCG
AGGTGATGGGCGCGCTGGAGGCAAACGATGAGTGAAATTTCACGTCAGGCCTATGCCGA
CATGTTCGGCCCTACCACCGGCGATAAAGTTCGCCTGGCGGACACCGAGCTATGGATCG
AGGTCGAAGATGATTTGACCACCTACGGCGAAGAGGTCAAATTTGGCGGCGGTAAAGTG
ATCCGCGACGGAATGGGGCAGGGACAGATGCTTTCCGCCGGGTGCGTGGATCTGGTGCT
GACCAACGCCCTGATCGTCGATTACTGGGGATCGTCAAAGCCGATATTGGCGTCAAAG
ACGGACGGATCTTCGCGATCGGCAAAGCCGGCAATCCGGATATTCAGCCCAACGTCACG
ATCCCGATCGGCGCGGCCACGGAAATTATTGCGGCGGAAGGTAAGATCGTCACCGCCGG
CGGCGTCGATACGCATATTCACTGGATCTGCCCGCAGCAGGCGGAAGAGGCGCTGGTCT
CCGGCGTCACCACCATGATCGGCGGCGGGACCGGCCCGGCGGCGGGCACCAACGCCACG
ACCTGTACGCCAGGGCCGTGGTATATCTCGCGGATGCTGCAGGCCGCCGACAGCCTGCC
GGTCAATATCGGCCTACTGGGTAAAGGCAACGGCTCGAATCCCGACGCGCTGCGTGAGC
AGGTCGCGGCCGGGGTTATCGGCCTGAAAATTCACGAAGACTGGGGCGCGACCCCGGCG
GCAATCGACTGCGCGCTGACCGTGGCCGACGAAATGGACGTGCAGGTCGCGCTGCACAG
CGACACCCTCAATGAGTCCGGATTCGTTGAGGATACCCTGGCGGCCATCGGCGGGCGCA
CTATCCATACTTTCCATACCGAAGGCGCGGGCGGCGGCCATGCGCCGGATATTATTACC
GCCTGCGCGCACCCCAATATTTTACCGTCGTCGACCAACCCGACGCTGCCCTATACCGT
CAACACCATTGACGAACATCTGGATATGCTGATGGTTTGCCATCACCTCGATCCGGATA
TCGCCGAGGACGTGGCGTTTGCCGAATCGCGCATTCGGCGGGAAACCATCGCCGCGGAA
GACGTCCTACACGACCTCGGCGCCTTCTCCCTTACCTCGTCAGATTCGCAGGCGATGGG

Figure 6 (cont'd)

GCGCGTCGGCGAAGTGGTGTTACGTACCTGGCAGGTAGCGCACCGGATGAAAGTTCAGC

GCGGCCCGCTGGCGGAAGAGAGCGGCGATAACGACAACTTCCGCGTAAAGCGCTATATC

GCCAAATACACGATTAATCCGGCGTTGACCCACGGTATCGCCCACGAAGTCGGCTCGAT

TGAAGCCGGTAAACTGGCGGATCTGGTGCTGTGGTCCCCGGCGTTCTTCGGCGTGAAAC

CGGCGACAATCGTTAAAGGCGGCATGATCGCCATGGCGCCGATGGGCGACATCAACGCC

TCTATCCCAACGCCGCAGCCGGTGCACTATCGCCCGATGTTCGGCGCGCTGGGCAGCGC

CCGTCACCGCTGCCGTTTGACCTTCCTGTCGCAGGCGGCGGCGGAAAACGGCGTCGCTG

AACGGCTGAACCTGCACAGCGCGACGGCGGTGGTGAAAGGCTGCCGCGAGGTACAAAAA

GCTGATATGCACCACAACGGCCTGCTGCCCAATATTACCGTGAATTCGCAAACCTACGA

GGTGCGCATCGACGGCGAACTGATTACCAGCGAACCGGCGGACGTGCTACCGATGGCGC

AACGTTATTTCCTGTTTTAAGGAGCGCACATGCTTTATTTAACCCAACGGGTGGAGACC

CCGGCGCAGGCCACGGCCAGCGTTACCCTGCCGATTGACGTGCGGGTAAAAAGCCGCAT

AAAAGTCACGCTTAACGATGGTCGTCAGGCGGGCCTGCTGCTGCCGCGCGGCCTGCTGC

TGCGCGGCGGCGATATTCTCAGCAACGAAAACGGCAGCGAGTTCATCGAAGTGATCGCC

GCCGATGAAGCCGTTTCGGTCGTACGCTGCGATGACCCCTTTGTGCTGGCGAAGGCCTG

CTATCACCTTGGCAATCGCCACGTGCCGCTGCAAATTATGCCCGGCGAGCTGCGCTATC

ATCACGATCACGTCCTGGACGATATGCTGCGCCAGTTTGGTCTGGCCGTGGATTTCGCG

CATCTGCCGTTTGAACCGGAAGCCGGCGCCTACGCCAGCGAATCACACGGCCATCACCA

TCATCACCATCATGAGCACAGCCACTAAATGCCGACGCCGGAAAAACGTCTGCGCTTAA

TGCAGCTTGCCAGCAGCAGCCTCCCGGTTGGCGGCTACAGCTGGTCCCAGGGGCTGGAG

TGGGCGGTGGAAGCGGGCTGGGTAGCGGATACCGCCGCTTTTGAGCGCTGGCAGCTGCG

GCAGATGGAGCAGAGCTTTTTTACCGTCGATCTGCCGCTGTTCGCCCGGCTTTACCGGG

CCTGCGAAGCGGGCGATCTGGCCTGCGCCCGGCGCTGGACCGCTTACCTGCTCGCCTGC

Figure 6 (cont'd)

```
CGGGAAACCCGCGAGCTGCGCGATGAAGAGCGCAACCGCGGCGCGGCCTTCACCCGGCT
GCTGGCCGACTGGCAGCCGGACTGCCCGCCCGAGTGGCGCAAGCTGTGCCAGCAAAGTC
AGCTAACCGGCATGGCGTGGCTCGGCGTACGCTGGCAAATCGCCATTCCTGACCTAGCC
CTGAGCCTTGGCTATAGCTGGATTGAAAGCGCGGTGATGGCGGGCGTCAAGCTGGTGCC
CTTTGGCCAGCAGGCGGCCCAGCAGTTGATTCTACGCCTGTGCGACCGCTACGCGGCGG
ACATGGACAGCGCCCTCGCCGCCCGGACGACGCCCTCGGTTCGGCGACGCCGCTGGCG
GCTATCGCTTCCGCCCGGCACGAAACCCAGTATTCCCGATTATTCCGTTCTTAGGAGAA
GGTATGAACATGATTAAGCAACCGCTGCGCGTCGGCGTCGGCGGCCCGGTCGGCTCCGG
AAAAACGGCGCTGCTGGAAGCCCTCTGCAAAGCCATGCGCGACACCTGGCAGCTGGCGG
TGGTGACCAACGATATCTACACCAAAGAAGATCAGCGCATTCTCACCGAAGCCGGTGCC
CTGGAGCCTGAACGAATTGTCGGTGTCGAAACCGGCGGCTGCCCGCATACCGCCATTCG
GGAAGACGCGTCAATGAACCTTGCCGCGGTGGAAGCGCTGAGCGAGAAATTCGGCAATC
TCGATCTCATCTTTGTGGAAAGCGGCGGCGATAATCTGAGCGCCACCTTCAGCCCGGAG
CTGGCGGATCTCACCATCTACGTCATCGACGTGGCGGAAGGGGAAAAAATCCCGCGCAA
AGGCGGACCGGGGATCACCAAATCCGACTTCCTGGTGATCAATAAAACCGATCTTGCAC
CGTACGTGGGCGCGTCTCTGGAAGTGATGGAGCGCGATACCCTGCGCATGCGCGGCGAA
CGCCCGTGGAGCTTCACCAACTTGAAAAGCGGCGACGGCCTGCAAAATATCATCGCCTT
TATCGAAGACAAAGGCATGCTCGGCAAGTAACCCCTGCACCATCCCGGCGCAGAGGTGT
CGGGATGGTGCATGCCCTGCCCTCTCTTTAGCCATCCCCGGATCCTTTTTATTCAGGCG
GATAAGGCGTTTTTGCCTCATCCGCCGCTCTGTACACAATGCCTGATGCGACGCTGACG
CGTCTTATCATGCCTACAAAATACACTCATTCCGTATGGCGGATAAGGCGTTTTCGCCG
CATCCGCCGTTCTGTGCACAATG
```

Figure 7

GATGACAGTACGCTGCTTTCGGGTGTTTCCGAGCTGGATGCTATTCCACCGCAGTCTCA
GGTGCTCACAGAACAACGGCTGAAGTATTGGTTTAAACTGGCTGACCCACAAACGCGAA
ATACTTTCCTGCAGTGGGCGGAAAAACAACCATCTTCCTGAGATTTTTGTGCCTGTGCG
CAGGCTTTTTCGGTCTTTATCTTGCAGCGATAAGTGCTTACAGTAATCTGTAGGAAAGT
TAACTACGGAT<u>GTACATTTATTGCACAG</u>GTGGCAAACGCCACCTGTTTCTTACGGTTTT
CTCGCCACCGGCACATCCAGATTTTTCAGTATTTCCACAAAGGGAGAGGGATTCTCTTT
GTTAAACAGTGCCCATACCCGATGGCGTGCCCGGGTCAGCGCCACGTACATTAACCGCC
GTTCTTCAGCGTCCGGGAAATCCTCAACCGGTGGCAGTAGCGCCTCTTCCATAATCGAC
TCCCGCGCCGCAGCCGGAAAACCATCACTTCCCTCCTGCAAGCCAACGATGATGACGTA
ATCCG

RECOMBINANT ETHANOLOGENIC BACTERIA COMPRISING A UREASE GENE

RELATED APPLICATION

This application is the U.S. national phase, pursuant to 35 U.S.C. §371, of international application Ser. No. PCT/US2010/039586, filed Jun. 23, 2010, designating the United States and published in English on Jan. 13, 2011 as publication WO 2011/005554 A2, which claims the benefit of U.S. provisional application Ser. No. 61/219,596, filed Jun. 23, 2009. The entire contents of which the aforementioned patent applications are hereby expressly incorporated herein by this reference.

BACKGROUND OF THE INVENTION

Lignocellulosic biomass represents a renewable source of carbohydrate for biological conversion into fuels and chemicals and, as such, presents an attractive alternative to petroleum-based technology (Arntzen and Dale, 1999). It is recognized, however, that to reach its full potential, commodity production of ethanol from biomass will require high rates and efficiencies, simple processes, and inexpensive media (Ingram et al. 1998; Zhang & Greasham 1999).

Bacteria such as *Escherichia coli* have the native ability to metabolize all sugar constituents contained in lignocellulose.

To realize fully the potential of recombinant ethanologenic bacterial strains to serve as a source of ethanol, there is a need for new and improved strains of such bacteria that can efficiently produce ethanol.

SUMMARY OF THE INVENTION

The present invention is based, at least in part, on the discovery of a new strategy for metabolic engineering of bacteria for ethanol production. In particular, the invention provides engineering strategies for the production of ethanol in urea containing media.

Accordingly in one aspect, the invention provides recombinant ethanologenic bacteria comprising a urease gene and wherein the expression of the mgsA gene is decreased as compared to expression in a reference bacterium. In one embodiment, the recombinant bacteria further comprises one of more genes naturally found in a urease operon. In one embodiment, the urease operon comprises the ureD, A, B, C, E, F and G genes and the recombinant bacteria of the invention may contain one or more of these genes. For example, the recombinant bacteria of the invention may comprise ureA, B, and C. In another embodiment of the invention, the recombinant bacteria of the invention may comprise ureA, B, and C, and one or more of ureD, E, F and G. In an exemplary embodiment, the urease genes are derived from *K. oxytoca*, e.g., *K. oxytoca* M5A1 urease operon having the sequence set forth as SEQ ID NO:6.

In another embodiment, the recombinant ethanologenic bacteria have decreased expression of mgsA, e.g., due to a deletion or mutation of the mgsA gene. In one embodiment, the resulting bacteria have the resulting mgsA sequence as set forth in SEQ ID NO:7.

In one embodiment, the recombinant bacteria further comprise ethanol production genes, e.g., heterologous ethanol production genes. In one embodiment, the ethanol production genes comprise pdc. In a related embodiment, the bacteria further comprise adhA and/or adhB. In an exemplary embodiment, the pdc, adhA and adhB genes are derived from *Zymomonas mobilis*.

In another embodiment, the recombinant bacteria have decreased expression of one or more genes in the frd operon. In one embodiment, the one or more genes in the frd operon are selected from the group comprising frdA, B, C and D genes.

In a related embodiment, the one or more genes have decreased expression due to a deletion of the genes.

In a specific embodiment, the deletion of the frdA, B, C, and D genes results in a sequence as set forth in SEQ ID NO:2.

In another embodiment, the recombinant ethanologenic bacteria comprise an inactivated or deleted ldhA gene.

In other embodiments, the bacteria are Gram-positive or Gram-negative bacteria. Exemplary Gram-negative bacteria include *Acinetobacter, Gluconobacter, Escherichia, Zymomonas, Geobacter, Shewanella, Salmonella, Shigella, Eneterobacter, Citrobacter, Erwinia, Serratia, Proteus, Hafnia, Yersinia, Morganella, Edwardsiella*, and *Klebsiella*. In a preferred embodiment, the Gram-negative bacteria is *Escherichia coli*.

Exemplary Gram-positive bacterium include *Bacillus, Clostridium, Corynebacterium, Geobacillis, Lactobacillis, Lactococcus, Oenococcus, Streptococcus* and *Eubacterium*.

In one exemplary embodiment, the *Escherichia coli* is strain KO11 (ATCC55124).

In another embodiment, the recombinant bacteria further comprises a selectable or screenable marker. In one embodiment, the screenable marker is a non-antibiotic marker, e.g., green fluorescent protein. In one embodiment, the marker can be used for quality control to insure that the recombinant bacteria of the invention contain one or more desired genes.

In another aspect, the invention provides methods for producing recombinant bacteria comprising the following steps which can be carried out in any order:

introducing pdc, adhA and/or adhB for alcohol production into the bacteria;

decreasing the expression of the frdA gene;

decreasing the expression of one or more genes in the frdABCD operon;

introducing one or more of the ureD, A, B, C, E, F, and/or G genes in the bacteria; and decreasing the expression of the mgsA gene, thereby producing recombinant bacteria.

In another aspect, the recombinant bacteria further comprise introducing a non-antibiotic screenable marker to the cell, e.g., green fluorescent protein.

In an exemplary embodiment, the ureD, A, B, C, E, F, and/or G genes are derived from *K. oxytoca*, e.g., *K. oxytoca* M5A1 which has the sequence set forth as SEQ ID NO:6.

In an exemplary embodiment, the pdc, adhA and adhB genes are derived from *Zymomonas mobilis*.

In another embodiment, the ldhA gene is inactivated or deleted.

In other embodiments, the bacteria are Gram-positive or Gram-negative bacteria. Exemplary Gram-negative bacteria include *Acinetobacter, Gluconobacter, Escherichia, Zymomonas, Geobacter, Shewanella, Salmonella, Shigella, Eneterobacter, Citrobacter, Erwinia, Serratia, Proteus, Hafnia, Yersinia, Morganella, Edwardsiella*, and *Klebsiella*. In a preferred embodiment, the Gram-negative bacteria is *Escherichia coli*.

Exemplary Gram-positive bacterium include *Bacillus, Clostridium, Corynebacterium, Geobacillis, Lactobacillis, Lactococcus, Oenococcus, Streptococcus* and *Eubacterium*.

In one aspect, the invention provides *E. coli* strain SD7 (NRRL B-50394).

The invention also provides kits comprising the recombinant bacteria of the as invention as hereinabovbe described and instructions for use.

The invention also provides methods for the production of ethanol comprising culturing the recombinant bacteria disclosed herein under conditions suitable for production of ethanol. The method may further comprise isolating the ethanol from the bacteria. In one embodiment, the ethanol production is lignocellulosic ethanol production.

BRIEF DESCRIPTION OF THE DRAWINGS

FIG. 1 sets forth the nucleotide sequence (SEQ ID NO:1) of the chromosomal region resulting from deletion of alcohol operon from E. coli KO11-RD1 and restoration of wild-type pflB gene. Underlined sequences are the regions of pflB interrupted by the insertion of the alcohol operon in E. coli KO11-RD1.

FIG. 2 sets forth the nucleotide sequence (SEQ ID NO:2) of the chromosomal region resulting from deletion of frdABCD operon. The underlined region is the site of deletion, resulting in introduction of XbaI site.

FIG. 3 sets forth the nucleotide sequence (SEQ ID NO:3) of the chromosomal region resulting from deletion of ldhA gene. The underlined region is the site of deletion, resulting in introduction of XbaI site.

FIG. 4 sets forth the nucleotide sequence (SEQ ID NO:4) of the chromosomal region resulting from deletion of Wϕ phage major capsid protein gene gpN. The underlined region is the site of deletion.

FIG. 5 sets forth the nucleotide sequence (SEQ ID NO:5) of the chromosomal region resulting from insertion of the pdc$^{Ec}$-adhA$^{Ec}$-adhB$^{Ec}$-gfp$^{Ec}$ operon into the ribosomal H operon. Underlined sequences denote the four open reading frames.

FIG. 6 sets forth the nucleotide sequence (SEQ ID NO:6) of the chromosomal region resulting from the insertion of the K. oxytoca urease operon downstream of the E. coli proVWX operon. The underlined region is the introduced sequence.

FIG. 7 sets forth the nucleotide sequence (SEQ ID NO:7) of the chromosomal region resulting from deletion of the mgsA gene. The underlined region is the site of deletion.

DETAILED DESCRIPTION OF THE INVENTION

Figure 8:
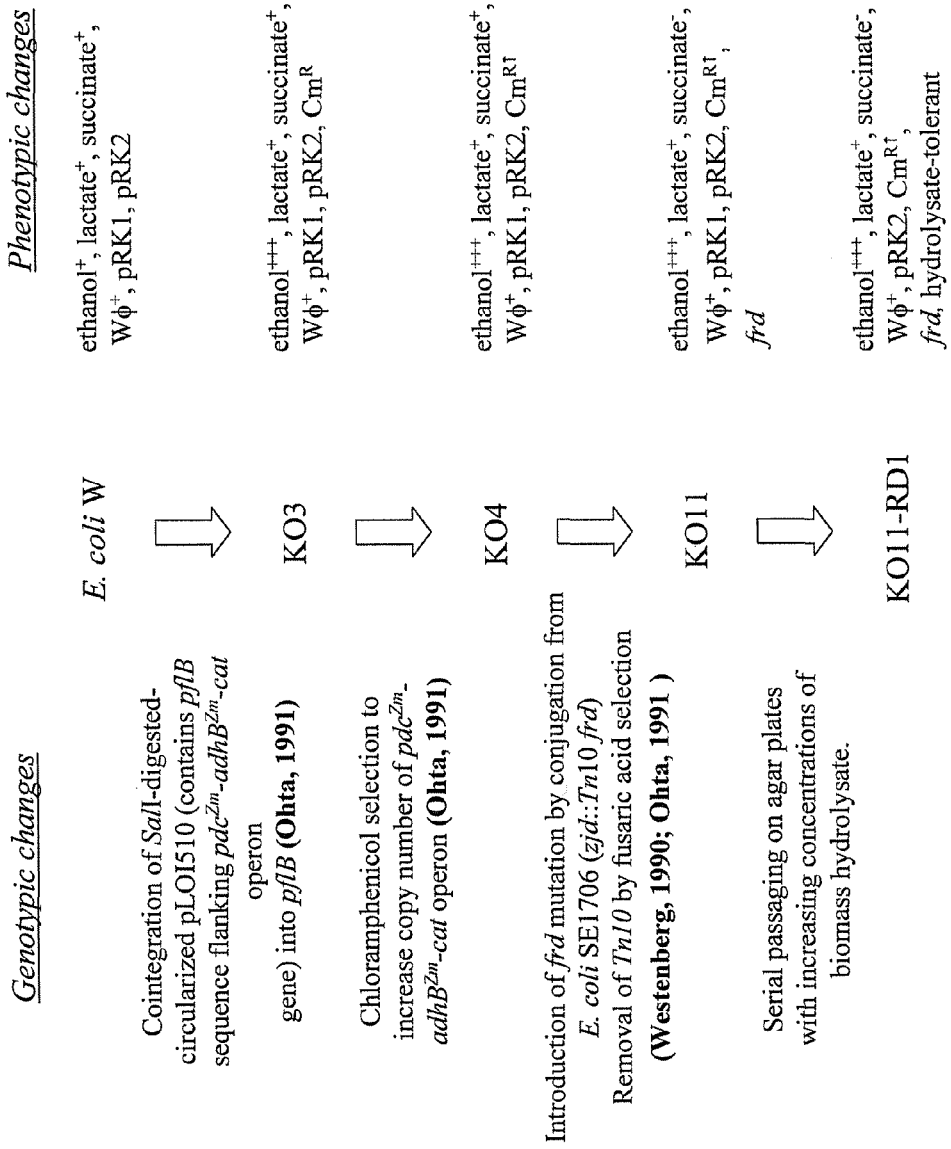
FIG. 8 depicts the lineage of E. coli KO11-RD1. Genetic changes and resultant phenotypic changes from E. coli W to E. coli KO11-RD1. Wf, ability to make viable Wf phage; pRK1, pRK2, large and small endogenous plasmids, respectively (Sobotkova, 1999); CmR, chloramphenicol-resistant.

In order for the full scope of the invention to be clearly understood, the following definitions are provided.

I. Definitions

The terms "host" and "host bacterium" are used interchangeably and are intended to include a bacterium, e.g., a naturally occurring bacterium or a recombinant bacterium, which serves as a host cell from which a recombinant bacterium of the invention is produced. Hence the recombinant bacterium of the invention is said to be "derived from" the host bacterium.

The term "derived from" as in "polynucleotide or gene derived from a bacterium" is intended to include the isolation (in whole or in part) of a polynucleotide segment from the indicated source (i.e., the bacterium) or the purification of a polypeptide from an indicated source (i.e., the bacterium). In this regard, the term is intended to include, for example, direct cloning, PCR amplification, or artificial synthesis from, or based on, a sequence associated with the indicated polynucleotide source.

As used herein the terms "recombinant bacterium," "recombinant host cell," "recombinant microorganism," and the like, are intended to include cells suitable for, or subjected to, genetic manipulation, or to incorporate heterologous polynucleotide sequences by transfection. The cell can be a microorganism or a higher eukaryotic cell. The term is intended to include progeny of the host cell originally transfected. In some embodiments, the host cell is a bacterial cell, e.g., a Gram-positive bacterial cell or a Gram-negative bacterial cell. Gram-positive bacterial host cells include, e.g., *Bacillus, Clostridium, Zymomonas, Corynebacterium, Geobacillus, Lactobacillis, Lactococcus, Oenococcus, Streptococcus* and *Eubacterium*. Gram-negative bacterial host cells include all facultatively anaerobic Gram-negative cells of the family Enterobacteriaceae such as *Escherichia, Shigella, Citrobacter, Salmonella, Klebsiella, Enterobacter, Erwinia, Kluyvera, Serratia, Cedecea, Morganella, Hafnia, Edwardsiella, Providencia, Proteus,* and *Yersinia*. Preferred recombinant hosts are *Escherichia coli* and *Klebsiella oxytoca* cells.

A "gene," as used herein, is a nucleic acid that can direct synthesis of an enzyme or other polypeptide molecule, e.g., can comprise coding sequences, for example, a contiguous open reading frame (ORF) that encodes a polypeptide, or can itself be functional in the organism. A gene in an organism can be clustered in an operon, as defined herein, wherein the operon is separated from other genes and/or operons by intergenic DNA. Individual genes contained within an operon can overlap without intergenic DNA between the individual genes. In addition, the term "gene" is intended to include a specific gene for a selected purpose. A gene can be endogenous to the host cell or can be recombinantly introduced into the host cell, e.g., as a plasmid maintained episomally or a plasmid (or fragment thereof) that is stably integrated into the genome. A heterologous gene is a gene that is introduced into a cell and is not native to the cell. In accordance with the invention, a heterologous gene also includes an endogenous gene that is introduced into the cell at a location other than its natural location in the genome of the cell.

The term "heterologous ethanol production gene" is intended to include a gene or portion thereof that is derived from any source, e.g., eukaryotes, prokaryotes, archaea, virii, or synthetic nucleic acid fragments, that encodes a polypeptide involved in the production of ethanol as a primary fermentation production, and that is incorporated into a host cell to which the gene is not native. The term "heterologous ethanol fermentation gene" also refers to a gene that encodes a polypeptide involved in the fermentation of a carbohydrate, for example in a metabolic pathway of an organism that produces ethanol as the primary fermentation produced by an organism, that is not naturally occurring in an organism, e.g., a gene that is introduced into the organism. The terms "heterologous ethanol production gene" and "heterologous ethanol fermentation gene" may be used interchangeably and are intended to include a gene that is involved in at least one step in the bioconversion of a carbohydrate to ethanol. Accordingly, the term is intended to include any gene encoding a polypeptide such as an alcohol dehydrogenase, a pyruvate decarboxylase, a secretory protein/s, or a polysaccharase e.g., a glucanase, such as an endoglucanase or exoglucanase, a cellobiohydrolase, β-glucosidase, endo-1,4-β-xylanase, β-xylosidase, α-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, or pectate lyase.

The phrase "ethanol production genes" is meant to include substantially all the genes that have evolved in an ethanologenic organism, from which the heterologous ethanol production genes are obtained/derived, that comprise the organism's natural ethanol production pathway. For example, the ethanol production genes of *Zymomonas mobilis*, an ethanologenic bacterium, includes the pdc, adhA and adhB genes. The ethanol production genes of *Saccharomyces cerevisiae*, an ethanologenic yeast, includes four or five different adh genes, for example alcohol dehydrogenase I, II, III and IV (adh I-IV) (Drewke et al. 1988; Reid et al. 1994), and 2 different pdc genes. In accordance with an embodiment of the invention, the recombinant *E. coli* KO11 (ATCC 55124) (Ohta et al. 1991) can be used as a host cell.

The terms "inactivated" or "inactivate" are intended to include any means by which a gene is stopped from encoding its intended polypeptide or from encoding an active form of its intended polypeptide. Accordingly, the terms include, for example, mutation, deletion, insertion, duplication, missense, frameshift, repeat, nonsense mutation, or other alteration or modification such that gene activity (i.e. transcription) is blocked. For example, in accordance with one embodiment of the invention, one or more genes encoding polypeptides that interfere with or otherwise reduce the amount of ethanol produced by the ethanol production genes are inactivated by deletion.

As used herein, "decreasing" or "decreases" or "decreased" refers to decreasing by at least 5%, for example, 5, 6, 7, 8, 9, 10, 15, 20, 25, 30, 35, 40, 45, 50, 55, 60, 65, 70, 75, 80, 85, 90, 95, 99 or 100%, for example, as compared to the decreased level of expression of the msgA gene in a bacterium, as compared to a reference bacterium. The terms also refer to, for example, decreased expression of one or more genes in the frd operon or decreased expression of the ldhA gene, as compared to a reference bacterium.

As used herein, "decreasing" or "decreases" or "decreased" also means decreases by at least 1-fold, for example, 1, 2, 3, 4, 5, 6, 7, 8, 9, 10, 15, 20, 30, 40, 50, 60, 70, 80, 90, 100, 200, 500, 1000-fold or more, for example, as compared to the level of expression of the msgA gene in a bacterium, as compared to a reference bacterium. The terms also refer to, for example, decreased expression of one or more genes in the frd operon or decreased expression of the ldhA gene, as compared to a reference bacterium.

"Decreased" or "reduced" also means eliminated such that there is no detectable level of activity, expression, etc., for example no detectable level of expression of the msgA gene, one or more genes in the frd operon, or the ldhA gene.

As used herein, "activity" refers to the activity of a gene, for example the level of transcription of a gene. "Activity" also refers to the activity of an mRNA, for example, the level of translation of an mRNA. "Activity" also refers to the activity of a protein, for example MsgA.

As used herein, "expression" as in "expression of MsgA" refers to the expression of the protein product of the msgA gene. As used herein, "expression" as in "expression of msgA" also refers to the expression of detectable levels of the mRNA transcript corresponding to the msgA gene. As used herein, "expression" as in "expression of ldhA" also refers to the expression of detectable levels of the mRNA transcript corresponding to the ldhA gene.

"Altering", as it refers to expression levels, means decreasing expression of a gene, mRNA or protein of interest, for example the msgA gene or the ldhA gene.

As used herein, "not expressed" means there are no detectable levels of the product of a gene or mRNA of interest, for example, msgA or ldhA mRNA.

As used herein "eliminate" means decrease to a level that is undetectable.

The term "pyruvate decarboxylase" (pdc) is intended to include the enzyme that serves to direct the flow of pyruvate into ethanol during fermentation. By convention, the term "pdc" refers to a pyruvate decarboxylase gene whereas the term "PDC" refers to a pdc gene product, i.e., a pyruvate decarboxylase polypeptide or enzyme. An exemplary pdc sequence is the *Z. mobilis* pdc described by Conway et al. (J. Bacteriol. 169 (3), 949-954 (1987)) and set forth as GenBank accession number AAA27696.

The terms "alcohol dehydrogenase A" (adhA) and "alcohol dehydrogenase B" (adhB) and "alcohol dehydrogenase E" (adhE) are intended to include the enzymes that convert acetaldehyde to ethanol under fermentative conditions. By convention, the term "adhA," "adhB" or "adhE" refers to an alcohol dehydrogenase gene whereas the term "ADHA," "ADHB" or "ADHE" refers to an "adhA," "adhB" or "adhE" gene product, respectively, i.e., an alcohol dehydrogenase polypeptide or enzyme. An exemplary adhA sequence is the *Z. mobilis* adhA described by Keshav et al. (J. Bacteriol. 172 (5), 2491-2497 (1990)) and set forth as GenBank accession number AAA27682. An exemplary adhB sequence is the *Z. mobilis* adhB described by Conway et al. (J. Bacteriol. 169 (6), 2591-2597 (1987)) and set forth as GenBank accession number AAA27683. An exemplary adhE sequence is the *E. coli* adhE described by Kessler et al. (FEBS Lett. 281 (1-2), 59-63 (1991)) and set forth as GenBank accession number CAA41955.

The term "lactate dehydrogenase" (ldhA) is intended to include the enzyme that converts pyruvate to lactate under fermentative conditions. By convention, the term "ldhA" refers to a lactate dehydrogenase gene whereas the term "LDHA" refers to an ldhA gene product, i.e., a lactate dehydrogenase polypeptide or enzyme. An exemplary ldhA sequence is the *E. coli* K-12 ldhA described by Riley et al. (Nucleic Acids Res. 34 (1), 1-9 (2006)) and set forth as GenBank accession number NP_415898.

The term "acetate kinase" (ackA) is intended to include the enzyme that encodes an alternative route for pyruvate metabolism. By convention, the term "ackA" refers to an acetate kinase gene whereas the term "ACKA" refers to an ackA gene product, i.e., an acetate kinase polypeptide or enzyme. An exemplary ackA sequence is the *E. coli* K-12 ackA described by Riley et al. (Nucleic Acids Res. 34 (1), 1-9 (2006)) and set forth as GenBank accession number NP_416799.

The term "frd operon" is intended to include the four subunits that comprise the fumarate reductase complex (A-D). By convention, the term "frd operon" refers to the genes which encode the four subunits, whereas the term "FRD OPERON" refers to the proteins which encode the four subunits. An exemplary fumarate reductase A sequence is the *E. coli* K-12 fumarate reductase A described by Riley et al. (Nucleic Acids Res. 34 (1), 1-9 (2006)) and set forth as GenBank accession number NP_418578. An exemplary fumarate reductase B sequence is the *E. coli* K-12 fumarate reductase B described by Riley et al. (Nucleic Acids Res. 34 (1), 1-9 (2006)) and set forth as GenBank accession number NP_418577. An exemplary fumarate reductase C sequence is the *E. coli* K-12 fumarate reductase C described by Blattner et al. (Nucleic Acids Res. 34 (1), 1-9 (2006)) and set forth as GenBank accession number NP_418576. An exemplary fumarate reductase D sequence is the *E. coli* K-12 fumarate reductase D described by Riley et al. (Nucleic Acids Res. 34 (1), 1-9 (2006)) and set forth as GenBank accession number NP_418575.

The term "cas AB" (casAB) is intended to include the enzymes Enzyme II cellobiose and phospho-beta-glucosidase that ferment cellubiose. By convention, the term "casAB" refers to the casAB genes whereas the term "CASAB" refers to the casAB gene product, i.e., a casAB enzyme. Exemplary casA and casB sequences are the *K. oxytoca* casA (cellobiose-specific PTS permease) described by Lai et al. (Appl. Environ. Microbiol. 63 (2), 355-363 (1997)) and set forth as GenBank accession number AAB51563 and the *K. oxytoca* casB (phospho-cellobiase) described by Lai et al (Appl. Environ. Microbiol. 63 (2), 355-363 (1997)) and set forth as GenBank accession number AAB51564. In certain embodiments, the casAB genes are from *Klebsiella oxytoca*.

The term "methylglyoxal synthaseA" (mgsA) is intended to include the enzyme that encodes the enzyme mgsA in the first step of the methylglyoxal bypass pathway. By convention, the term "mgsA" refers to a methylglyoxal synthase gene whereas the term "MGSA" refers to an mgsA gene product, i.e., a methylglyoxal synthaseA polypeptide or enzyme. An exemplary mgs sequence is the *E. coli* K-12 mgs described by Riley et al. (Nucleic Acids Res. 34 (1), 1-9 (2006)) and set forth as GenBank accession number NP_415483.

The term "lacA" (lacA) is intended to include galactose transacetylase, an enzyme involved in lactose metabolism. By convention, the term "lacA" refers to a galactose transacetylase gene whereas the term "LACA" refers to a lacA gene product, i.e., a galactose transacetylase polypeptide or enzyme. An exemplary lacA sequence is the *E. coli* K-12 lacA described by Riley et al. (Nucleic Acids Res. 34 (1), 1-9 (2006)) and set forth as GenBank accession number NP_414876.

The term "lacY" (lacY) is intended to include permease, an enzyme involved in lactose metabolism. By convention, the term "lacY" refers to a permease gene whereas the term "LACY" refers to a lac Y gene product, i.e., a permease polypeptide or enzyme. An exemplary lacY sequence is the *E.*

*coli* K-12 lacY described by Riley et al. (Nucleic Acids Res. 34 (1), 1-9 (2006)) and set forth as GenBank accession number NP_414877.

As used herein the term "urease" is intended to refer to an enzyme that catalyzes the hydrolysis of urea into carbon dioxide and ammonia. Urease is encoded by genes in a ureDABCEFG operon.

The terms "fermentation" and "fermenting" are intended to include the degradation or depolymerization of a complex sugar and bioconversion of that sugar residue into ethanol, lactate, acetate and succinate under anaerobic condition. The terms are intended to include the enzymatic process (e.g. cellular or acellular, e.g. a lysate or purified polypeptide mixture) by which ethanol is produced from a carbohydrate, in particular, as a primary product of fermentation.

The term "Gram-negative bacteria" is intended to include the art-recognized definition of this term. Exemplary Gram-negative bacteria include *Acinetobacter, Gluconobacter, Escherichia, Zymomonas, Geobacter, Shewanella, Salmonella, Shigella, Eneterobacter, Citrobacter, Erwinia, Serratia, Proteus, Hafnia, Yersinia, Morganella, Edwardsiella*, and *Klebsiella*.

The term "Gram-positive bacteria" is intended to include the art-recognized definition of this term. Exemplary Gram-positive bacteria include *Bacillus, Clostridium, Corynebacterium, Geobacillis, Lactobacillis, Lactococcus, Oenococcus, Streptococcus* and *Eubacterium*.

The term "ethanologenic" is intended to include cells that have the ability to produce ethanol from a carbohydrate as a primary fermentation product. The term is intended to include naturally occurring ethanologenic organisms, ethanologenic organisms with naturally occurring or induced mutations, and recombinant organism genetically engineered to produce ethanol from a carbohydrate as a primary fermentation product.

The term "non-ethanologenic" is intended to include cells that are unable to produce ethanol from a carbohydrate as a primary non-gaseous fermentation product; i.e., cells that produce ethanol as a minor fermentation product.

The term "primary fermentation product" is intended to include non-gaseous products of fermentation (e.g., ethanol) that comprise greater than about 40%, 50%, 60%, 70%, 80%, 85%, 90%, 91%, 92%, 93%, 94%, 95% of total non-gaseous product. The primary fermentation product is the most abundant non-gaseous product. In certain embodiments of the invention, the primary fermentation product is ethanol.

The term "minor fermentation product" as used herein is intended to include non-gaseous products of fermentation (e.g., ethanol) that comprise less than 40%, for example 20%, 30%, 40%, of total non-gaseous product.

The term "anaerobic conditions" in intended to include conditions in which there is significantly less oxygen than is present in an aerobic environment, wherein an aerobic environment is defined as an oxygen saturated liquid. In particular embodiments, there is 40%, 50%, 60%, 70%, 80%, 85%, 90%, 91%, 92%, 93%, 94%, 95%, 96%, 97%, 98%, 99%, 99.5% or less oxygen in the anaerobic environment than in the aerobic environment. In another embodiment, the anaerobic condition is one in which trace or an immeasurable amount of oxygen is present. An anaerobic environment is also one in which oxygen is fed into the fermentation vessel, but wherein the amount fed is of such a small amount that the fermenting organism consumes all or almost all of the oxygen as oxygen is added, such that little to no oxygen accumulates in the environment. The term "simultaneous saccharification and fermentation" or "SSF" is intended to include the use of one or more recombinant hosts (or extracts thereof, including purified or unpurified extracts) for the contemporaneous degradation or depolymerization of a complex sugar and bioconversion of that sugar residue into ethanol by fermentation. SSF is a well-known process that can be used for breakdown of biomass to polysaccharides that are ultimately convertible to ethanol by bacteria. Reflecting the breakdown of biomass as it occurs in nature, SFF combines the activities of fungi (or enzymes such as cellulases extracted from fungi) with the activities of ethanologenic bacteria (or enzymes derived therefrom) to break down sugar sources such as lignocellulose to simple sugars capable of ultimate conversion to ethanol. SSF reactions are typically carried out at acid pH to optimize the use of the expensive fungal enzymes.

The term "homologous recombination" refers to the crossing over of DNA that occurs between two homologous DNA molecules. According to the invention, homologous recombination can occur between genes to restore gene function, i.e. homologous recombination to restore pflB function. In another embodiment, homologous recombination can be used to remove an antibiotic resistance marker.

The terms "saccharide," "saccharide source," "oligosaccharide source," "oligosaccharide," "complex cellulose," "complex carbohydrate," "complex sugar," "polysaccharide," "sugar source," "source of a fermentable sugar" and the like are intended to include any carbohydrate source comprising more than one sugar molecule. Sugars include glucose, xylose, arabinose, mannose, galactose, sucrose, and lactose. The term "saccharide," as used herein, also includes, e.g., disaccharides, trisaccharides, oligosaccharides, and polysaccharides. These carbohydrates may be derived from any unprocessed plant material or any processed plant material. Examples are wood, paper, pulp, plant derived fiber, or synthetic fiber comprising more than one linked carbohydrate moiety, i.e., one sugar residue. One particular saccharide source is "lignocellulose," which represents approximately 90% of the dry weight of most plant material and contains carbohydrates, e.g., cellulose, hemicellulose, pectin, and aromatic polymers, e.g., lignin. Cellulose makes up 30%-50% of the dry weight of lignocellulose and is a homopolymer of cellobiose (a dimer of glucose). Similarly, hemicellulose makes up 20%-50% of the dry weight of lignocellulose and is a complex polymer containing a mixture of pentose (xylose, arabinose) and hexose (glucose, mannose, galactose) sugars which contain acetyl and glucuronyl side chains. Pectin makes up 1%-20% of the dry weight of lignocellulose and is a methylated homopolymer of glucuronic acid.

Other saccharide sources include carboxymethyl cellulose (CMC), amorphous cellulose (e.g., acid-swollen cellulose), and the cellooligosaccharides cellobiose, cellotriose, cellotetraose, and cellopentaose. Cellulose, e.g., amorphous cellulose may be derived from a paper or pulp source (including, e.g., fluid wastes thereof) or, e.g., agricultural byproducts such as corn stalks, soybean solubles, or beet pulp. Any one or a combination of the above carbohydrate polymers is a potential source of sugars for depolymerization and subsequent bioconversion to ethanol by fermentation according to the products and methods of the present invention.

The term "obtaining" as in "obtaining the recombinant bacterium" is intended to include purchasing, preparing, engineering or otherwise acquiring the recombinant bacterium.

The term "providing" as in "providing the recombinant bacterium" is intended to include selling, distributing or otherwise making available the recombinant bacterium.

"ATCC" followed by a number appearing in parentheses following an organism name refers to a deposit of the organism made with the American Type Culture Collection, 10801 University Blvd. Manassas, Va. 20110-2209.

"NRRL" followed by a number appearing in parentheses following an organism name refers to a deposit of the organism made with the ARS Culture Collection, located at the National Center for Agricultural Utilization Research, 1815 N. University St. Peoria, Ill. 61604.

II. Recombinant Cells

As discussed, the invention provides new and recombinant cells, in particular recombinant bacteria, suitable for degrading sugars and/or producing ethanol. The cells have improved ethanol production capabilities, particularly. The cells comprise ethanol production genes, urease genes and the deletion of mgsA.

The cell can also be a cell of a single-celled or multicellular microorganism, such as a fungus, yeast, or bacterium. The recombinant host cells and recombinant cells derived therefrom are intended to include cells suitable for, or subjected to, genetic manipulation, or to incorporate heterologous polynucleotide sequences by transfection. Recombinant host cells include progeny of the host cell originally transfected.

Accordingly, suitable host cells in accordance with the invention include yeast cells such as, e.g., *Saccharomyces cerevisiae*. Other yeast cells in accordance with the invention include, e.g., *Saccharomyces, Schizosacharomyces, Hansenula, Pachyosolen, Kluyveromyces, Debaryomyces, Yarrowia*, and *Pichia*.

The host cell can be a non-recombinant or recombinant bacterial host cell. In certain embodiments, bacterial host cells in accordance with the invention include Gram-positive bacteria, e.g., *Bacillus, Clostridium, Corynebacterium, Geobacillis, Lactobacillis, Lactococcus, Oenococcus, Streptococcus* and *Eubacterium*. In other embodiments, bacterial host cells include Gram-negative bacteria and include, for example, *Acinetobacter, Gluconobacter, Escherichia, Zymomonas, Geobacter, Shewanella, Salmonella, Shigella, Eneterobacter, Citrobacter, Erwinia, Serratia, Proteus, Hafnia, Yersinia, Morganella, Edwardsiella*, and *Klebsiella*. Exemplary bacterial host cells in accordance with the invention include non-recombinant bacteria such as, e.g., *Escherichia coli* B or *Escherichia coli* W.

As discussed, the invention provides recombinant cells, in particular recombinant bacteria, comprising ethanol production genes. The recombinant bacteria of the invention are able to produced ethanol as the primary fermentation product.

The organisms contain ethanol production genes. Included within the scope of the invention are heterologous ethanol production genes derived from yeast and Gram-positive or Gram-negative bacteria. Thus, suitable heterologous polynucleotide sequences for use in constructing recombinant organisms in accordance with the invention are derived from, e.g., adh and/or pdc genes from naturally occurring ethanologenic organisms, such as *Zymomonas mobilis* and *Saccharomyces cerevisiae*, as well as *Zymobacter palmae, Acetobacter pasteurianus* and *Sarcinia ventriculi* (WO2003/025117 and herein incorporated by reference; Talarico et al. 2005.). Other naturally occurring ethanologenic organisms from which ethanol production genes can be derived for use in the invention include fungi and most plants.

One or more of the ethanol production genes can be derived from different organisms or from the same organisms. In advantageous embodiments, the genes are derived from the same organism.

In one embodiment of the invention, the genes comprising the ous ethanol production genes are pdc, adhA and adhB. In an advantageous embodiment, the pdc, adhA and adhB genes are from *Zymomonas mobilis*, a naturally occurring ethanologenic bacterium.

Included within the scope of the invention are heterologous ethanol production genes or gene products which differ from naturally-occurring ethanol production genes, for example, genes which have nucleic acids that are mutated, inserted or deleted, but which encode polypeptides substantially similar and functionally equivalent to the naturally-occurring gene products of the present invention, e.g., a mutant polypeptide having pyruvate decarboxylase activity that serves to direct the flow of pyruvate into ethanol during fermentation.

For example, it is well understood to one of skill in the art that nucleic acids which code for conservative amino acid substitutions can be mutated (e.g., by substitution). It is further well understood to one of skill in the art that amino acids in the naturally occurring gene products can be substituted, added or deleted to a certain degree without substantially affecting the function of a gene product (e.g., without affecting the biological function of pyruvate decarboxylase as an enzyme that serves to direct the flow of pyruvate into ethanol during fermentation) as compared with a naturally-occurring gene product. These well understood principles are included within the scope of the present invention. Thus, although in some embodiments, the ethanol production genes can comprise, for example, the naturally occurring pdc, adhA and adhB genes of *Zymomonas mobilis*, one or more genes can be mutated forms of naturally occurring ethanol production genes, e.g., *Zymomonas mobilis* ethanol production genes.

In other aspects, the invention provides a recombinant bacterium which comprises ethanol production genes as herein before described, wherein one or more antibiotic markers are removed. In general, genes encoding antibiotic markers are used in recombinant engineering techniques to identify or mark the presence of a particular genotype/phenotype. In certain embodiments, recombinant organisms of the invention which produce ethanol as the primary fermentation product can be inhibited by the presence of antibiotic markers. Therefore, such antibiotic markers are advantageously removed from the recombinant organisms. In some embodiments, antibiotic markers targeted for removal include, e.g., those selected from the group consisting of apramycin, kanamycin, tetracycline, ampicillin and chloramphenicol. In certain embodiments, apramycin and kanamycin markers are removed. In other embodiments, the organism contain a selectable marker that is a non-antibiotic maker, e.g., green fluorescent protein.

In another embodiment, a msgA gene is inactivated by deletion. This gene encodes a protein involved in the Methylglyoxal Bypass, a spillover pathway which is a potential source of lactate in *E. coli* and which slows glycolysis and macromolecular synthesis (Totemeyer et al. 1998, Zhu et al. 2001).

In other aspects, the invention provides a recombinant bacterium which comprises ethanol production genes as hereinbefore described, and which further comprises urease genes. For example, the recombinant bacterium contains the *K. oxytoca* urease operon comprising ureDABCEFG genes. Such genes can be endogenous or heterologous and are integrated into the host cell by any number of techniques well known to those of skill in the art.

Exemplary recombinant organisms in accordance with the invention are novel *E. coli* strain SD7. This strain was deposited with the NRRL on Jun. 16, 2010 and assigned NRRL accession number B-50394). In accordance with an embodiment of the invention, these novel *E. coli* strains are produced from the recombinant *E. coli* KO11 (ATCC 55124) (Ohta et al. 1991), which is used as the host cell. Methods for producing these novel strains are described in the examples below.

III. Methods of Making

The present invention provides methods of making the recombinant organisms having the aforementioned attributes. Accordingly, in another aspect, the invention provides a method for producing a recombinant bacterium that comprises ethanol production genes and urease genes, and also have an inactivated msgA gene.

Methods of making recombinant ethanologenic microorganisms are known in the art of molecular biology. Suitable materials and methods and recombinant host organisms are described, for example, in U.S. Pat. Nos. 7,026,152, 6,849, 434, 6,333,181, 5,821,093; 5,482,846; 5,424,202; 5,028,539; 5,000,000; 5,487,989, 5,554,520, and 5,162,516 and in WO2003/025117 hereby incorporated by reference, and may be employed in carrying out the present invention.

The genes include a nucleic acid molecule (e.g., a DNA molecule or segment thereof), for example, a polypeptide or RNA-encoding nucleic acid molecule that, in an organism, is separated from another gene or other genes, by intergenic DNA (i.e., intervening or spacer DNA which naturally flanks the gene and/or separates genes in the chromosomal DNA of the organism). A gene can direct synthesis of an enzyme or other polypeptide molecule (e.g., can comprise coding sequences, for example, a contiguous open reading frame (ORF) which encodes a polypeptide) or can itself be functional in the organism. A gene in an organism can be clustered in an operon, as defined herein, wherein the operon is separated from other genes and/or operons by intergenic DNA. Individual genes contained within an operon can overlap without intergenic DNA between the individual genes. Also included in the scope of the invention are promoterless operons, which are operons lacking the promoter portion (e.g., an frd or ure operon).

An isolated gene as described herein, includes a gene which is essentially free of sequences which naturally flank the gene in the chromosomal DNA of the organism from which the gene is derived (i.e., is free of adjacent coding sequences which encode a second or distinct polypeptide or RNA molecule, adjacent structural sequences or the like) and optionally includes 5' and 3' regulatory sequences, for example promoter sequences and/or terminator sequences. An isolated gene includes predominantly coding sequences for a polypeptide (e.g., sequences which encode PDC polypeptides).

In some embodiments, the parent strain is a non-recombinant bacterium. For example, the parent strain can be a naturally occurring non-ethanologenic bacterium, e.g., *E. coli* W.

In other embodiments of the invention, the parent strain can be a recombinant organism.

Exemplary host cells for use in the methods according to the invention include, e.g., *E. coli* strains B, W, KO4 (ATCC 55123), KO11 (ATCC 55124), and KO12 (ATCC 55125), and *Klebsiella oxytoca* strain P2 (ATCC 55307) (U.S. Pat. No. 5,821,093). Other examples of suitable host cells include *E. coli* (ATCC 11303), *E. coli* DH5α, *E. coli* C, *E. coli* K12, *E. coli* KO4 (ATCC 55123), *E. coli* LY01 (ATCC PTA-3466), *E. coli* W (ATCC 9637), and *K. oxytoca* M5A1 (ATCC 68564).

In yet another embodiment, the method further comprises removing one or more antibiotic markers. In one embodiment, the antibiotic markers are selected from the group consisting of apramycin, kanamycin, tetracycline, ampicillin and chloramphenicol. In a particular embodiment, the antibiotic markers are apramycin and kanamycin. The antibiotic marker can be removed by inactivating (e.g., by deletion) the gene coding for the marker by any of a number of methods known in the art. In an advantageous embodiment, the gene(s) encoding the antibiotic marker(s), e.g., kanamycin and apramycin, is removed by homologous recombination, using a recombinase.

In yet another embodiment, the method further comprises adding one or more screenable markers, e.g., a marker such as green fluorescent protein.

In yet another embodiment, the method further comprises inactivating one or more genes encoding polypeptides that interfere with or otherwise reduce the amount of ethanol produced by the ethanol production genes. In accordance with the invention, such genes are inactivated by any of a number of means, well known to those of skill in the art, by which a gene is stopped from encoding its intended polypeptide or from encoding an active form of its intended polypeptide. Accordingly, such genes are inactivated by, for example, mutation, deletion, insertion, duplication, missense, frameshift, repeat, nonsense mutation, or other alteration or modification such that gene activity (i.e., transcription) is blocked or transcription results in functionally inactive polypeptides. In accordance with advantageous embodiments of the invention, genes are inactivated by deletion.

In a further embodiment, the method further comprises integrating one or more heterologous genes that encode polypeptides that facilitate production of ethanol or otherwise increase the amount of ethanol produced by the ethanol production genes. The very same methods described above that are used to integrate the ethanol production genes can be used to integrate genes that encode polypeptides that facilitate production of ethanol or otherwise increase the amount of ethanol produced by the microorganism.

It is understood by those of ordinary skill in the art that the aforementioned genetic changes to the bacteria of the invention can be carried out in any order and that the order of adding genes or decreasing the expression of genes can be varied but still result in the recombinant bacteria of the invention.

One of ordinary skill in the art will recognize that based on the aforementioned examples, and based on homology among bacterial strains, the methods of the invention are not limited to the strains taught in the instant application.

IV. Methods of Use

Methods for Producing Ethanol

The recombinant bacteria of the invention produce ethanol from an oligosaccharide source. Accordingly, the invention provides a method for producing ethanol from an oligosaccharide source comprising contacting said oligosaccharide with a recombinant bacterium of the invention under conditions appropriate for ethanol production, thereby producing ethanol from an oligosaccharide source.

In accordance with the methods of the invention, the recombinant bacteria described herein degrade or depolymerize a complex saccharide into a monosaccharide. Subsequently, the recombinant bacteria, catabolize the simpler sugar into ethanol by fermentation.

Typically, fermentation conditions are selected that provide an optimal pH and temperature for promoting the best growth kinetics of the producer host cell strain and catalytic conditions for the enzymes produced by the culture (Doran et al., (1993) *Biotechnol. Progress.* 9:533-538). A variety of exemplary fermentation conditions are disclosed in U.S. Pat. Nos. 5,487,989 and 5,554,520. In certain embodiments, optimal conditions included temperatures ranging from about 25 to about 43° C. and a pH ranging from about 4.5 to 8.0. Other conditions are discussed in the Examples. Moreover, it will be appreciated by the skilled artisan that only routine experimentation is needed, using techniques known in the art, for optimizing a given fermentation reaction of the invention.

Currently, the conversion of a complex saccharide such as lignocellulose is a very involved, multi-step process. For example, the lignocellulose must first be degraded or depolymerized using acid hydrolysis. This is followed by steps that separate liquids from solids and these products are subsequently washed and detoxified to result in cellulose that can be further depolymerized and finally, fermented by a suitable ethanologenic host cell. In contrast, the fermenting of corn is much simpler in that amylases can be used to break down the corn starch for immediate bioconversion by an ethanologenic host in essentially a one-step process.

Accordingly, it will be appreciated by the skilled artisan that the recombinant hosts and methods of the invention afford the use of a similarly simpler and more efficient process for fermenting lignocellulose. For example, the method of the invention is intended to encompass a method that avoids acid hydrolysis altogether. Moreover, the hosts of the invention have the following advantages, 1) efficiency of pentose and hexose co-fermentation; 2) resistance to toxins; 3) production of enzymes for simultaneous saccharification and fermentation; and 4) environmental hardiness. Therefore, the complexity of depolymerizing lignocellulose can be simplified using an improved biocatalyst of the invention.

One advantage of the invention is the ability to use a saccharide source that has been, heretofore, underutilized. Consequently, a number of complex saccharide substrates may be used as a starting source for depolymerization and subsequent fermentation using the recombinant bacteria and methods of the invention. Ideally, a recyclable resource may be used in the SSF process. Mixed waste office paper is a preferred substrate (Brooks et al., (1995) *Biotechnol. Progress.* 11:619-625; Ingram et al., (1995) U.S. Pat. No. 5,424,202), and is much more readily digested than acid pretreated bagasse (Doran et al., (1994) *Biotech. Bioeng.* 44:240-247) or highly purified crystalline cellulose (Doran et al. (1993) *Biotechnol. Progress.* 9:533-538). Glucanases, both endoglucanases and exoglucanases, contain a cellulose binding domain, and these enzymes can be readily recycled for subsequent fermentations by harvesting the undigested cellulose residue using centrifugation (Brooks et al., (1995) *Biotechnol. Progress.* 11:619-625). Such approaches work well with purified cellulose, although the number of recycling steps may be limited with substrates with a higher lignin content. Other substrate sources that are within the scope of the invention include any type of processed or unprocessed plant material, e.g., lawn clippings, husks, cobs, stems, leaves, fibers, pulp, hemp, sawdust, newspapers, etc.

EXEMPLIFICATION

The invention is further illustrated by the following examples, which should not be construed as limiting.

Example 1

Preparation of *E. coli* SD7

Materials and Methods

Chromosomal DNA was prepared from *E. coli* SD7 by growing an overnight culture on Luria broth, harvesting the cells, and treating the cells with reagents to lyse the cell membrane and release the DNA. After a phenol-chloroform step to eliminate cell proteins, the DNA was precipitated and resuspended in buffer for use in the PCR reactions.

The following PCR primer sets and conditions were used to amplify the region encompassing each of the modifications introduced into *E. coli* SD7. The expected size of the PCR product is indicated for each.

| Set 1 | introduction of *K. oxytoca* urease operon | Product size |
|---|---|---|
| Forward | 5' CAGCAGCGAAACTGTTTGCCA 3' (SEQ ID NO: 8) | 5.4 kb |
| Reverse | 5' GTGCGATGTGGTTTGTAGGCATGAT 3' (SEQ ID NO: 9) | |
| Set 2 | deletion of the mgsA gene | |
| Forward | 5' TGATGGCAGATGACAGTACGCTG 3' (SEQ ID NO: 10) | 0.5 kb |
| Reverse | 5' GGCAACAGGCGGATTACGTCA 3' (SEQ ID NO: 11) | |

PCR Cycling Conditions for Amplification were as Follows:

| Step 1 | 95° C. | 5 minutes |
| Step 2 | 95° C. | 30 seconds |
| Step 3 | 55° C. | 30 seconds |
| Step 4 | 68° C. | 1 minute per kb of expected product |
| Repeat steps 2-4 34 times | | |
| Step 5 | 68° C. | 7 minutes |

All PCR reactions resulted in products of the expected size as analyzed by agarose gel electrophoresis. Each of the PCR products were purified using a spin column method (Qiaquick columns, Qiagen, Valencia, Calif.) and treated with Exo-SapIT (US Biochemicals, Cleveland, Ohio) to prepare for sequencing by the dideoxy chain termination method.

Results and Conclusions

Removal of Alcohol Gene Cassette from *E. Coli* KO11-RD1.

*E. coli* KO11-RD1, contains an alcohol gene cassette. The complete removal of the alcohol gene cassette by recombination was carried out by the two-step, recombinational method and should result in the complete restoration of the wild-type pflB gene, the original site of insertion. The nucleotide sequence of this region was determined, following PCR amplification, and found to be identical to that found in parental strain *E. coli* W. The nucleotide sequence of the *E. coli* SD5 pflB region is shown in FIG. 1.

Deletion of the frdABCD Operon.

*E. coli* is capable of producing succinate as a fermentation product through the actions of the fumarate reductase, encoded by frdABCD. *E. coli* KO11-RD1 contains an insertion of bacteriophage Mu sequences in the frdA gene that eliminates succinate production but is capable of reversion. A complete and precise deletion of the entire frdABCD operon and removal of the inserted Mu sequences was carried out by the two-step, recombinational method. Confirmation of the deletion and removal was obtained by PCR amplification and nucleotide sequencing of this region. The resultant sequence is shown in FIG. 2.

Deletion of Lactate Dehydrogenase Gene ldhA.

The lactate dehydrogenase gene, ldhA, was deleted to eliminate production of lactate by fermentation using the by the two-step, recombinational method. PCR amplification and nucleotide sequencing of the region confirmed the precise deletion of the gene. The resultant sequence is shown in FIG. 3.

Introduction of the pdc$^{Ec^o}$-adhA$^{Ec^o}$-adhB$^{Ec^o}$-gfp$^{Ec^o}$ Alcohol Operon into Ribosomal Operon H.

An alcohol operon consisting of *E. coli* codon-optimized *Zymomonas mobilis* pyruvate decarboxylase (pdc), alcohol dehydrogenase I (adhA), alcohol dehydrogenase II (adhB) and green fluorescent protein (gfp) genes was introduced by the two-step, recombinational method into the 23S rrn gene of the ribosomal operon H. To confirm the location of the insertion site and the composition of the alcohol operon, a 10 kb PCR product was amplified and the nucleotide sequence determined. A smaller portion of the sequence obtained shows the site of insertion and composition of the alcohol operon genes (FIG. 4).

Deletion of Bacteriophage Wφ gpN.

To eliminate bacteriophage Wφ production, the major capsid gene gpN was deleted by the two-step, recombinational method. Confirmation of the deletion was carried out by PCR amplification and nucleotide sequencing of this region. The resultant sequence is shown in FIG. 5.

Insertion of the *Klebsiella oxytoca* Urease Operon.

To introduce the *K. oxytoca* M5A1 urease operon into *E. coli* SD5 to enable the use of urea as an alternative nitrogen source, a 5 kb PCR product was generated from *K. oxytoca* M5A1 chromosomal DNA and ligated into a plasmid consisting of the pMEV vector and flanking *E. coli* W sequences from the downstream end of the proVWX operon. The constructed plasmid was used to introduce the urease operon into *E. coli* SD6 by the two-step, recombinational method. The introduction was confirmed by PCR and nucleotide sequencing. The resultant sequence is shown in FIG. 6.

Deletion of the Methylglyoxal Synthase Gene, mgsA.

To delete the mgsA gene and eliminate methylglyoxal and residual lactate production, a region of the *E. coli* W genome sequence flanking the mgsA open reading frame was used to design and synthesize a DNA fragment that was then cloned into pMEV. The deletion was introduced by the two-step, recombinational method and confirmed by PCR analysis and nucleotide sequencing. The resultant sequence is shown in FIG. 7.

Example 2

Preparation and Characterization of *E. coli* SD7

*Escherichia coli* SD7 is used to ferment C5 sugars from lignocellulosic biomass to ethanol. *Escherichia coli* SD7 is an intergeneric microorganism, and its identity is described in detail below.

Taxonomic Information
Recipient Organism

The recipient microorganism is *Escherichia coli* W. The general taxonomy of *E. coli* is as follows:
 Name: *Escherichia coli*
 Kingdom: Bacteria
 Phylum: Proteobacteria
 Class: Gammaproteobacteria
 Order: Enterobacteriales
 Family: Enterobacteriaceae
 Genus: *Escherichia*
 Species: coli

*E. coli* W is available from American Type Culture Collection (ATCC accession 9637) (ATCC, Accessed Jul. 9, 2007).

New Microorganism

*E. coli* SD7 was constructed via the following modifications starting from *E. coli* W.

1) Introduction of alcohol operon consisting of the *Zymomonas mobilis* pyruvate decarboxylase gene (pdc), *Z. mobilis* alcohol dehydrogenase II gene (adhB) and pBR325 chloramphenicol acetyltransferase (cat) gene into the pflB gene (superseded by step 5). Resulted in strain KO3;

2) Amplification of alcohol operon copy number by selection for high-level chloramphenicol resistance. Resulted in strain KO4;

3) Insertional inactivation of the frdA gene to eliminate succinate production and introduction of 128 kb of homologous *E. coli* K12 DNA flanking mutation. (Superseded by step 6.) Resulted in strain KO11;

4) Adaptation to biomass hydrolysate through multiple passages on solid agar containing increasing concentrations of hydrolysate. Resulted in strain KO11-RD1;

5) Removal of alcohol operon and chloramphenicol acetyltransferase gene (supersedes step 1). Resulted in strain SD1;

6) Deletion of frdABCD operon to eliminate succinate production (supersedes step 2). Resulted in strain SD2;

7) Deletion of lactate dehydrogenase gene, ldhA, to eliminate lactic acid production. Resulted in strain SD3;

8) Introduction of codon-optimized *Z. mobilis* pyruvate decarboxylase (pdc), alcohol dehydrogenase I (adhA), alcohol dehydrogenase II (adhB), and green fluorescent protein gene (gfp) into rrlH ribosomal operon. Resulted in strain SD4; and 9) Deletion of bacteriophage Wφ major capsid gene, gpN, to remove ability to produce infectious phage particles. Resulted in strain SD5.

10) Introduction of the *Klebsiella oxytoca* urease operon genes, ureDABCEFG, into the chromosome, downstream of the native proVWX operon. Resulted in strain SD6.

11) Deletion of methylglyoxal synthase gene, mgsA, to remove methylglyoxal and residual lactic acid production. Resulted in strain SD7.

SD7 Morphological Features

*E. coli* is a Gram-negative bacterium. The cells are straight rods occurring singly or in pairs (Holt, J. G. et al., 1994c). The integration of the decarboxylase gene (pdc) and the alcohol dehydrogenase I and II genes (adhA and adhB) from *Zymomonas moblis* and the green fluorescent protein gene (gfp) into *E. coli* W along with the deletion of the ldhA, frdABCD, and gpN genes changes the cell morphology. The cell morphology of *E. coli* SD7 differs only in length compared to *E. coli* W. When cultivated in Luria-Bertani broth, supplemented with 2% glucose, during log-phase growth, the *E. coli* W cells are 0.9 μm×2.6 μm-4.3 μm. The majority of *E. coli* SD7 cells are shorter, 0.9 μm×1.7 μm-3.4 μm, with some longer cells reaching 37 μm in length.

The adaptation of one of the intermediates in the construction of *E. coli* SD7, KO11-RD1, to biomass hydrolysate resulted in a change in the colony morphology as compared to *E. coli* W. Where *E. coli* W colonies are flat and translucent, KO11-RD1 and its derivatives, including *E. coli* SD7, are raised and mucoidal.

Physiological Features

*E. coli*, including the W strain, is a facultative anaerobe and able to ferment hexose and pentose sugars to a variety of organic acids, ethanol and hydrogen (a process termed heterofermentation). The organic acids include formate, acetate, lactate, and succinate (August, B. et al., 1996). To eliminate the most significant organic acid by-products, i.e., lactate and succinate production, respectively, the fermentatative lactate dehydrogenase gene, ldhA, and the fumarate reductase operon, frdABCD, were deleted from SD7. To increase ethanol production, heterologous genes for the conversion of pyruvate to ethanol—consisting of the *Zymomonas mobilis* pyruvate decarboxylase gene (pdc), the alcohol dehydrogenase I gene (adhA), and the alcohol dehydrogenase II gene (adhB)—were introduced into *E. coli* SD7. While this strain retains the ability to produce acetate, formate, and hydrogen, it produces predominantly ethanol due to the increased flux of pyruvate to this end-product enabled by the introduction of the *Z. mobilis* genes. To enable the use of urea as an alternative nitrogen source, the urease operon from *Klebsiella oxytoca* M5A1, was cloned and introduced into the chromosome. Finally, to eliminate the production of methylglyoxal and residual lactic acid, the methylglyoxal synthase gene, mgsA, was deleted.

Genetic Construction of the New Microorganism
  Taxonomy of Donor Organism
  The taxonomies of the donor organisms used in the construction of *E. coli* SD7 are described below.
  The donor microorganism providing the pyruvate decarboxylase gene (pdc), the alcohol dehydrogenase I gene (adhA), and the alcohol dehydrogenase II gene (adhB) is *Zymomonas mobilis* ZM4. The general taxonomy of *Z. mobilis* is as follows:
    Name: *Zymomonas mobilis*
    Kingdom: Bacteria
    Phylum: Proteobacteria
    Class: Alphaproteobacteria
    Order: Sphingomonadales
    Family: Sphingomonadaceae
    Genus: *Zymomonas*
    Species: mobilis
  The donor microorganism providing the urease operon, ureDABCEFG, is *Klebsiella oxytoca* M5A1. The general taxonomy of *K. oxytoca* is as follows:
    Name: *Klebsiella oxytoca*
    Kingdom: Bacteria
    Phylum: Proteobacteria
    Class: Gammaproteobacteria
    Order: Enterobacteriales
    Family: Enterobacteriaceae
    Genus: *Klebsiella*
    Species: oxytoca Description of Natural Traits
  Natural
  *E. coli* W, the recipient microorganism, was chosen because it has a history of safe use and is well-characterized. There is a large amount of information available on *E. coli* in terms of metabolism, physiology, and genetics. *E. coli* is able to metabolize a wide variety of substrates, including dissacharides, hexoses, pentoses, and sugar alcohols (Holt, J. G. et al., 1994c). These substrates are converted to a variety of organic acids, ethanol, and hydrogen. The organic acids include formate, acetate, lactate, and succinate (August, B. et al., 1996). *E. coli* is considered the most widely-used host for molecular genetics, so its culture and molecular manipulations are well-known.

Added or Modified
  Although *E. coli* W is able to produce ethanol by fermentation through a heterofermentative process, the ability of *E. coli* SD7 to produce high levels of ethanol by homofermentation was introduced by the addition of *E. coli* codon-optimized (indicated by Ec°) *Z. mobilis* pyruvate decarboxylase and the alcohol dehydrogenase I and II genes. In addition, *E. coli* SD7 was modified to express low levels of green fluorescent protein by the introduction of the gfp gene to the pdc-adhA-adhB alcohol operon (further indicated as pdc$^{Ec°}$-adhA$^{Ec°}$-adhB$^{Ec°}$-gfp$^{Ec°}$ in the remainder of this submission) in order to aid monitoring of operon expression. The ability of *E. coli* SD7 to produce lactate or succinate as fermentation side products was eliminated by the deletion of the ldhA and frdABCD genes, respectively. The ability of *E. coli* SD7 to produce Wφ phage particles was eliminated, while retaining immunity to superinfection, by deletion of the Wφ major capsid protein gene gpN. The ability of *E. coli* SD7 to use urea as an alternative nitrogen source was introduced by the addition of the urease operon, consisting of the ureDABCEFG genes, from *Klebsiella oxytoca* M5A1. The ability of SD7 to produce methylglyoxal and residual amounts of lactate were eliminated by deletion of the methylglyoxal synthase gene mgsA.

Figure 9:
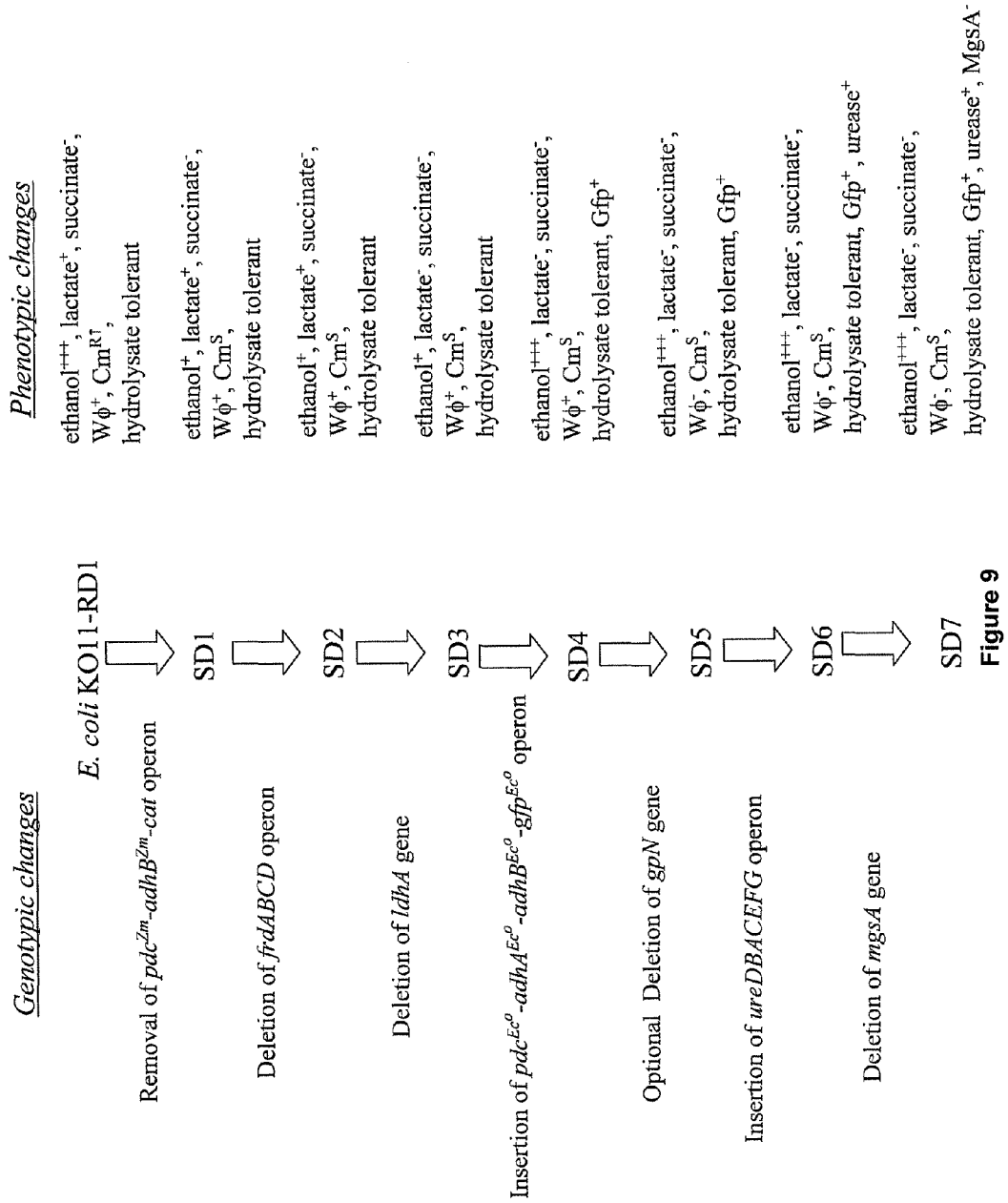
FIG. 9 depicts the lineage of E. coli KO11-RD1. Genetic changes and resultant phenotypic changes from E. coli W to E. coli KO11-RD1. Wf, ability to make viable Wf phage; pRK1, pRK2, large and small endogenous plasmids, respectively (Sobotkova, 1999); CmR, chloramphenicol-resistant.

Construction Details
  The Recipient Microorganism
  The recipient microorganism, *E. coli* W, is the progenitor of *E. coli* SD7 and a number of intermediate strains.
  *E. coli* SD7 was constructed for use in lignocellousic ethanol process and is derived from a previously modified strain *E. coli* KO11-RD1, which is a hydrolysate-resistance adapted derivative of KO11. *E. coli* KO11 has been extensively described in the literature and has been well-characterized for its ability to ferment pentose sugars to ethanol at high volume productivities (Asghari, A. et al., 1996). Although KO11 was originally described as having been generated from *E. coli* B, it has subsequently been shown to have been derived from *E. coli* W (ATCC 9637) (Jarboe, L. R. et al., 2007).
  The KO11-RD1 derivative is highly resistant to inhibitory components, such as furfural and hydroxymethyl furfural, found in the sugar liquor produced in the dilute acid/steam explosion pretreatment. In addition, the strain still retains properties such as the ability to produce fermentation side-products as well as ethanol. The steps taken to remedy these traits and to produce the new microorganism *E. coli* SD7 are described below. A lineage of the intermediates and the final strain is shown in FIGS. 8 and 9.

Introduced DNA Sequences
  Since the construction of *E. coli* KO11 is well-described in the literature and our effort to create *E. coli* SD7 begins with the use of *E. coli* KO11-RD1, the following discussion will focus on the sequence of events between KO11-RD1, the hydrolysate adapted strain, and *E. coli* SD7, the new microorganism. Table 1 indicates all DNA added during the construction events between KO11-RD1 and SD7.

TABLE 1

DNA Added During the Construction Events Between KO11-RD1 and SD7

| Introduced sequence | Protein coding or non-coding | Length (bp) | Description |
|---|---|---|---|
| RBS-SD | non-coding | 14 | Ribosome binding site |
| pdc$^{Ec°}$ | coding | 1707 | *E. coli* codon optimized *Zymomonas mobilis* pyruvate decarboxylase gene |
| RBS-SD | non-coding | 14 | Ribosome binding site |
| adhA$^{Ec°}$ | coding | 1014 | *E. coli* codon optimized *Zymomonas mobilis* alcohol dehydrogenase I gene |
| RBS-SD | non-coding | 14 | Ribosome binding site |
| adhB$^{Ec°}$ | coding | 1152 | *E. coli* codon-optimized *Zymomonas mobilis* |

TABLE 1-continued

DNA Added During the Construction Events Between KO11-RD1 and SD7

| Introduced sequence | Protein coding or non-coding | Length (bp) | Description |
|---|---|---|---|
| | | | alcohol dehydrogenase II gene |
| RBS-SD | non-coding | 14 | Ribosome binding site |
| gfp$^{Ec^o}$ | coding | 687 | E. coli codon optimized green fluorescent protein gene |
| terminator | non-coding | 28 | Transcriptional terminator sequence |
| ureDABCEFG | coding | 5048 | Urease operon from Klebsiella oxytoca M5A1 |

Genetic Method for Introducing the Modifications to Create E. Coli SD7 and all Intermediate Strains.

Figure 10:
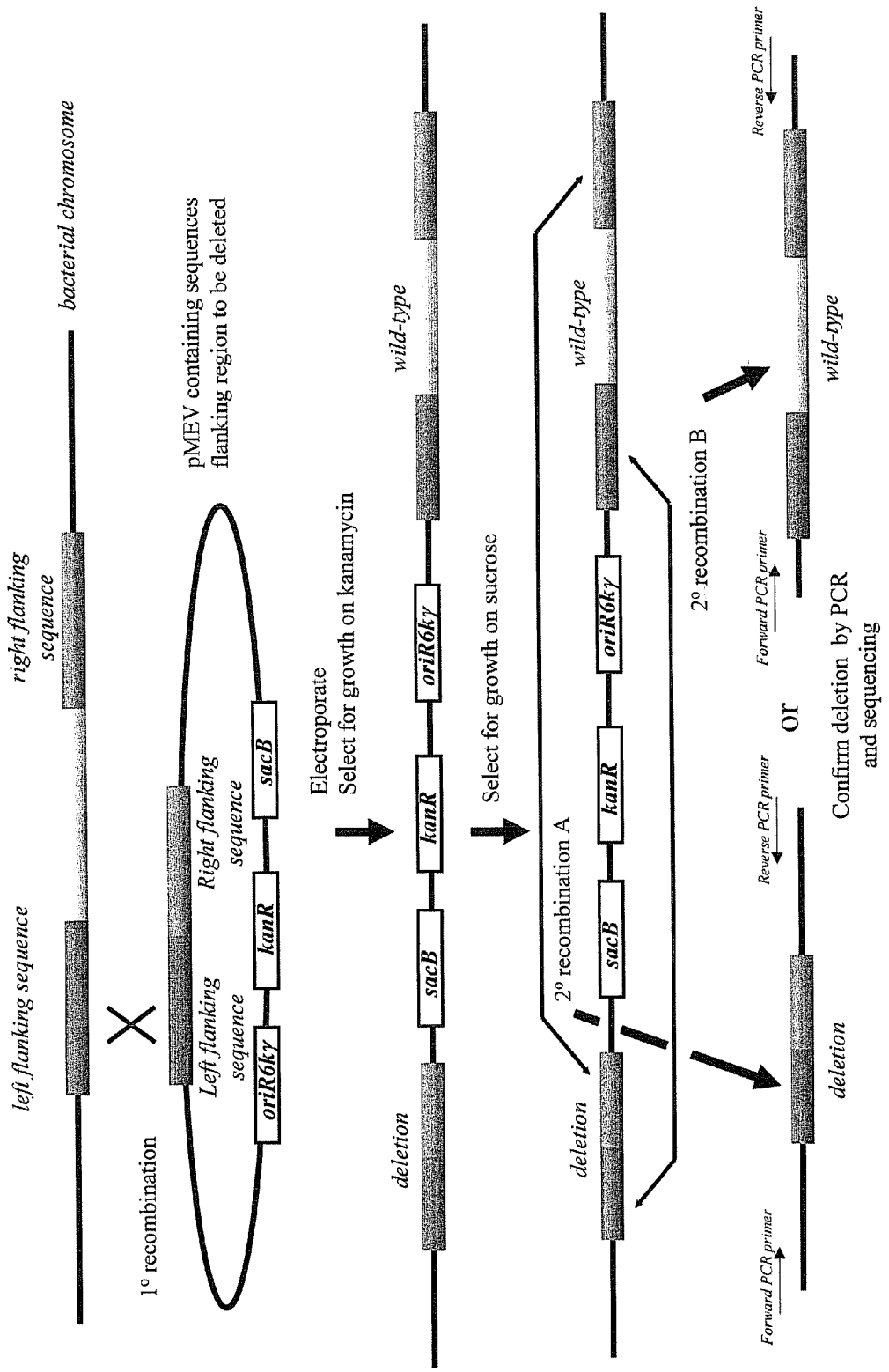
FIG. 10 depicts recombination exchange strategy-deletion. Schematic of steps for generating deletions without leaving behind antibiotic resistance gene or "scar". sacB, sucrose synthase gene; kan, aminoglycoside 3'-phosphotransferase; oriR6k, conditional origin of replication
Figure 11:
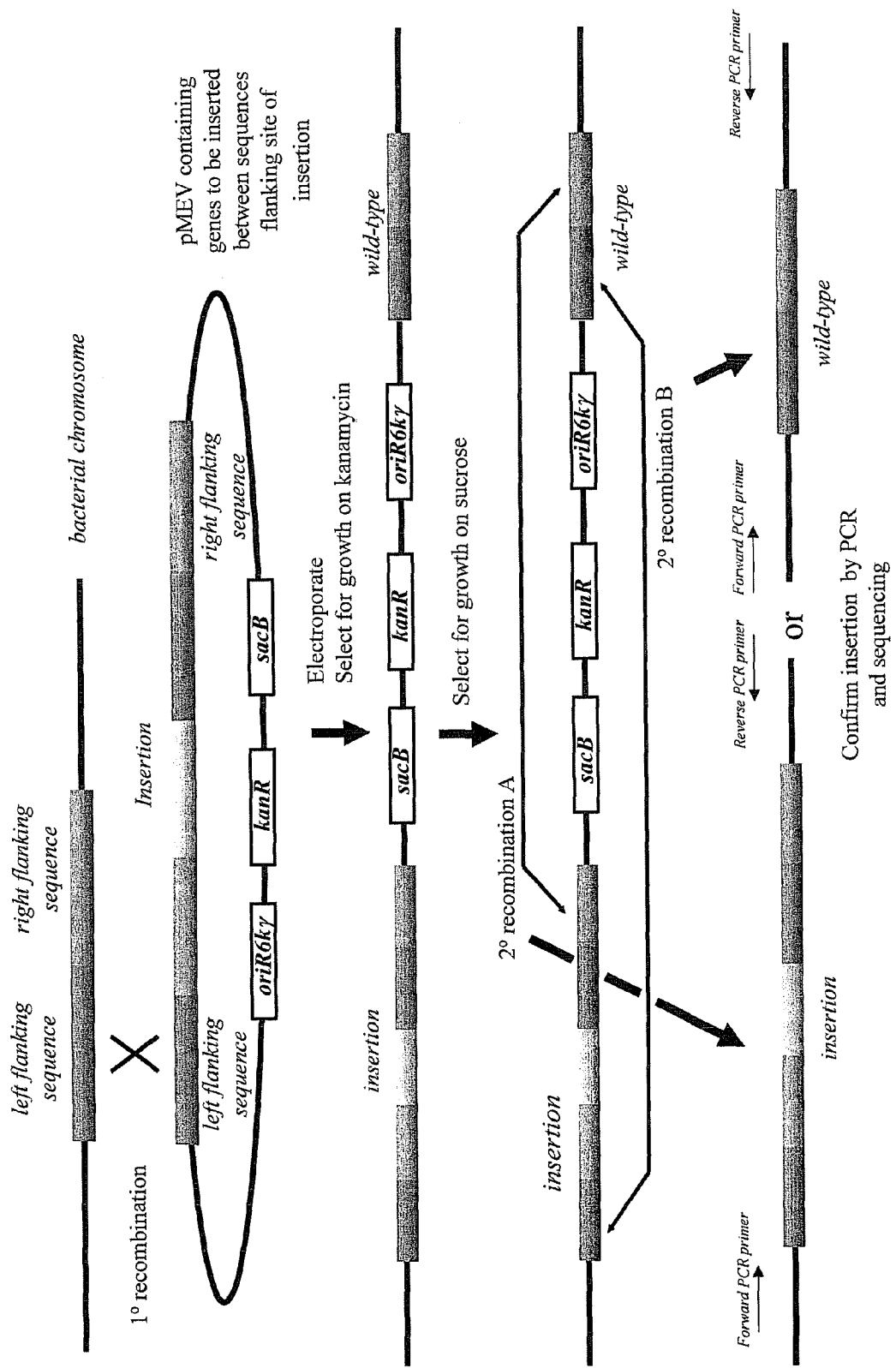
FIG. 11 depicts recombination exchange strategy-insertion. Schematic of steps for generating insertions without leaving behind antibiotic resistance gene or "scar". sacB, sucrose synthase gene; kan, aminoglycoside 3'-phosphotransferase; oriR6k, conditional origin of replication.
Figure 12:
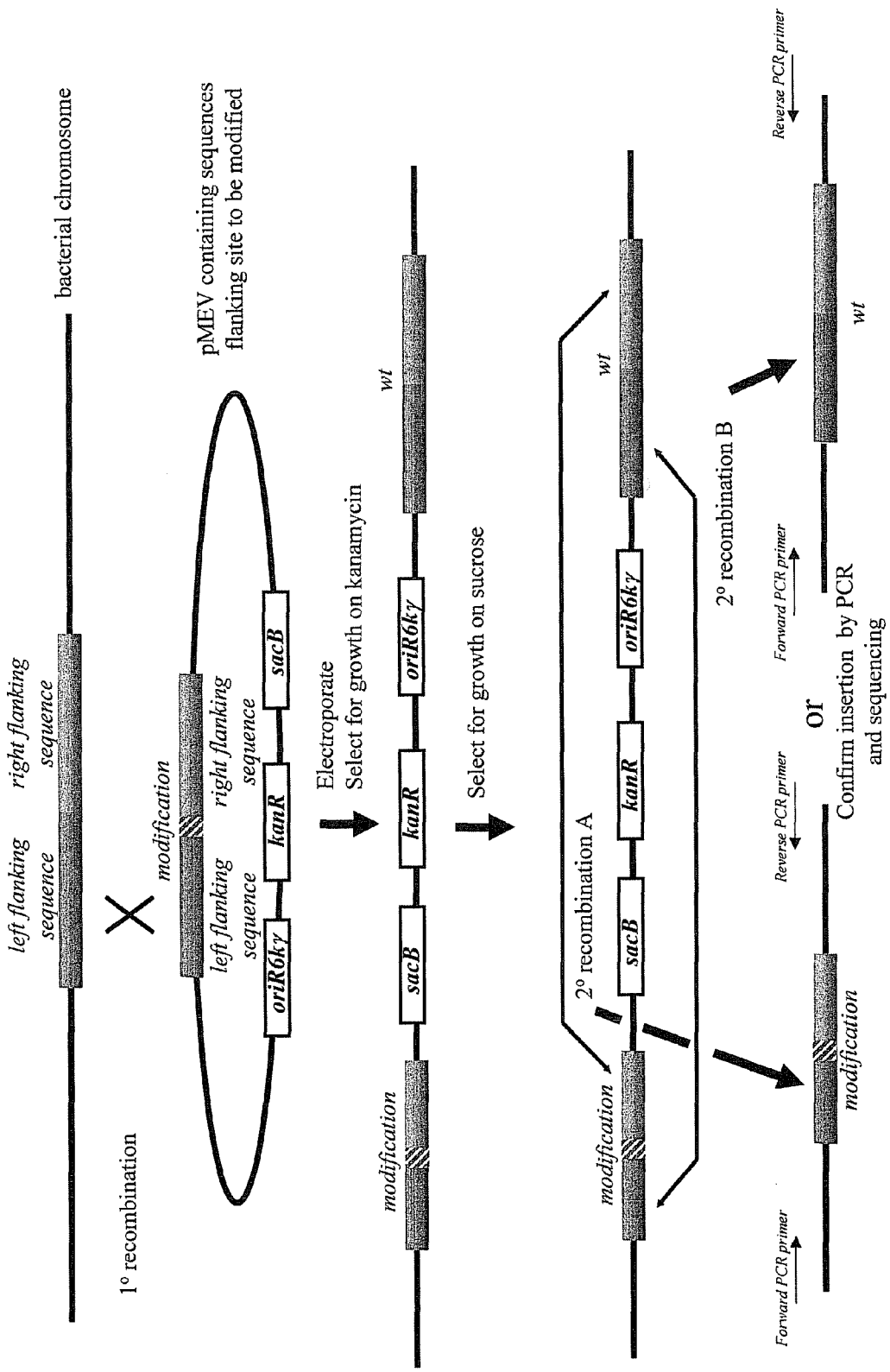
FIG. 12 depicts recombination exchange strategy-modifications. Schematic of steps for generating modifications without leaving behind antibiotic resistance gene or "scar". sacB, sucrose synthase gene; kan, aminoglycoside 3'-phosphotransferase; oriR6k, conditional origin of replication. Modifications could include point mutations, small substitutions, deletions or combinations thereof.
Figure 13:
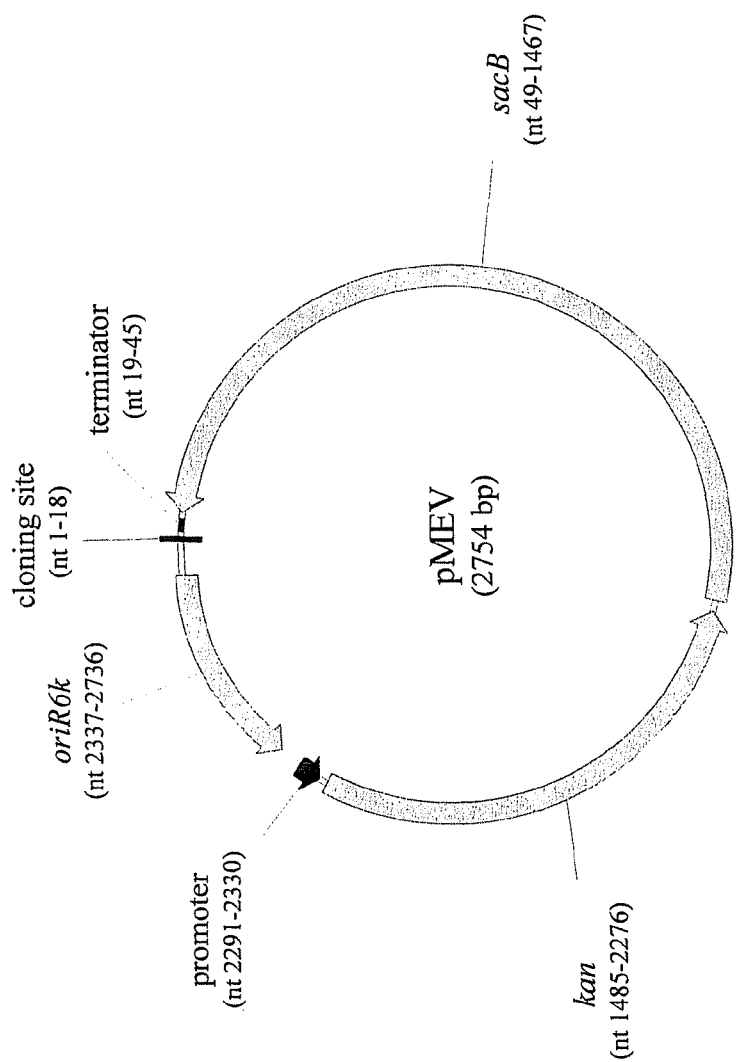
FIG. 13 depicts synthetic vector for modification of strains. Schematic of pMEV vector used for all modifications of E. coli KO11-RD1 and K. oxytoca M5a1. sacB, sucrose synthase gene; kan, aminoglycoside 3'-phosphotransferase; oriR6k, conditional origin of replication.

All chromosomal changes described here were generated using a conventional, i.e., well-known and broadly used, recombinational exchange strategy schematically described in FIGS. 10-12. The vector pMEV, which is used for the manipulation of the gene sequences and introduction of mutations into the chromosome, is described in FIG. 13.

The vector pMEV consists of a conditional origin of replication, oriR6K, a selectable kanamycin resistance gene, kan, and a counter-selectable sucrose synthase gene, sacB. A DNA fragment is cloned into the BbsI site of the vector and replicated in an E. coli host able to recognize the oriR6K conditional origin of replication. The nucleotide sequence of the cloned DNA fragment is verified by sequencing.

The introduction of a change (which can be a deletion, insertion or modification) into the chromosome of the organism involves multiple steps, which are detailed in FIGS. 10-12.

The first step is the electroporation of the pMEV vector containing cloned DNA into the recipient strain and selection for a recombinational co-integration event, which occurs between homologous flanking sequences in the chromosome and recombinant plasmid. The co-integration event results in kanamycin-resistant, bacterial colonies. The recombinational co-integration event can take place between flanking sequences on either side of the change to be introduced. (See FIGS. 10-12, 1° recombination.)

The second step is the removal of the integrated vector sequences by selection for sucrose resistance. The sacB gene on the pMEV vector is a counter-selectable marker that confers sensitivity of a host to sucrose in the growth medium. Sucrose-resistant colonies arise from loss of the entire pMEV vector by a second recombination event between the duplicated homologous sequences (one copy derived from the endogenous chromosome and the second from the introduced sequence). If the recombination takes place between the same flanking sequences relative to the introduced change, the resultant strain "reverts" back to a wild-type strain, identical to the original parent (see FIGS. 10-12, 2° recombination B). If the recombination takes place on the opposite side of the flanking sequence relative to the introduced change, the resultant strain now contains the introduced change in replacement of the wild-type sequence (see FIGS. 10-12, 2° recombination A). These two possible events are determined by PCR amplification of DNA surrounding the putative site of change and verification of the correct change by nucleotide sequencing. Using this method, no pMEV vector sequences remain in the chromosome, and the resulting strain is sensitive to kanamycin. The process can be repeated to introduce additional modifications in the same manner.

Genetic Construction of E. coli SD7

Removal of pdc-adhB-cat from E. coli KO11-RD1

To remove the alcohol operon, consisting of genes encoding the Z. mobilis pyruvate decarboxylase (pdc$^{Zm}$) and alcohol dehydrogenase II (adhB$^{Zm}$) and an associated chloramphenicol acetyltransferase (cat) derived from pBR325 (from E. coli KO11-RD1), a DNA fragment internal to the adhB$^{Zm}$ open reading frame was synthesized by PCR amplification and cloned into pMEV.

Figure 14:
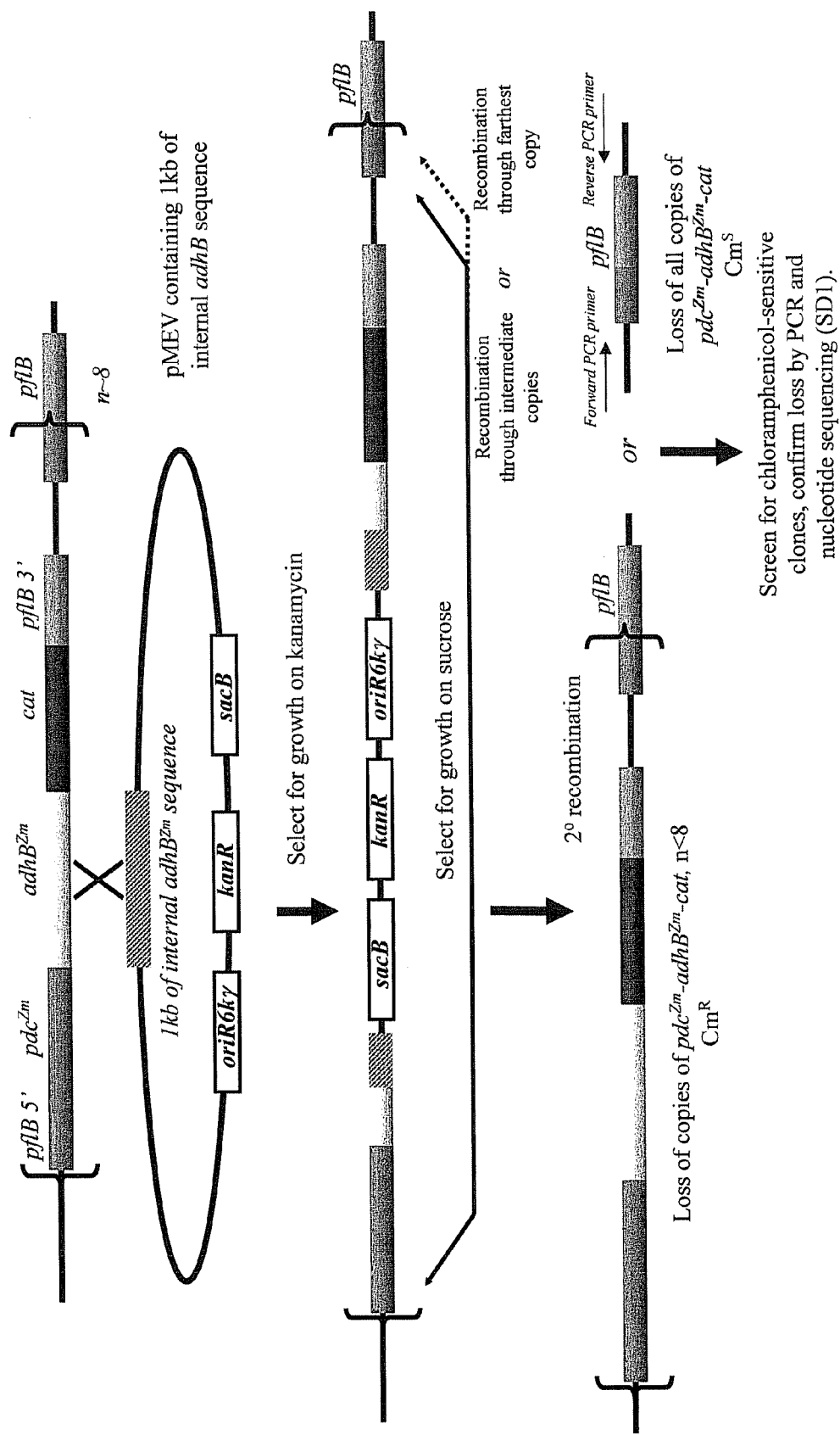
FIG. 14 depicts removal of pdcZm-adhBZm-cat from E. coli KO11-RD1. Variation of recombination exchange method used for removal of tandemly duplicated pdcZm-adhBZm-cat operon, resulting in SD1. Complete removal and restoration of wild-type pflB was confirmed by PCR and nucleotide sequencing

Following the procedure described in FIG. 14, the pMEV-adhB$^{Zm}$ plasmid was used to remove the pdc$^{Zm}$-adhB$^{Zm}$-cat genes from KO11-RD1, by two recombination events with the 2° recombination occurring between the outermost duplicated pflB sequences, selection for sucrose-resistance and screening for chloramphenicol sensitivity. The resultant strain, SD1 was shown to be absent the genes for pdc$^{Zm}$-adhB$^{Zm}$-cat and restored for the wild-type pflB by PCR and nucleotide sequencing.

Deletion of the frdABCD Operon from SD1

The fumarate reductase of E. coli carries out the reductive conversion of fumarate to succinate and represents a side product of fermentation that would be desirable to remove to increase conversion of biomass derived sugars to ethanol (Ohta, K. et al., 1991).

Figure 15:
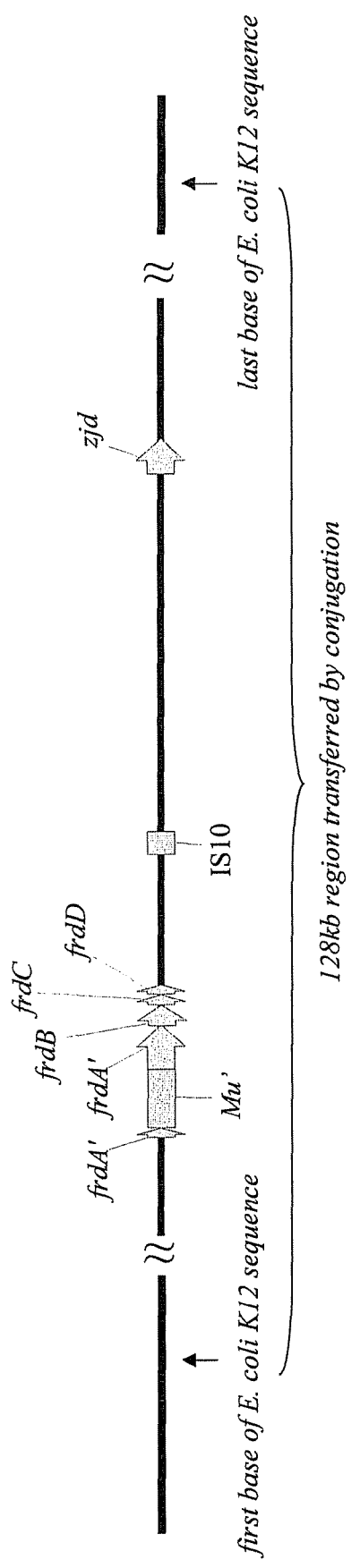
FIG. 15 depicts the configuration of frd mutation and E. coli K12 sequences in E. coli KO11-RD1. Schematic of frd mutation in E. coli KO11-RD1 and E. coli K12 sequences transferred from SE1706 (K12 strain) into KO4 (W strain) during the construction of E. coli KO11-RD1. Mu', remnant of phage Mu responsible for insertional inactivation of frdA in SE1706; IS10, insertion sequence remnant of Tn10 used as marker for conjugational introduction of mutation; zjd, Tn10-associated gene described in genotype of SE1706.

Although the literature describing the construction of E. coli KO11 indicates that the fumarate reductase operon frdABCD has been inactivated by deletion of sequences within the operon, the nucleotide sequence of this region, determined during the course of this work, showed instead that the mutation had arisen by an insertion event in the frdA gene. The inserted sequence (~2196 bp) was found to have been derived from phage Mu, a remnant of sequence used in the original construction of an frd mutation in strain SE1706 (Iuchi, S. et al., 1985). Because Hfr conjugation was used to transfer DNA from SE1706, an E. coli K12 strain, to KO4, an E. coli W strain, K12 sequences in addition to the frd mutation have also been transferred to KO4. FIG. 15 shows the extent of the DNA transferred from SE1706 into KO4, and by extension, residing in KO11-RD1.

Figure 16:
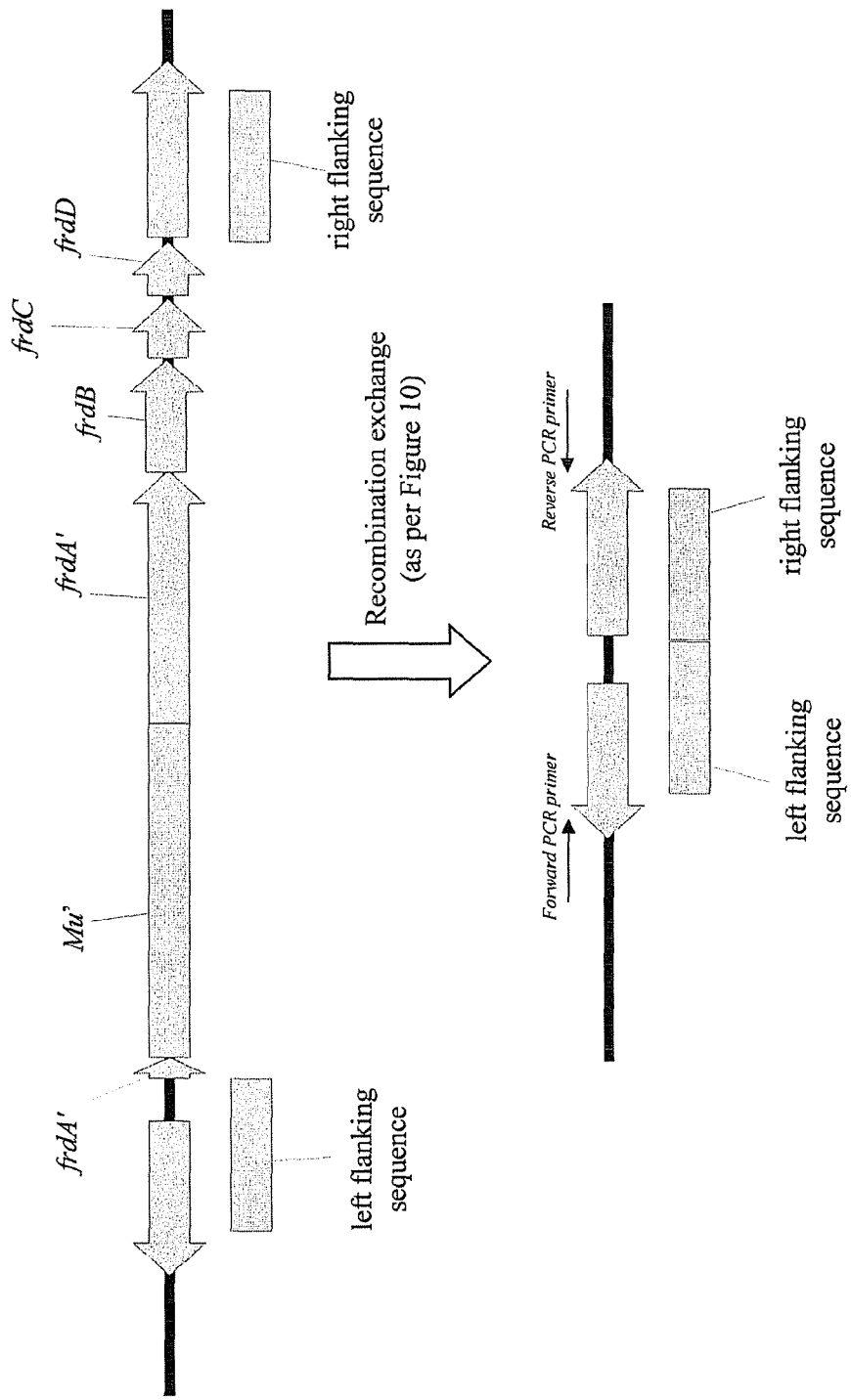
FIG. 16 depicts the deletion of frdABCD from SD1. Schematic of method used to remove frdABCD operon, fumarate reductase genes, and Mu' sequence, resulting in SD2. Deletion was confirmed by PCR and nucleotide sequencing.

To delete the entire frdABCD operon and to remove the remnant sequence of phage Mu, a DNA fragment was designed, synthesized to contain sequences exactly flanking the frdABCD open-reading frames, and cloned in to pMEV. The deletion was introduced, as described in FIG. 16, and verified by PCR and nucleotide sequencing. The resultant strain is SD2.

Deletion of Lactate Dehydrogenase, ldhA, Gene

Figure 17:
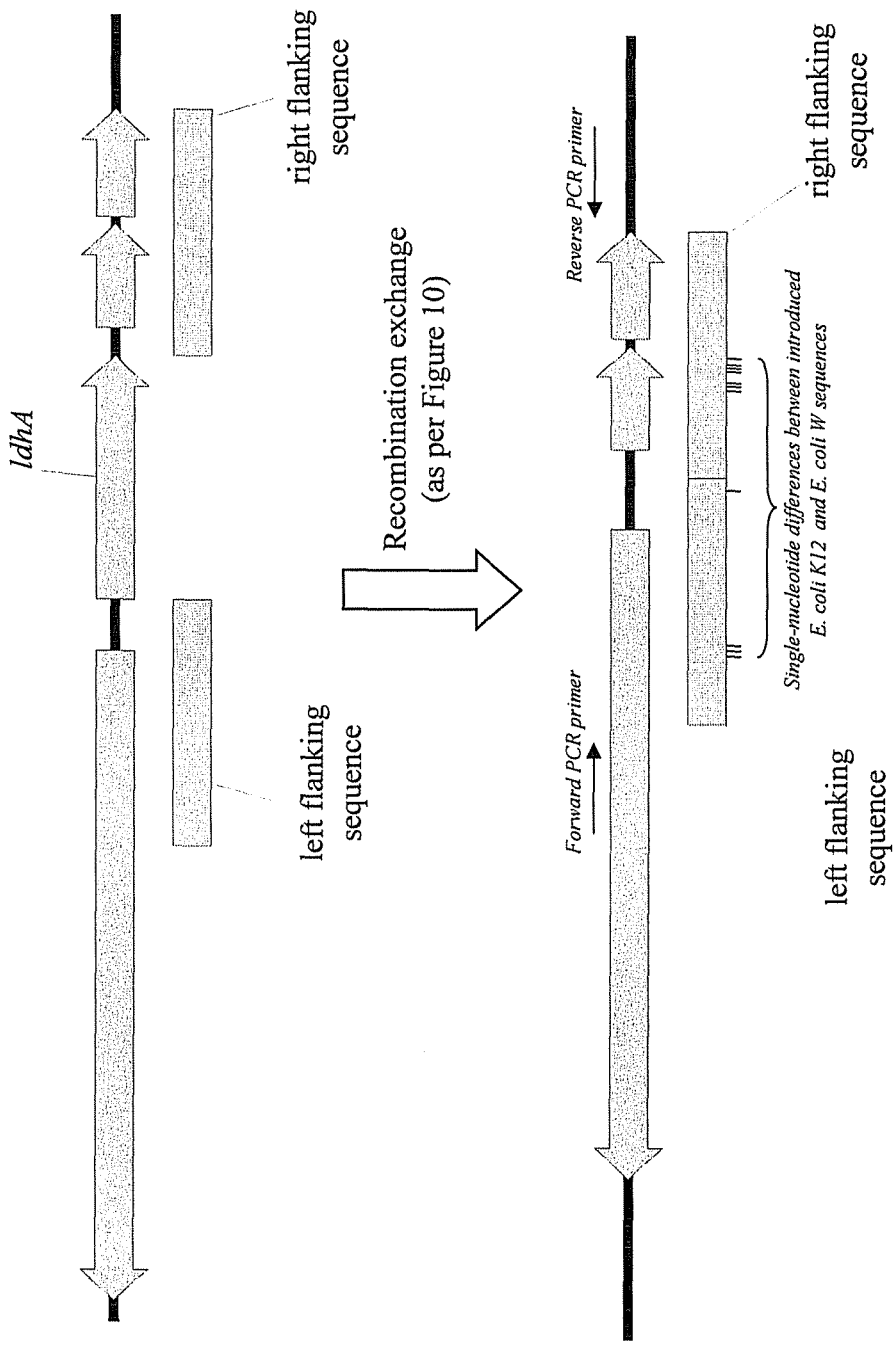
FIG. 17 depicts the deletion of ldhA from SD2. Schematic of method used to remove ldhA, lactate hydrogenase gene, resulting in SD3. Deletion was confirmed by PCR and nucleotide sequencing. Eleven single-nucleotide changes, resulting from the design of the flanking sequences from E. coli K12 genomic DNA, have been introduced into SD3 by recombination. Each of these changes however are silent and do not result in amino acid changes in coding regions.

E. coli and other heterofermentative organisms (defined as producing a variety of fermentation products) can produce lactic acid from sugars by fermentation (August, B. et al., 1996). To remove the ability of this organism to produce lactate as a side-product, a DNA sequence was designed and synthesized to delete the ldhA open-reading frame using E. coli K12 W3110 genome sequence as template. The fragment was cloned into pMEV and the deletion was introduced into the chromosome of SD2, as described in FIG. 17, and was verified by PCR and nucleotide sequencing. Because of the use of E. coli K12 sequence to design the DNA fragment for deletion of ldhA from SD2, the single base changes derived from the E. coli K12 sequence are noted in FIG. 17. None of these changes results in a sequence alteration of the encoded proteins in the corresponding open-reading frames. The resultant strain is SD3.

Introduction of New pdc$^{Ec^o}$-adhA$^{Ec^o}$-adhB$^{Ec^o}$-gfp$^{Ec^o}$ Alcohol Operon into SD3

As the original alcohol operon, pdc$^{Zm}$-adhB$^{Zm}$-cat, in *E. coli* KO11-RD1 had been removed, it was necessary to reintroduce a comparable alcohol operon, absent an antibiotic resistance gene. An operon was designed, composed of an *E. coli* codon-optimized *Z. mobilis* pdc, adhA and adhB gene (indicated as pdc$^{Ec^o}$-adhA$^{Ec^o}$-adhB$^{Ec^o}$). Codon-optimization (indicated as Ec$^o$) resulted in a change in only the nucleotide sequences compared to the native *Z. mobilis* genes but encodes identical amino acid sequences. A second alcohol dehydrogenase gene, adhA was added to the construct to improve conversion of acetaldehyde to ethanol. In addition, an *E. coli* codon-optimized gene for a green fluorescent protein (gfp$^{Ec^o}$) was added to the end of the operon to serve as a reporter for gene expression.

Figure 18:
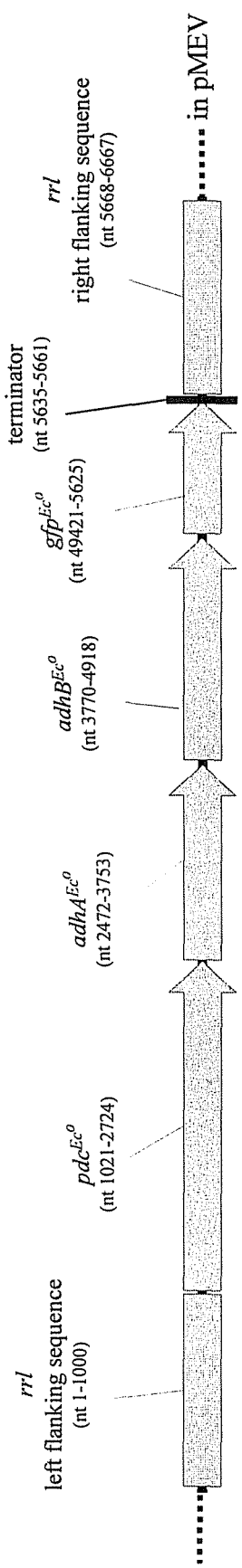
FIG. 18 depicts the construction of pdcEco-adhAEco-adhBEco-gfpEco operon. Alcohol operon composed of E. coli codon-optimized (Eco) Z. mobilis pdc, adhA, adhB and gfp gene sequences with downstream transcriptional terminator, flanked by 23S (rrl) ribosomal gene sequence. Synthetic fragment is cloned into pMEV for introduction into E. coli SD3.

To integrate the newly constructed pdc$^{Ec^o}$-adhA$^{Ec^o}$-adhB$^{Ec^o}$-gfp$^{Ec^o}$ alcohol operon into the chromosome of SD3, sequences of the 23S ribosomal gene (rrl) were chosen to provide homologous sequences flanking the operon. This location was chosen as a site for integration of the alcohol operon because of its documented, high transcription rate (Gourse, R. L. et al., 1996), making it a desirable location to drive the expression of the alcohol genes. A DNA fragment containing the alcohol operon flanked by sequences of the 23S ribosomal gene was cloned into pMEV (see FIG. 18).

Figure 19:
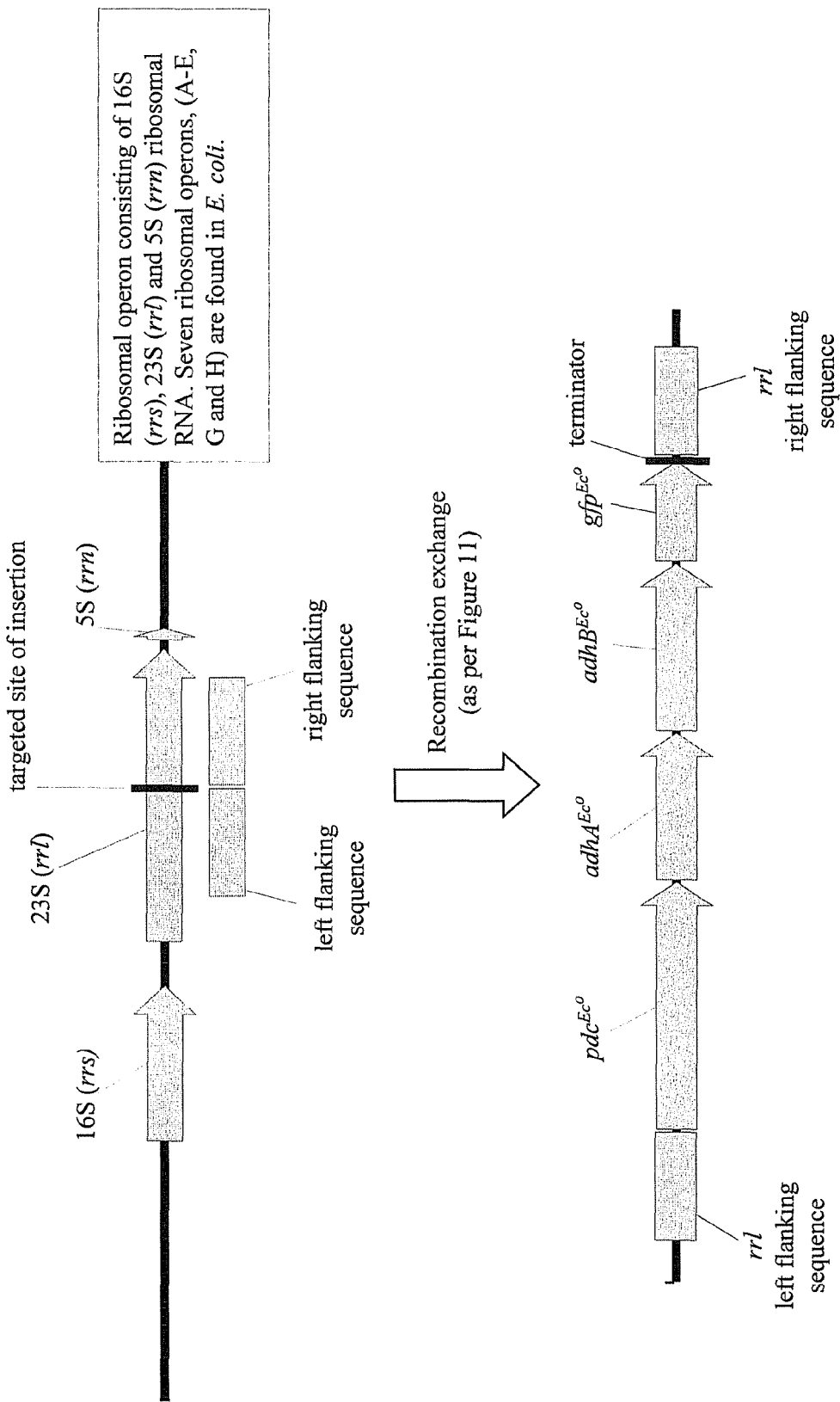
FIG. 19 depicts the insertion of pdcEco-adhAEco-adhBEco-gfpEco operon into SD3. Schematic of strategy for introduction of alcohol operon into the chromosome. The flanking sequences are of sufficient homology to any one of the rrl sequences of the seven E. coli ribosomal operons.
Figure 20:
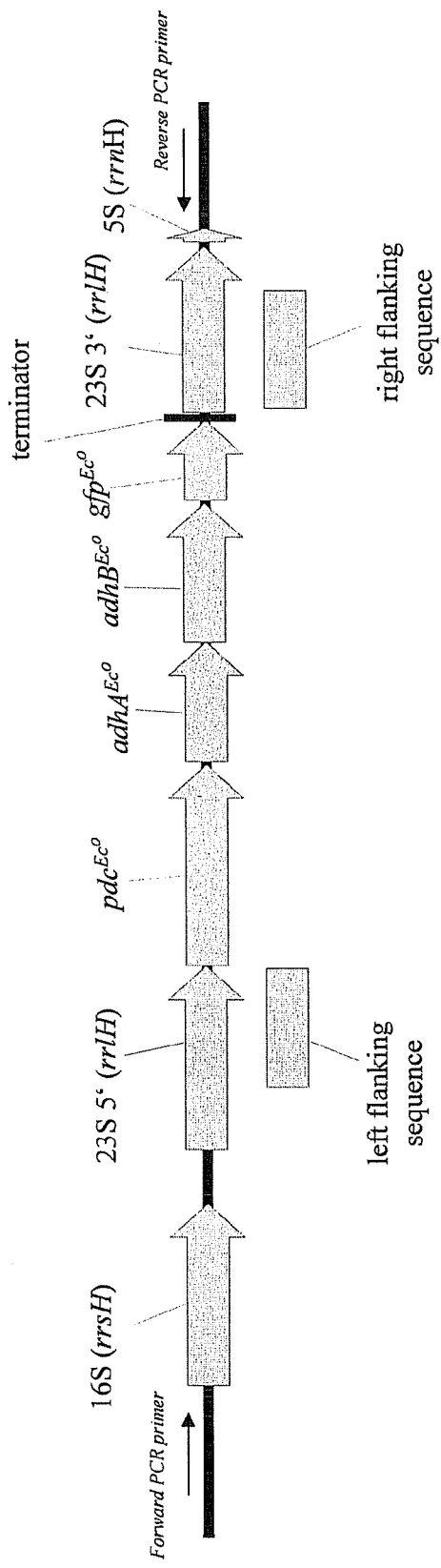
FIG. 20 depicts the location of pdcEco-adhAEco-adhBEco-gfpEco operon inserted in SD3. Integration site of alcohol operon into the ribosomal operon H, determined by PCR and nucleotide sequencing.

As there are seven copies of nearly identical sequence of the 23S ribosomal gene in the *E. coli* genome (rrlA, rrlB, rrlC, rrlD, rrlE, rrlG, and rrlH), the site of initial integration can take place in any one of them. After the first step of integration of the pMEV1-pdc$^{Ec^o}$-adhA$^{Ec^o}$-adhB$^{Ec^o}$-gfp$^{Ec^o}$ plasmid, kanamycin-resistant colonies were selected and assayed for fluorescence due to the expression of the gfp gene. The highest expressing clones were then tested for the ability to ferment xylose to ethanol (xylose was used as substrate because this strain is designed for fermenting pentose sugars from biomass hydrolysate), and the best-performing strain was selected. After selecting the second recombination event by obtaining sucrose-resistant colonies, the complete integration of the new alcohol operon was verified by PCR analysis and nucleotide sequencing. See FIG. 19 for a schematic of the strategy used to introduce the alcohol operon. Sequencing of the region adjacent to the integrated operon showed that the 23S ribosomal gene rrlH was the site of integration (see FIG. 20 for a diagram of the integration location). The resultant strain is SD4.

Deletion of the Wϕ Phage Capsid Protein Gene, gpN

*E. coli* strain W has been described in the literature as containing a lysogenic phage, Wϕ, integrated into its chromosome and capable of producing and releasing phage at a low level ($10^3$-$10^4$ pfu/ml of culture supernatant) that produce plaques on a *E. coli* C indicator strain (Pizer, L. I. et al., 1968). To eliminate the ability of SD4 to produce phage particles that could affect process conditions, a strategy was adopted to eliminate the expression of the major capsid protein by deletion of the encoding gene, gpN. This modification also resulted in a strain that is immune to further infection by Wϕ or related phages due to its retention of phage-encoded immunity genes, (i.e. C1).

Figure 21:
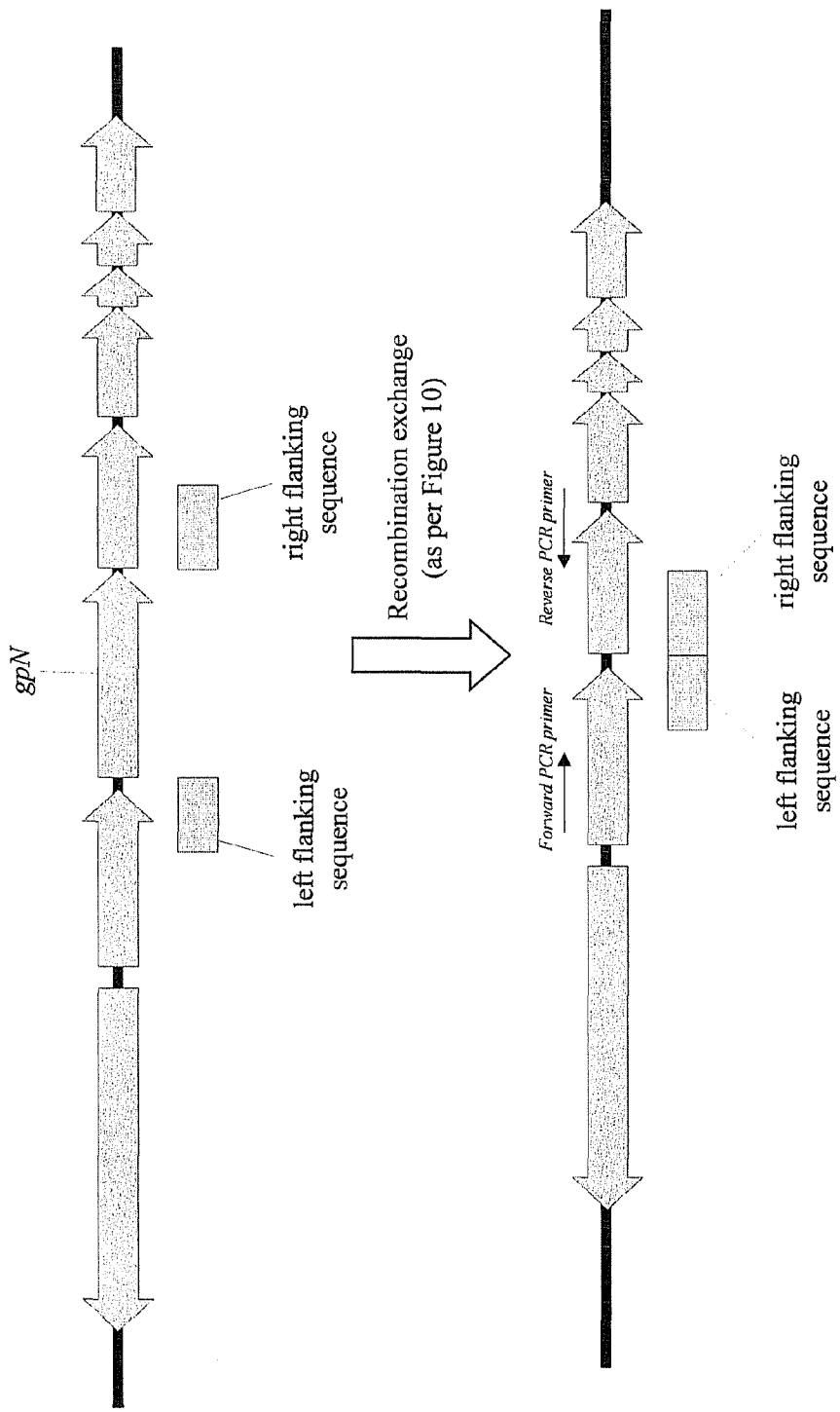
FIG. 21 depicts the deletion of Wf phage major capsid protein gene, gpN from SD4. Schematic of method used to delete Wf major capsid protein gene, gpN. Deletion was confirmed by PCR and nucleotide sequencing.

A fragment of DNA with sequences flanking the open reading frame of gpN was designed from the Wϕ sequence, constructed by PCR and cloned into pMEV. This resultant plasmid was used to construct the gpN deletion in SD4 (see FIG. 21). The deletion was confirmed by PCR and nucleotide sequencing. The resultant strain is *E. coli* SD5. The strain was tested for its ability to produce phage on the indicator strain *E. coli* C and was found to be unable to produce detectable infectious particles. In addition, *E. coli* SD5 was tested based on its known immunity to superinfection with phage produced from *E. coli* W and was found to be resistant, with no plaque formation seen.

Insertion of the *Klebsiella oxytoca* Urease Operon.

To enable *E. coli* SD7 to use urea as an alternative nitrogen source to ammonia or complex nitrogen-containing compounds, the urease operon from *Klebsiella oxytoca* M5A1 was introduced into the chromosome. Urease (urea amidohydrolase, EC3.5.1.5) converts urea into ammonia and carbon dioxide (Mobley and Hausinger, 1989—a review of microbial ureases). The ammonia can then be assimilated through regular nitrogen assimilation pathways. While *E. coli* W does not normally contain this enzyme, many aquatic and soil microorganisms do express ureases, including *Klebsiella oxytoca* M5A1. In one study, urease was found to be expressed by between 17-30% of the cultivated bacteria (Lloyd and Sheaffe, 1973).

The urease operon of *Klebsiella* was first described in a relative of *K. oxytoca, Klebsiella aerogenes*, and consists of seven genes, ureDABCEFG, in a contiguous fragment or operon. The same organization and a high degree of homology at both the nucleotide and protein level (ureD, 78%; UreD, 78%; ureA, 91%; UreA, 97%; ureB, 82%; UreB, 88%; ureC, 85%; UreC, 94%; ureE, 81%; UreE, 87%; ureF, 83%; UreF, 86%; ureG, 87%; UreG; 94%) are seen in *K. oxytoca* M5A1. The urease operon-encoded proteins consist of three structural subunits for the enzyme, UreA, -B and -C, while the remaining four proteins, UreD, -E, -F and -G are required for incorporation of the nickel cofactor of the enzyme (Lee et al, 1992).

Figure 22:
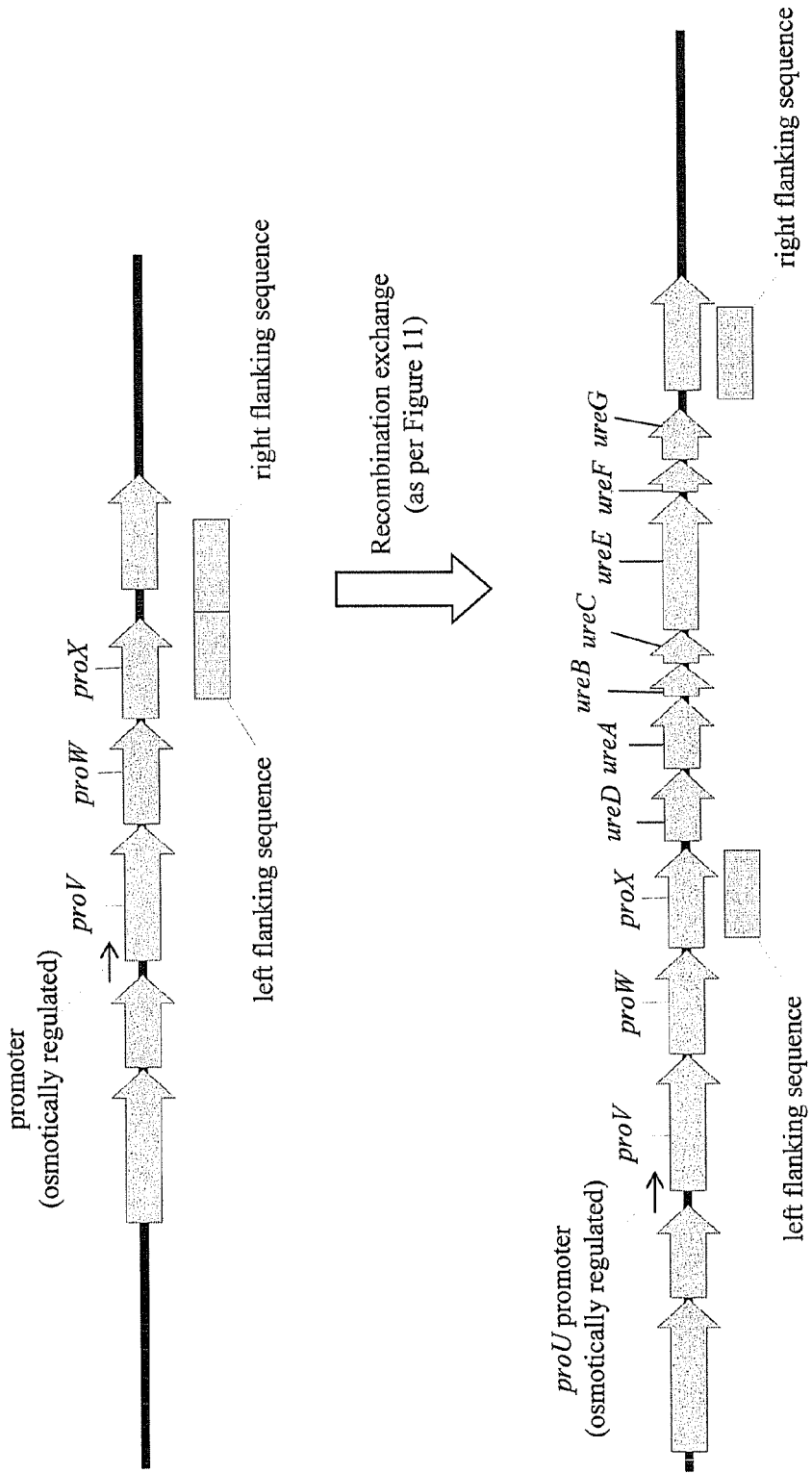
FIG. 22 depicts the insertion of K. oxytoca urease operon into SD5. Schematic of strategy for introduction of urease operon into the chromosome at the proVWX operon. Insertion was confirmed by PCR and nucleotide sequencing.

To introduce the *K. oxytoca* M5A1 urease operon into *E. coli* SD5, a 5 kb PCR product was generated from *K. oxytoca* M5A1 chromosomal DNA and ligated into a plasmid consisting of the pMEV vector and flanking *E. coli* W sequences from the downstream end of the pro VWX operon. This operon is regulated by osmotic conditions (Lucht and Bremer, 2006) and has been found to be able to similarly regulate the express of heterologous genes (Herbst et al, 1994). The constructed plasmid was used to introduce the urease operon into *E. coli* SD6 (see FIG. 22). The successful introduction was confirmed by PCR and nucleotide sequencing. The resultant strain was *E. coli* SD6.

Deletion of the Methylglyoxal Synthase Gene, mgsA.

Figure 23:
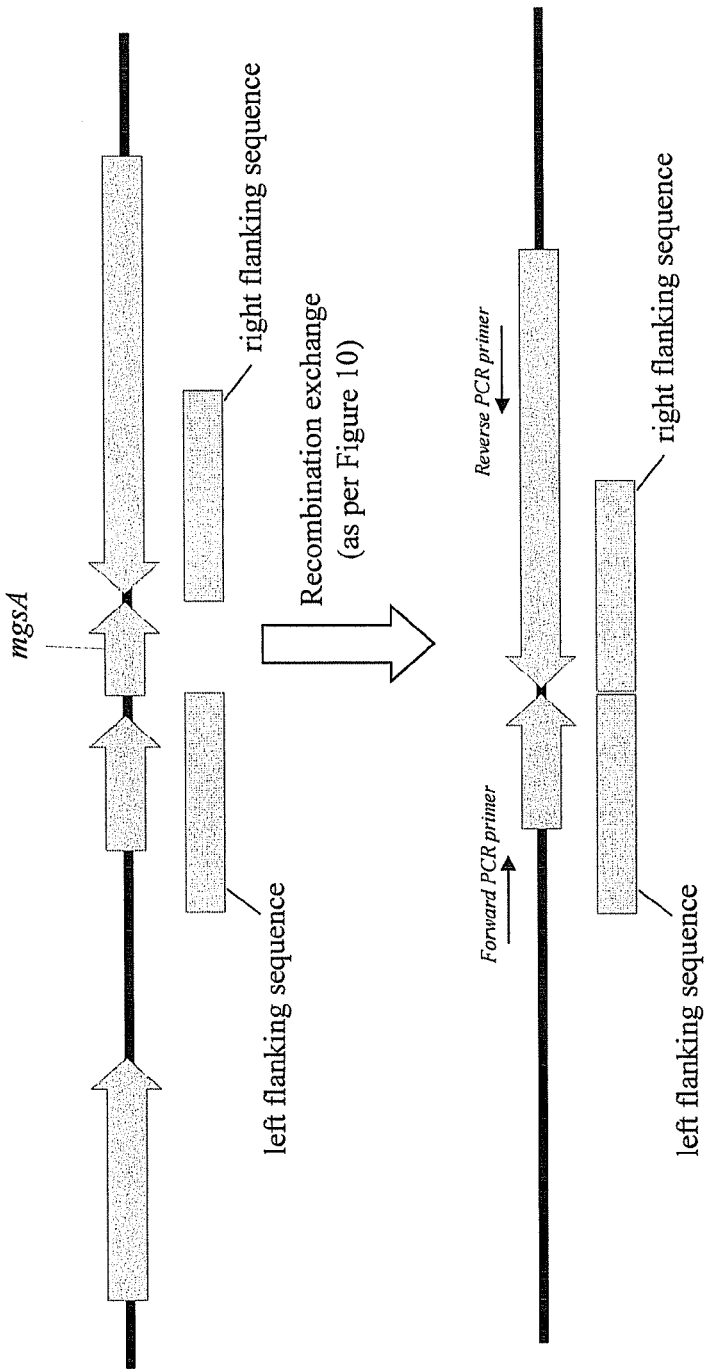
FIG. 23 depicts the deletion of mgsA from E. coli W. Schematic of method used to remove mgsA, methylglyoxal synthase gene, resulting in SD7. Deletion was confirmed by PCR and nucleotide sequencing.

The utilization of sugars by bacteria is subject to metabolic control mechanisms that insure a proper flux through glycolysis and the prevention of an imbalance in reducing equivalents and high energy phosphate bonds. One documented control mechanism is the methylglyoxal bypass (Russell and Cook, 1995), which serves to reduce intracellular ATP concentrations which result from exposure of bacteria to high sugar concentrations and inability to balance the flux of energy and carbon through anabolic and catabolic metabolism. The effect of the methylglyoxal pathway is to discharge excess ATP resulting in the production of methylglyoxal from dihydroxyacetone phosphate. Methylglyoxal, however, is a reactive aldehyde and can inhibit the growth and reduce survival of the cell if it is not further metabolized (Booth et al, 2003; Grabar et al, 2006). To eliminate the production of methylglyoxal and the resulting non-fermentative metabolic product lactate, the methylgloxal synthase gene, mgsA, was deleted from SD6 using the method described in FIG. 23. A region of the *E. coli* W genome sequence flanking the mgsA open reading frame was used to design and synthesize a DNA fragment that was then cloned into pMEV. The deletion was introduced and confirmed by PCR analysis and DNA sequencing. The resultant strain is SD7.

Example 3

Construction of Ethanologenic Strain Starting from E. Coli W

Figure 27:
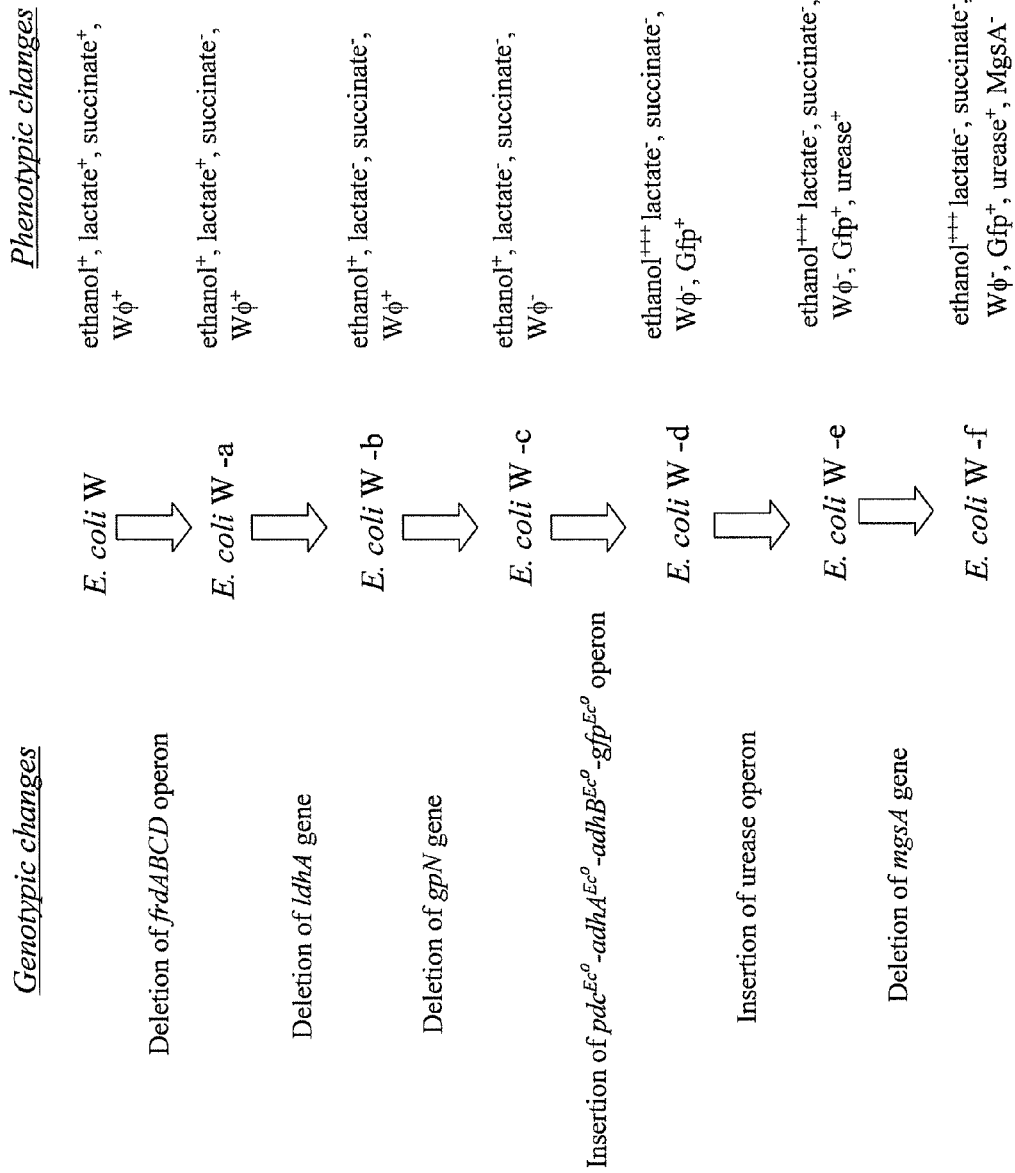
FIG. 27 depicts an exemplary method for making a bacterium of the invention starting with *E. coli* W. Wf, ability to make viable Wf phage. Gfp, green fluorescent protein. The gene deletions and insertions depicted can be carried out in any order.

The following prophetic example describes the production of an ethanologenic strain of the invention starting directly with E. coli W. Although the steps are described in a particular order herein, one of ordinary skill in the art understands that the order the steps are preformed does not effect the final strain, and therefore the genetic modification described below can be done in any order. The genetic modifications set forth in this example are schematically represented in FIG. 27.

Starting with E. coli W, genetic changes are made to one or more genes from the frdABCD operon resulting in decreased expression of these one or more genes. Genetic modifications are made to the resulting strain to decrease the expression of the ldhA gene.

The phN gene is optionally modified to decrease the expression of this gene.

Genes are added to the resulting bacterium to increase the production of ethanol. pdc can be added alone, or in combination with adhA and/or adhB.

One or more genes from the urease operon are added. At least ureA, B and C are added to the bacterium. Optionally, ureD, E and/or F are added to the bacterium.

The last genetic modification that will be made to the bacterium will a modification to decrease the expression of the msgA gene.

The modifications described above will produce an E. coli strain that is ethanol+++ lactate–, succinate–, Wf–, Gfp+, urease+, MgsA–.

It is understood by those of skill in the art that modification that decrease expression of a gene can be complete gene deletion, partial gene deletions, frameshift modification, etc. that result in decreased expression of the target gene.

Example 4

Ethanol Production by E. coli SD7

This example provides data on the ethanol production by Escherichia coli SD7. The example also provides methods for the production of fermentation broth, analyzing organic acid levels, and for studying heat and chemical inactivation procedures for E. coli SD7.

Materials and Methods

Two 1.9 L BioFlo fermentation runs of E. coli SD7 were conducted. The broth was subsequently recovered for further testing.

Time point was taken at pre-inoculation, post-inoculation, 4, 19.1, 24, 28, 43.4, and 48 hours. The fermentation process is initiated when a vial of frozen glycerol working cell-bank suspension of the bacteria is thawed and approximately 100 μL is inoculated into one seed I flask, consisting of 100 mL of medium in a 250 mL flask. The seed I flask is incubated on a controlled-temperature (35° C.) shaker shaking at 120 rpm for exactly 11 hours. The seed I flask is then used to inoculate a 400 mL seed culture (as seed culture for 1.9 L production fermentations).

For the seed II flask, 0.4 mL from the seed I flask stage is aseptically used to inoculate 400 mL of medium in a 1 L seed II flask. The seed flask is incubated on a controlled-temperature (35° C.) shaker shaking at 120 rpm for exactly 8 hours, and production fermentor is inoculated.

The main fermentation consists of the initial batch fermentation medium containing AM6 medium, defoamer, and over-limed hydrolysate and the added seed inocula (95 mL). Upon reaching 3.9 hours, the fed-batch model is initiated by setting the feed rate of over-limed spiked hydrolysate feed solution to 2.12 mL/min and AM6 feed to 0.029 mL/min. Agitation cascade limits are set to 200-1000 RPM. Aeration is constant at 60 mL/min. Dissolved oxygen concentration is maintained at 30% by increasing the agitation as the DO drops below the set point of 30%. As DO concentration rises above the set point of 30%, agitation decreases to reduce the DO available in the bulk liquid. Over time the oscillations decrease and DO concentration is maintained at 30%. Integral gain in our NBS system is 0.15 and proportional gain is set to 0.05 (these control the rate at which the agitation changes to the DO concentration).

After termination at 48 hrs, culture broth was harvested for genetic identity and inactivation studies.

Results and Conclusions

Figure 24:
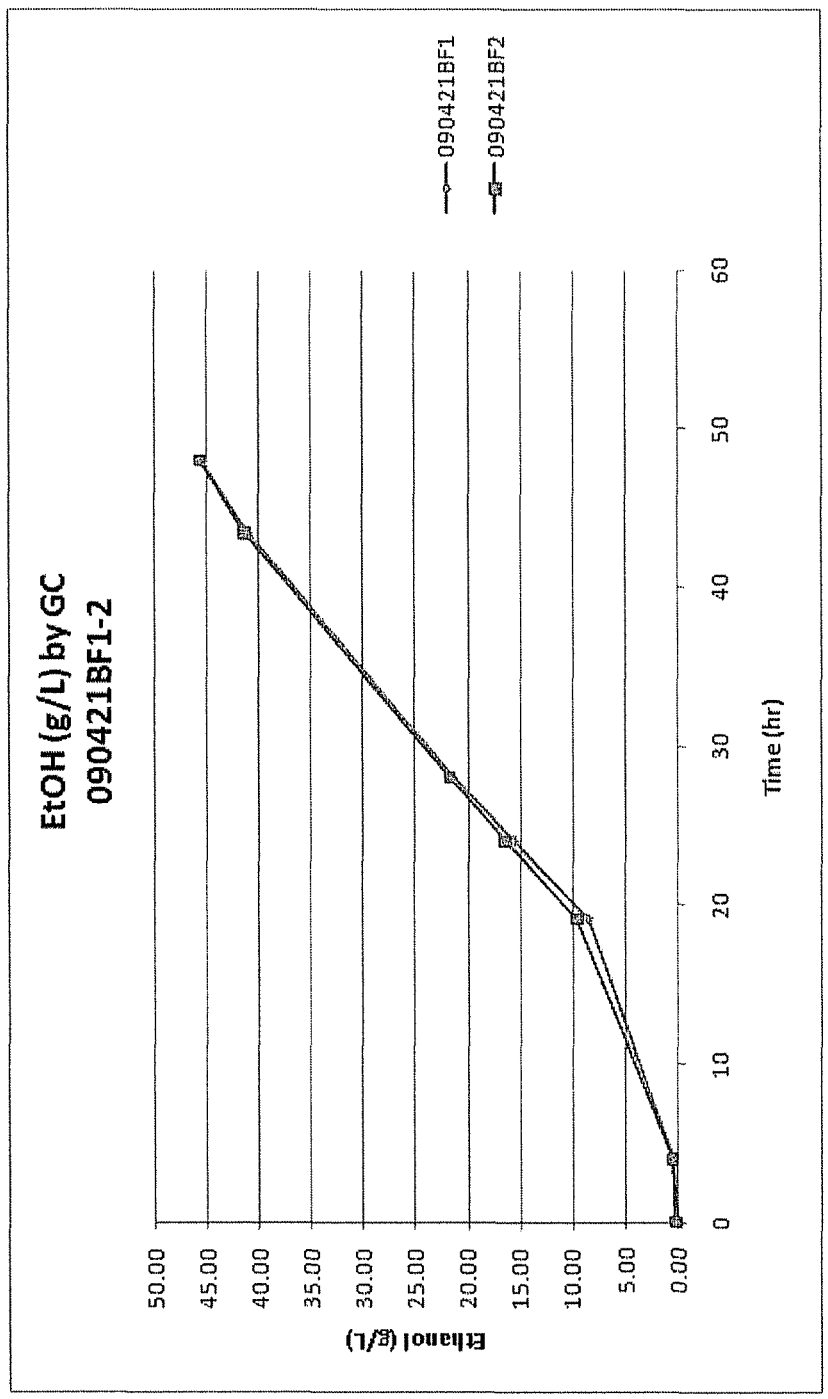
FIG. 24 depicts ethanol concentration in fermentation broth during E. coli SD7 fed-batch fermentation.
Figure 25:
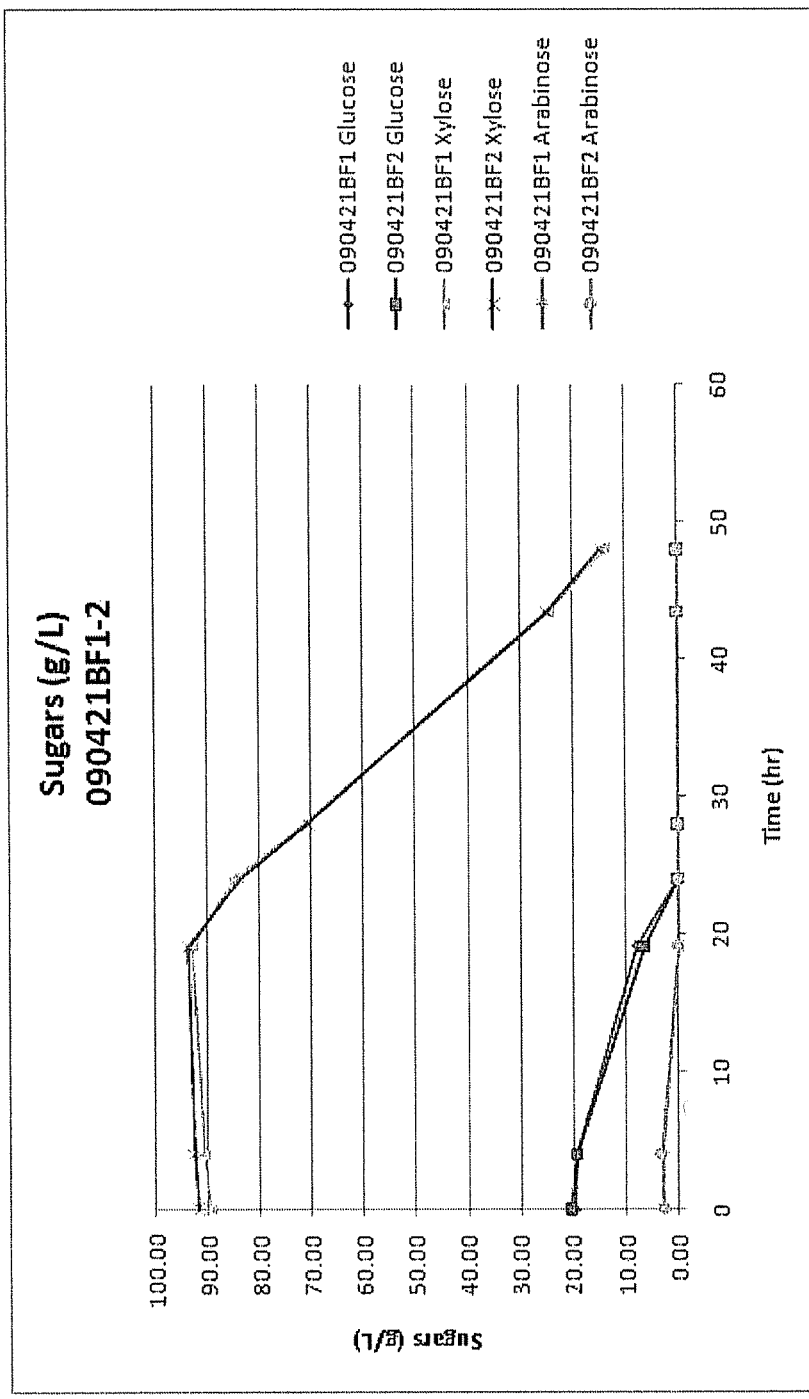
FIG. 25 depicts xylose, arabinose, and glucose concentrations in fermentation broth during E. coli SD7 fed-batch fermentation.
Figure 26:
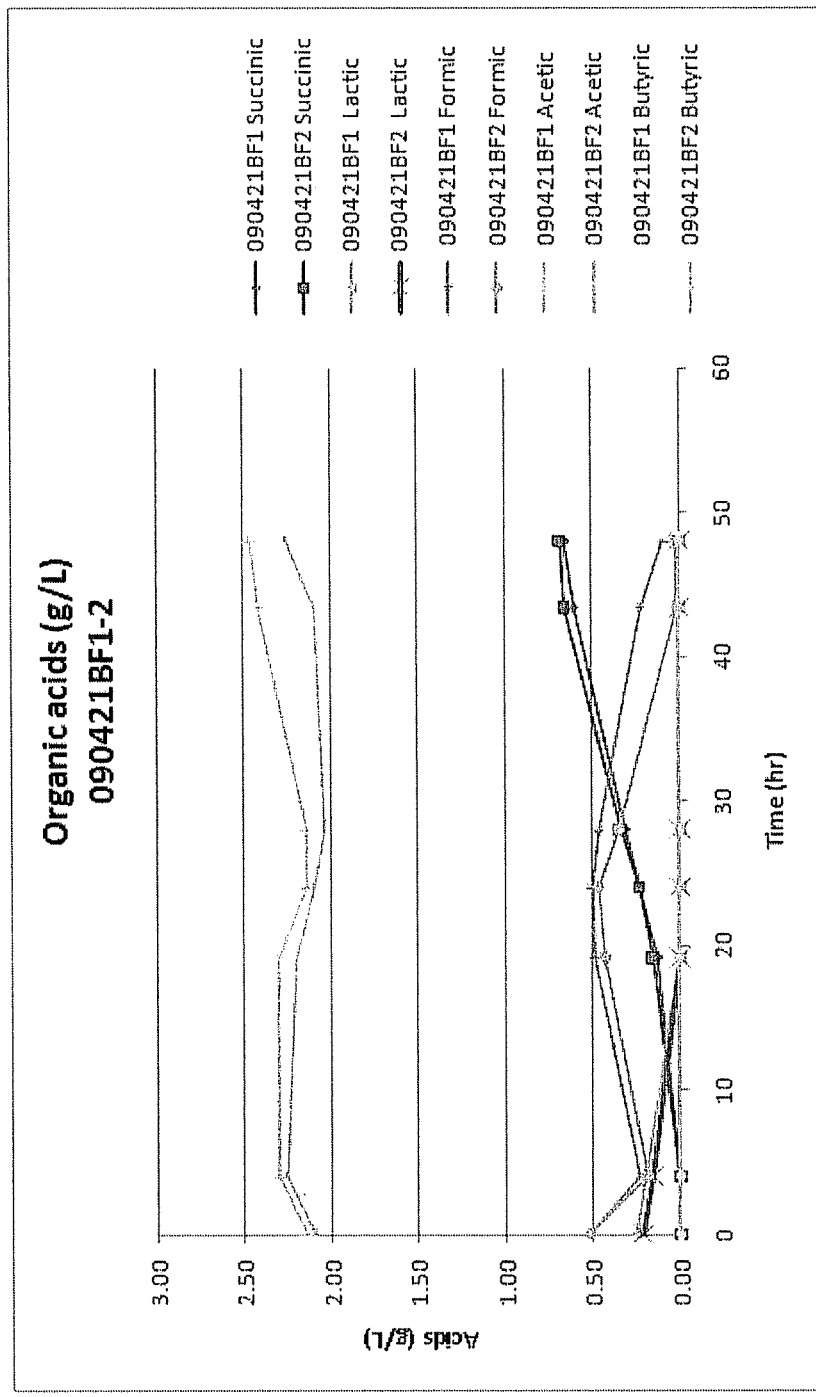
FIG. 26 depicts succinic, lactic, formic, acetic, and butyric acid concentrations in fermentation broth during *E. coli* SD7 fed-batch fermentation.

FIGS. 24-26 show the time course profiles for the major reactants and products for the E. coli SD7 fed-batch fermentation. During the course of the fermentation, the organism uptakes xylose, arabinose, and glucose and metabolizes them into biomass, ethanol, and organic acids. Some organic acids are present in the initial media and the feed bottle. These organic acids may result in an increase in the concentration (when the feed bottle has a higher concentration than the initial media) or in a decrease in concentration (when the feed bottle has a lower concentration than the initial media). The ethanol and sugar data show that the organisms consumed sugars and produced ethanol.

LIST OF REFERENCES

American Water Works Association 9221 Multiple-Tube fermentation technique for members of the coliform group, in *Standard Methods for the Examination of Water and Wastewater*, 19 ed., Eaton, A. D., Clesceri, L. S., and Greenberg, A. E., editors; American Public Health Association: Washington, D.C., Chapter 9, pp. 44-52 (1995).

Asghari, A., Bothast, R. J., Doran, J. B., and Ingram, L. O. *Ethanol production from hemicellulose hydrolysates of agricultural residues using genetically engineered Escherichia coli strain KO11*. Journal of Industrial Microbiology 16, pp. 42-47 (1996).

ATCC Bacteria ATCC number: 11105 Website, Last Accessed Aug. 21, 2007, Available from: www.atcc.org/common/catalog/numsearch/numresults.cfm?atccnum=11105

ATCC Bacteria ATCC Number: 9637 Website, Last Accessed Jul. 9, 2007, Available from: www.atcc.org/ATCCAdvancedCatalogSearch/tabid/112/Default.aspx August, B. and Sawers, G Fermentation, in *Escherichia coli and Salmonella*: cellular and molecular biology, 2nd ed., August, B., Cutriss III, R., Kaper, J. B., Neidhardt, F., Nystorm, T., Rudd, K. E., and Squires, C. L., editors; ASM Press: Washington, D.C., Chapter 18, (1996). [Online] www.ecosal.org.

Bagley, S. T. *Habitat association of Klebsiella species*. Infect. Control 6, pp. 52-58 (1985).

Brenner, D. Introduction to the Family Enterobacteriaceae, in *The Prokaryotes a handbook on the biology of bacteria: ecophysiology, isolation, identification, applications*, Balows, A., editors; Springer-Verlag: New York, Chapter 141, pp. 2673-2695 (1992).

Brenner, D., Krieg, N. R., and Staley, J. T. *Bergey's Manual of Systematic Bacteriology*, Second ed. Springer: New York, p. 685 (2005a).

Brenner, D., Krieg, N. R., and Staley, J. T. *Bergey's Manual of Systematic Bacteriology*, Second ed. Springer: New York, p. 693 (2005b).

Brenner, D. J., Farmer, J. J. I., Hickman, F. W., Asbury, M. A., and Steigerwalt, A. G. *Taxonomic and Nomenclature Changes in Enterobacteriaceae.* HEW Publication No. (CDC) 79-8356, Atlanta, (1979).

Burkholder, P. R. *Determination of vitamin B12 with a mutant strain of Escherichia coli.* Science 114, pp. 459-460 (1951).

Cali, B. M., Micca, J. L., and Stewart, V. *Genetic regulation of nitrate assimilation in Klebsiella pneumoniae M5a1.* J. Bacteriol. 171, pp. 2666-2672 (1989).

Canchaya, C., Fournous, G., Chibani-Chemoufi, S., Dillmann, M. L., and Brussow, H. *Phage as agents of lateral gene transfer.* Curr. Opin. Microbiol. 6, pp. 417-424 (2003).

Cannon, M., Cannon, F., Buchanan-Wollaston, V., Ally, D., Ally, A., and Beynon, J. *The nucleotide sequence of the nifJ gene of Klebsiella pneumoniae.* Nucleic Acids Res. 16, p. 11379 (1988).

Casjens, S. *Prophages and bacterial genomics: what have we learned so far?* Mol. Microbiol. 49, pp. 277-300 (2003).

Chai, W. and Stewart, V. *NasR, a novel RNA-binding protein, mediates nitrate-responsive transcription antitermination of the Klebsiella oxytoca M5a1 nasF operon leader in vitro.* J. Mol. Biol. 283, pp. 339-351 (1998).

Chai, W. and Stewart, V. *RNA sequence requirements for NasR-mediated, nitrate-responsive transcription antitermination of the Klebsiella oxytoca M5a1 nasF operon leader.* J. Mol. Biol. 292, pp. 203-216 (1999).

Convention on Biological Diversity Cartagena Protocol on Biosafety to the Convention on Biological Diversity Website, Last Accessed Jan. 31, 2008, Available from: www.cbd.int/doc/legal/cartagena-protocol-en.pdf Davis, B. D. *The Isolation of Biochemically Deficient Mutants of Bacteria by Means of Penicillin.* Proc. Natl. Acad. Sci. U.S.A. 35, pp. 1-10 (1949).

Davis, B. D. and MINGIOLI, E. S. *Mutants of Escherichia coli requiring methionine or vitamin B12.* J. Bacteriol. 60, pp. 17-28 (1950).

Diaz, E., Ferrandez, A., Prieto, M. A., and Garcia, J. L. *Biodegradation of aromatic compounds by Escherichia coli.* Microbiol. Mol. Biol. Rev. 65, pp. 523-569 (2001).

Dixon, R., Cannon, F., and Kondorosi, A. *Construction of a P plasmid carrying nitrogen fixation genes from Klebsiella pneumoniae.* Nature 260, pp. 268-271 (1976).

Eady, R. R., Smith, B. E., Cook, K. A., and Postgate, J. R. *Nitrogenase of Klebsiella pneumoniae. Purification and properties of the component proteins.* Biochem. J. 128, pp. 655-675 (1972).

Eblen, D. R., Annous, B. A., and Sapers, G. M. *Studies to select appropriate nonpathogenic surrogate Escherichia coli strains for potential use in place of Escherichia coli O157: H7 and Salmonella in pilot plant studiest.* J. Food Prot. 68, pp. 282-291 (2005).

Francetic, O., Marjanovic, N., and Glisin, V. *Molecular biology of penicillin acylase genes.* Biotecnologie April, pp. 11-15 (1988).

Freeman, G. G. *The fermentation of sucrose by Aerobacter aerogenes.* Biochem. J. 41, pp. 389-398 (1947).

Gourse, R. L., Gaal, T., Bartlett, M. S., Appleman, J. A., and Ross, W. *rRNA transcription and growth rate-dependent regulation of ribosome synthesis in Escherichia coli.* Annu. Rev. Microbiol. 50, pp. 645-677 (1996).

Hamilton, P. B. and Wilson, P. B. Nitrogen Fixation by *Aerobacter aerogenes*, in *Biochemistry of Nitrogen*, Suomalainen Tiedeakatemia: Helsinki, pp. 139-150 (1955).

Hamilton-Miller, J. M. *Penicillinacylase.* Bacteriol. Rev. 30, pp. 761-771 (1966).

Herbst, B., Knep, S., and Bremer, E. *pOSEX: vectors for osmotically controlled and finely tuned gene expression in E. coli.* Gene. 151, pp. 137-142 (1994).

Holt, J. G, Krieg, N. R., Sneath, P. H. A., Staley, J. T., and William, S. T. *Bergey's manual of determinative bacteriology,* 9th ed. Baltimore, Md.; London: Lippincott Williams and Wilkins: p. 181 (1994a).

Holt, J. G., Krieg, N. R., Sneath, P. H. A., Staley, J. T., and William, S. T. *Bergey's manual of determinative bacteriology,* 9th ed. Baltimore, Md.; London: Lippincott Williams and Wilkins: p. 210 (1994b).

Holt, J. G., Krieg, N. R., Sneath, P. H. A., Staley, J. T., and William, S. T. *Bergey's manual of determinative bacteriology,* 9th ed. p. 179 (1994c).

International Food Biotechnology Council Chapter 4: *Safety evaluation of foods and food ingredients derived from microorganisms.* Regul. Toxicol. Pharmacol. 12, p. S114-S128 (1990).

Invitrogen One Shot® Mach1™-T1® Chemically Competent *E. coli* Website, Last Accessed Aug. 21, 2007, Available from: www.invitrogen.com/content/sfs/manuals/oneshot_mach1_man.pdf Iuchi, S., Kuritzkes, D. R., and Lin, E. C. *Escherichia coli mutant with altered respiratory control of the frd operon.* J. Bacteriol. 161, pp. 1023-1028 (1985).

Jarboe, L. R., Grabar, T. B., Yomano, L. P., Shanmugan, K. T., and Ingram, L. O. *Development of ethanologenic bacteria.* Adv. Biochem. Eng Biotechnol. 108, pp. 237-261 (2007).

Kirschstein, R. L. *Notice of final action under the NIH Guidelines for Research Involving Recombinant DNA Molecules (NIH Guidleines).* Federal Register 66, pp. 64051-64052 (2001a).

Kirschstein, R. L. *Notice of proposed actions under the NIH Guidlelines for Research Involving Recombinant DNA Molecules (NIH Guidelines).* Federal Register 66, pp. 42555-42556 (2001b).

Lai, X., Davis, F. C., Hespell, R. B., and Ingram, L. O. *Cloning of cellobiose phosphoenolpyruvate-dependent phosphotransferase genes: functional expression in recombinant Escherichia coli and identification of a putative binding region for disaccharides.* Appl. Environ. Microbiol. 63, pp. 355-363 (1997).

Le Rudulier, D., Yang, S. S., and Csonka, L. N. *Nitrogen fixation in Klebsiella pneumoniae during osmotic stress. Effect of exogenous proline or a proline overproducing plasmid.* Biochim Biophys. Acta 719, pp. 273-283 (1982).

Lee, M. H., Mulrooney, S. B., Renner, M. J., Markowicz, Y., and Hausinger, R. P. *Klebsiella aerogenes urease gene cluster: sequences of ureD and demonstration that four accessory genes (ureD, ureF and ureG) are involved in nickel metallocenter biosynthesis.* J. Bacteriol. 174, pp. 4324-4330 (1992).

Lin, J. T., Goldman, B. S., and Stewart, V. *Structures of genes nasA and nasB, encoding assimilatory nitrate and nitrite reductases in Klebsiella pneumoniae M5a1.* J. Bacteriol. 175, pp. 2370-2378 (1993).

Lloyd, A. B., and Sheaffe, M. J. *Urease activity in soils.* Plant Soil. 39, pp. 71-80 (1973).

Lucht, J. M., and Bremer, E. *Adaptation of Escherichia coli to high osmolarity environments:osmoregulation of the high affinity glycine-betaine transport system ProU.* FEMS Microbiol. Rev. 14, pp. 3-20 (2006)

MacNeil, D., Zhu, J., and Brill, W. J. *Regulation of nitrogen fixation in Klebsiella pneumoniae: isolation and characterization of strains with nif-lac fusions*. J. Bacteriol. 145, pp. 348-357 (1981).

MacNeil, T., MacNeil, D., Roberts, G. P., Supiano, M. A., and Brill, W. J. *Fine-structure mapping and complementation analysis of nif (nitrogen fixation) genes in Klebsiella pneumoniae*. J. Bacteriol. 136, pp. 253-266 (1978).

Mahl, M. C., Wilson, P. W., Fife, M. A., and Ewing, W. H. *Nitrogen fixation by members of the tribe Klebsielleae*. J. Bacteriol. 89, pp. 1482-1487 (1965).

Mobley, H. L. T., and Hausinger, R. P. *Microbial ureases: significance, regulation and molecular characterization*. Microbiol. Rev. 53, pp. 85-108 (1989).

Muhldorfer, I., Blum, G, Donohue-Rolfe, A., Heier, H., Olschlager, T., Tschape, H., Wallner, U., and Hacker, J. *Characterization of Escherichia coli strains isolated from environmental water habitats and from stool samples of healthy volunteers*. Res. Microbiol 147, pp. 625-635 (1996).

NIH *Notice of Actions Under the NIH Guidelines for Research Involving Recombinant DNA Molecules*. Federal Register 55, p. 7438 (1990).

NIH *NIH Guidelines For Research Involving Recombinant DNA Molecules* Website, Last Accessed Jul. 25, 2006, Available from: www4.od.nih.gov/oba/rac/guidelines-02/NIH_Guidelines_Apr-02.htm OECD Safety Evaluation of Foods Derived by Modern Biotechnology Concepts and Principles Organization for Economic Co-operation and Development, Website, Last Accessed Mar. 13, 2007, Available from: www.oecd.org/dataoecd/57/3/1946129.pdf Ohta, K., Beall, D. S., Mejia, J. P., Shanmugam, K. T., and Ingram, L. O. *Genetic improvement of Escherichia coli for ethanol production: chromosomal integration of Zymomonas mobilis genes encoding pyruvate decarboxylase and alcohol dehydrogenase II*. Appl Environ. Microbiol 57, pp. 893-900 (1991).

Pariza, M. W. and Foster, E. M. *Determining the safety of enzymes used in food processing*. Journal of Food Protection 46, pp. 453-468 (1983).

Pariza, M. W. and Johnson, E. A. *Evaluating the safety of microbial enzyme preparations used in food processing: update for a new century*. Regul. Toxicol. Pharmacol. 33, pp. 173-186 (2001).

Pengra, R. M. and Wilson, P. W. *Physiology of nitrogen fixation by Aerobacter aerogenes*. J. Bacteriol. 75, pp. 21-25 (1958).

Pizer, L. I., Smith, H. S., Miovic, M., and Pylkas, L. *Effect of prophage Won the propagation of bacteriophages T2 and T4*. J. Virol. 2, pp. 1339-1345 (1968).

Read, R. B., Jr., Schwartz, C., and Litsky, W. *Studies on thermal destruction of Escherichia coli in milk and milk products*. Appl. Microbiol. 9, pp. 415-418 (1961).

Rolinson, G. N., Batchelor, F. R., Butterworth, D., Cameron-Wood, J., Cole, M., Eustance, G. C., Hart, M. V., Richards, M., and Chain, E. B. *Formation of 6-Aminopenicillanic Acid from Penicillin by Enzymation Hydrolysis*. Nature 187, pp. 236-237 (1960).

Shanmugam, K. T., Loo, A. S., and Valentine, R. C. *Deletion mutants of nitrogen fixation in Klebsiella pneumoniae: mapping of a cluster of nif genes essential for nitrogenase activity*. Biochim. Biophys. Acta 338, pp. 545-553 (1974).

Sobotkova, L., Grafkova, J., Stepanek, V., Vacik, T., Maresova, H., and Kyslik, P. *Indigenous plasmids in a production line of strains for penicillin G acylase derived from Escherichia coli W*. Folia Microbiol. (Praha) 44, pp. 263-266 (1999).

Streicher, S., Gurney, E., and Valentine, R. C. *Transduction of the nitrogen-fixation genes in Klebsiella pneumoniae*. Proc. Natl. Acad. Sci. U.S.A. 68, pp. 1174-1177 (1971).

Streicher, S. L., Shanmugam, K. T., Ausubel, F., Morandi, C., and Goldberg, R. B. *Regulation of nitrogen fixation in Klebsiella pneumoniae: evidence for a role of glutamine synthetase as a regulator of nitrogenase synthesis*. J. Bacteriol. 120, pp. 815-821 (1974).

Valle, F., Balbas, P., Merino, E., and Bolivar, F. *The role of penicillin amidases in nature and in industry*. Trends Biochem. Sci. 16, pp. 36-40 (1991).

Vecchionacce, R. A., Bassette, R., and Metha, R. S. *Survival of Escherichia coli, strain W, during the manufacture of cottage cheese*. J. Dairy Sci. 61, pp. 1704-1708 (1978).

Washington University School of Medicine *Klebsiella oxytoca M5a1* Website, Last Accessed May 15, 2007, Available from: genome.wustl.edu/genome.cgi?GENOME=Klebsiella %20oxytoca %20M5a1

Westenberg, D. J., Gunsalus, R. P., Ackrell, B. A., and Cecchini, G. *Electron transfer from menaquinol to fumarate. Fumarate reductase anchor polypeptide mutants of Escherichia coli*. J. Biol. Chem. 265, pp. 19560-19567 (1990).

Wu, Q. and Stewart, V. *NasFED proteins mediate assimilatory nitrate and nitrite transport in Klebsiella oxytoca (pneumoniae) M5a1*. J. Bacteriol. 180, pp. 1311-1322 (1998).

Wu, S. Q., Chai, W., Lin, J. T., and Stewart, V. *General nitrogen regulation of nitrate assimilation regulatory gene nasR expression in Klebsiella oxytoca M5a1*. J. Bacteriol. 181, pp. 7274-7284 (1999).

Yocum, R., *History of safe use and request for BL1 status for Klebsiella oxytoca M5a1*. (Aug. 3, 1989).

INCORPORATION BY REFERENCE

All patents, published patent applications and other references disclosed herein are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

SEQUENCE LISTING

<160> NUMBER OF SEQ ID NOS: 11

<210> SEQ ID NO 1

<211> LENGTH: 2333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

| | | | | | |
|---|---|---|---|---|---|
| cccttcggca | tggcaaaact | ggttggcggc | atttgcttct | ctctggggct | gattctttgt | 60 |
| gttgtctgcg | gagccgatct | ctttacttcc | acagtgttga | ttgttgttgc | taaggcgagt | 120 |
| gggcgcatca | cctggggtca | gttggcgaaa | aactggctaa | atgtctattt | tggcaacctg | 180 |
| gtcggcgcac | tgctgtttgt | acttttaatg | tggctttccg | gcgagtatat | gaccgcaaat | 240 |
| ggtcaatggg | gactaaacgt | cctacaaacc | gccgaccaca | aagtgcacca | tacttttatt | 300 |
| gaggccgtct | gccttggtat | cctggcaaac | ctgatggtat | gtctggcagt | atggatgagt | 360 |
| tattctggcc | gtagcctgat | ggacaaagcg | ttcattatgg | tgctgccggt | cgcgatgttt | 420 |
| gttgccagcg | gttttgagca | cagtatcgca | aacatgttta | tgatcccgat | gggtattgta | 480 |
| atccgcgact | tcgcatctcc | ggaattctgg | accgctgtcg | gttctgcacc | ggaaaatttt | 540 |
| tctcacctga | ccgtgatgaa | cttcatcact | gataacctga | ttccggttac | gatcggtaat | 600 |
| attatcggcg | gtggtttgtt | ggttgggttg | acatactggg | tcatttacct | gcgtgaaaac | 660 |
| gatcaccatt | aatggttgtc | gaagtacgca | gtaaataaaa | aatccactta | agaaggtagg | 720 |
| tgttacatgt | ccgagcttaa | tgaaaagtta | gccacagcct | gggaaggttt | taccaaaggt | 780 |
| gactggcaga | tgaagtaaa | cgtccgtgac | ttcattcaga | aaaactacac | tccgtacgag | 840 |
| ggtgacgagt | ccttcctggc | tggcgctact | gaagcgacca | ccaccctgtg | ggacaaagta | 900 |
| atggaaggcg | ttaaactgga | aaaccgcact | cacgcgccag | ttgactttga | caccgctgtt | 960 |
| gcttccacca | tcacctctca | cgacgctggc | tacatcaaca | aagcgttgga | aaaagttgtt | 1020 |
| ggtctacaga | ctgaagctcc | gctgaaacgt | gctcttatcc | cgttcggtgg | tatcaaaatg | 1080 |
| atcgagggtt | cctgcaaagc | gtacaaccgc | gaactggacc | cgatgatcaa | aaaaatcttc | 1140 |
| actgaatacc | gtaaaactca | caaccagggc | gtgttcgacg | tttacactcc | ggacatcctg | 1200 |
| cgttgccgta | atccggtgt | tctgaccggt | ctgccagatg | cttatggccg | tggccgtatc | 1260 |
| atcggtgact | accgtcgcgt | tgcgctgtac | ggtatcgact | acctgatgaa | agacaaatac | 1320 |
| gctcagttca | cctctctgca | ggctgatctg | gaaaacggcg | taaacctgga | acagactatc | 1380 |
| cgtctgcgcg | aagaaatcgc | tgaacagcac | cgcgctctgg | gtcagatgaa | agaaatggct | 1440 |
| gcgaaatacg | gctacgacat | ctctggtccg | gctaccaacg | ctcaggaagc | tatccagtgg | 1500 |
| acttacttcg | gctacctggc | tgctgttaag | tctcagaacg | gtgctgcaat | gtccttcggt | 1560 |
| cgtacctcca | ccttcctgga | tgtgtacatc | gaacgtgacc | tgaaagctgg | caagatcacc | 1620 |
| gaacaagaag | cgcaggaaat | ggttgaccac | ctggtcatga | aactgcgtat | ggttcgcttc | 1680 |
| ctgcgtactc | cggaatacga | tgaactgttc | tctggcgacc | cgatctgggc | aaccgaatct | 1740 |
| atcggtggta | tgggcctcga | cggtcgtacc | ctggttacca | aaaacagctt | ccgtttcctg | 1800 |
| aacaccctgt | acaccatggg | tccgtctccg | gaaccgaaca | tgaccattct | gtggtctgaa | 1860 |
| aaactgccgc | tgaacttcaa | gaattcgcc | gctaaagtgt | ccatcgacac | ctcttctctg | 1920 |
| caatatgaga | acgatgacct | gatgcgtccg | gacttcaaca | acgatgacta | cgctattgct | 1980 |
| tgctgcgtaa | gcccgatgat | cgttggtaaa | caaatgcagt | tcttcggtgc | gcgtgcaaac | 2040 |
| ctggcgaaaa | ccatgctgta | cgcaatcaac | ggcggcgttg | acgaaaaact | gaaaatgcag | 2100 |

-continued

```
gttggtccga agtctgaacc gatcaaaggc gatgtcctga actatgatga agtgatggag    2160
cgcatggatc acttcatgga ctggctggct aaacagtaca tcactgcact gaacatcatc    2220
cactacatgc acgacaagta cagctacgaa gcctctctga tggcgctgca cgaccgtgac    2280
gttatccgca ccatggcgtg tggtatcgct ggtctgtccg ttgctgctga ctc           2333
```

<210> SEQ ID NO 2
<211> LENGTH: 2018
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
agcgttcagc gacccgatga tcttcggtac tgatttgcgc cagtgatgcc tggctggctg     60
gaaagtggta cacaaaggtc ggttttctt tgccaatatt tggctctacg ccaaaggtaa    120
acagcaattg tagcagcgtg tcgcggtctt cttcggtatc agcaacattg ctcaaatcca    180
gtttcgctgc gacttcccgc agttgcgttt tgtcggcaga gagcgggtca atttccagat    240
aacgcaagaa agcttgttga taagaaaggc tttctgctgc cgggcagtcc agcacctgtt    300
gtaagagatc gtccacctcg ttcatcaacc ggtacatatc atagtgcggt cgataccact    360
ccagcatagt gaactcaggg ttgtgataac gccccatctc ttcattacgg aagctgcggc    420
acagctggaa taccggccca aaccggcaa ccagcaggcg tttcatatgg tattccgggc    480
tggtcattaa ccagagattc atccctgcg aatgcccggg ccaacgaaa cgtgtctcaa    540 acgggaccaa atgaatatcg gttaccgtcg cctggctcat acaaggcgtt tccacctcca    600
gcactccacg atcggcaaag aaacgacgga tctccgccat aatcgccgcg cgttttaata    660
agttaggaat ggatgcgctc ggctgccagg atgccgtttc gctcatagtt aaatctccag    720
tttttgacaa gggcacgaag tctactcgca acgcgacggc gagacaaatt ttacgcagga    780
atcaaacagc ggtgggcagt gactaaaaaa agcacgatct gatggtttag taattaaatt    840
aatcatcttc agtgataatt tagccctctt gcgcactaaa aaaatcgatc tcgtcaaatt    900
tcagacttat ccatcagact atactgttgt acctataaag gagcagtgga atagcgttcg    960
cagaccgtaa cttttcaggta cttaccctga agtacgtggc tgtgggataa aaacaatctg   1020
gaggaatgtc tctagataac gcatcgccaa tgtaaatccg gcccgccatt ggcgggccgt   1080
tttgtatgga aaccagaccc tatgttcaaa cgacgctct cgccttatt aattaccgcc    1140 tcttgctcca catttgctgc ccctcaacaa atcaacgata ttgtgcatcg cacaattacc   1200
ccgcttatag agcaacaaaa gatcccgggt atggcggtgg cggtaattta tcagggtaaa   1260
ccttattact ttacctgggg ctatgcggac atcgccaaaa agcagccgt cacacagcaa   1320 acgttgtttg agttaggttc ggtcagcaaa acatttactg gcgtgcttgg tggcgacgct   1380
attgctcgag gggaaatcaa gttaagcgat cccacaacaa atactggcc tgaacttacc    1440 gctaaacagt ggaatgggat cacactatta catctcgcaa cctacactgc tggcggcctg   1500
ccattgcagg tgccggatga ggtgaaatcc tcaagcgact tgctgcgctt ctatcaaaac   1560
tggcagcctg catgggctcc aggaacacaa cgtctgtatg ccaactccag tatcggtttg   1620
ttcggcgcac tggctgtgaa gccgtctggt ttgagttttg agcaggcgat gcaaactcgt   1680
gtctttcagc cactcaaact caaccatacg tggattaatg taccgcccgc agaagaaaag   1740
aattacgcct ggggatatcg cgaaggtaag gcagtgcatg tttcgcctgg ggcgttagat   1800
```

| | |
|---|---|
| gctgaagctt atggtgtgaa gtcgaccatt gaagatatgg cccgctgggt gcaaagcaat | 1860 |
| ttaaaacccc ttgatatcaa tgagaaaacg cttcaacaag ggatacaact ggcacaatct | 1920 |
| cgctactggc aaaccggcga tatgtatcag ggcctgggct gggaaatgct ggactggccg | 1980 |
| gtaaatcctg acagcatcat taacggcagt gacaataa | 2018 |

<210> SEQ ID NO 3
<211> LENGTH: 2158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

| | |
|---|---|
| gcgttgccct tacccgcttg ccctgggtc agcacactca gtcgtccgct gaccagagcg | 60 |
| ttctcgagcc ctgcctgcca gttgtcgact ttgacaccca gtcggccact caaaggaaaa | 120 |
| cctgcatacg gccagctcca gcgaccatcg cttacggtca attgttgacg agtaatttgc | 180 |
| cacggcaaat cgagcaacgg atcgccgtta tcccgtgcca gcacgatcaa ttgcccgcta | 240 |
| ttttcctgcc agtccagctc tgcatccacc agtgacggtt cctgcggcaa gtttaacgtc | 300 |
| gcagtagcat gcccacttac aggaagtcca tccggcacga gcggcatagt aaattccccc | 360 |
| accagtttaa ccggcggctg atttttcaaac gcgacgacat ccagttcgct gactgtaagt | 420 |
| tgttgccctt tcagctggcc ttgaaattta acttttttcgc cctgataacg cagttgctgg | 480 |
| atatcagagg ttaatgcgag agagagtttt ccctgccatt cctgccaggg agaaaaaatc | 540 |
| agtttatcga tattgatcca ggtgttaggc agcatggcct gccactgcgc gagtgttttt | 600 |
| ggagcggctg gcgattgctc cgtctgcggc aatttcgcca gacaagcaga atcaagttct | 660 |
| accgtgccga cgttcaataa ccagcggctg ggatgtgaaa ggctggcgtt ggtgatatgc | 720 |
| gcaagctgac aatctcccac cagataacga agatcgggaa tgattaaacc tttacgcgta | 780 |
| atgcgtgggc tttcatctaa tgcaatacgt gtcccgagcg gtagccagat gcccgccagc | 840 |
| gtgggaaccc acagcccgag cgtcatcagc agcgtcaacg gcacaagaat aatcagtaat | 900 |
| aacagcgcga gaacggcttt atatttaccc agcatgggta gttaatatcc tgatttagcg | 960 |
| aaaaattaag cattcaatac gggtattgtg gcatgtttaa ccgttcagtt gaaggttgcg | 1020 |
| cctacactaa gcatagttgt tgatgaattt ttcaatatcg ccatagcttt caattaaatt | 1080 |
| tgaaattttg taaatatttt ttagtagctt aaatgtgatt caacatcact ggagaaagtc | 1140 |
| tagataatct tgccgctccc ctgcattcca ggggagctga ttcagataat ccccaatgac | 1200 |
| ctttcatcct ctattcttaa aatagtcctg agtcagaaac tgtaattgag aaccacaatg | 1260 |
| aagaaagtag ccgcgtttgt tgcgctaagc ctgctgatgg cggatgtgt aagtaatgac | 1320 |
| aaaattgctg ttacgccaga acagctacag catcatcgct ttgtgctgga aagcgtaaac | 1380 |
| ggtaagcccg tgaccagcga taaaaatccg ccagaaatca gctttggtga aaaaatgatg | 1440 |
| atttccggca gcatgtgtaa ccgctttagc ggtgaaggca aactgtctaa tggtgaactg | 1500 |
| acagccaaag ggctggcaat gacccgtatg atgtgcgcta acccgcagct taatgaactc | 1560 |
| gataacacca ttagcgaaat gctgaaagaa ggtgcacaag tggatctgac cgcgaaccag | 1620 |
| ttaacgctgg cgaccgcgaa acagacatta acttataagc tggcggattt aatgaattaa | 1680 |
| tagctgccac agctcccggc ggcaagtgac tgttcactac agcgtttgcc gttgggtaat | 1740 |
| gcacacatcc caatcgccgt accatccagt tgacgggcaa cagaaagcga accgccgatc | 1800 |

| | |
|---|---|
| attgcacaat ttgcttctcc actactggac atcgacgctt ttaaacctgg cgctacgtgc | 1860 |
| gccgcagtcg cctgctgaac aggttcacta ctacacgccg acaacaataa agcggcacac | 1920 |
| cctacccaaa acgctgctcg catctttttct tcctctgatc ttcaagccaa acgacaccgc | 1980 |
| cataaataat aggcagcaca gagggcgacg tcgagagctg tcctgcgcgt tgccccgcat | 2040 |
| ttttactttt ttatggctat tttttttgccc tctgtttgat caaaacattc attacgctga | 2100 |
| tgtgggggac acaaaagcga aaatgcagaa gaaagccatt tgctaaaatt gaaagatt | 2158 |

<210> SEQ ID NO 4
<211> LENGTH: 2417
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

| | |
|---|---|
| aggaaatggc cgaaaccttt gaccgcgag tctatggttg ccgcattaac ctggaacatc | 60 |
| tgcgcggcat cctgcctgac ggtatttta agcgttatgg cgatgtggcc gaactgaagg | 120 |
| ccgaaaagat tgacgatgat tcggcgctga aaggcaaatg ggcgctgttt gcgaaaatca | 180 |
| ccccgaccga tgaccttatc gcgatgaaca aggccgcgca gaaggtctat acctcaatgg | 240 |
| aaattcagcc gaactttgcc aacaccggca atgttatct ggtggggctg gccgtcaccg | 300 |
| atgacccggc aagcctcggc acggaatacc tggaattctg ccgcacggca aacacaacc | 360 |
| ccctgaaccg cttcaaatta gccctgaaa acctgatttc agtggcaacg ccggttgagc | 420 |
| tggaatttga gacctgcct gaaaccgtgt tcacagccct gaccgaaaag gtgaaatcca | 480 |
| tttttggccg caaacaggcc agcgatgacg cccgtctgaa tgacgtgcat gaagcggtga | 540 |
| ccgctgtcgc tgagcatgtg caggaaaaac tgagcgccac tgagcagcgc cttgctgaga | 600 |
| tggaaaccgc cttttccgca cttaagcagg atgtgactga cagggcggat gaaaccagtc | 660 |
| aggcattcac ccgcctgaaa acagtctcg accacaccga aagtctgacc cagcagcgcc | 720 |
| gcagcaaagc caccggcggt ggcggtgacg ccctgatgac gaactgctga ccggcgtcag | 780 |
| tcagtccggg aaaaccttca cgattaaccc ttaatttcag gaaaaactta accgatgacg | 840 |
| agtcccgcac agcgcacatg atgcgggtct cggcagcgat gaccgcgcag cgggaagccg | 900 |
| ccccgctgcg acatgcaact gtctatgagc agatgctggt taagctcgcc gcagaccagc | 960 |
| gcacactgaa agcgatttat tcaaaagagc ttaaggccgc gaaaaaacgc gaactgctgc | 1020 |
| cgttctggtt gccgtgggtg aacggcgtgc tggagcaggg caaggtgca caggatgaca | 1080 |
| ttctgatgac ggtcatgctg tggcgtctgg ataccggcga tattgccggt gcgctggaga | 1140 |
| ttgcccgtta tgccctgaag tacgtctga ccatgccggg taaacaccgc gcacccccgc | 1200 |
| cgtacatgtt caccgaggag gtggcgcttg cggccatgcg cgcccacgct gccggtgagt | 1260 |
| ctgtggatac ccgcctgctg acggagaccc ttgcactgac cgccacggca gacatgcctg | 1320 |
| atgaagtgcg cgcaaagctg cacaaaatca ccggtctgtt tctgcgtgac gctggtgatg | 1380 |
| ccgccggtgc gctggctcac ctgcaacgtg cgacacagct cgactgtcag gcaggcgtca | 1440 |
| aaaagagat tgaacgactg gagcgggagc tgaaaccgaa gccggagccg cagcccaaag | 1500 |
| cggccacccg cgccctgcgt aagacccgga gcgtgacacc ggcaaaacgt ggacgcccga | 1560 |
| aaagaaagc cagttaacaa ccgaatgcgc cccgcgccag gcggcacgc cggtcagtga | 1620 |
| gggtgaatca cctgacgctg taccggcgtc caccgcccga cttttcagag gtagtcatga | 1680 |

-continued

```
tgacgctgat tattccgcga acggaggctc ccgtgtccgg tgagggtacg gtggtcatcc    1740
cgcaaccggc aggcgacgag ccggtgatta aaaacacgtt ctttttttccc gatatcgacc    1800 cgaagcgcgt ccgggaacgt atgcgccttg agcagaccgt cgcccccgcc cgtctgcgtg    1860
aggccatcaa gtcaggcatg gcggagacga atgcggagct gtacgagtac cgcgaacaga    1920
aaattgccgc cggttttacg cgtctggcgg acgttccggc ggacgacatc gacggtgaaa    1980
gcatcaaagt tttttactac gagcgcgccg tgtgtgcgat ggcgaccgcg tcgctttatg    2040
agcgttaccg cggcgtggat gccagtgcga aaggcgacaa aaggctgac agcattgaca     2100 gcaccattga tgagctgtgg cgggatatgc gctgggcggt ggcgcgtatc caggacaagc    2160
cgcgctgcat cgtgagtcaa atctgatgaa gacctttgcg ctacagggcg acacgctcga    2220
cgccatttgt gtccggtatt acgggcgcac tgagggcgtg gtcgaggccg tgctcgccgc    2280
aaatccggga ctggctgaac tgggtgcggt gctgccacac ggcaccgccg tcgaactgcc    2340
cgacgttcag accgcgcccg tggctgaaac tgtcaatctg tgggagtaac gcatgacagc    2400
agaagaaaaa agcgtcc                                                    2417
```

<210> SEQ ID NO 5
<211> LENGTH: 6667
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
gcagtgggag cacgcttagg cgtgtgactg cgtaccttt  gtataatggg tcagcgactt     60
atattctgta gcaaggttaa ccgaataggg gagccgaagg gaaaccgagt cttaactggg    120
cgttaagttg cagggtatag acccgaaacc cggtgatcta gccatgggca ggttgaaggt    180
tgggtaacac taactggagg accgaaccga ctaatgttga aaaattagcg gatgacttgt    240 ggctggggt  gaaaggccaa tcaaaccggg agatagctgg ttctccccga aagctattta    300
ggtagcgcct cgtgaaytca tctccggggg tagagcactg tttcggcaag ggggtcatcc    360
cgacttacca acccgatgca aactgcgaat accggagaat gttatcacgg agacacacg     420 gcgggtgcta acgtccgtcg tgaagaggga acaacccag accgccagct aaggtcccaa     480
agtcatggtt aagtgggaaa cgatgtggga aggcccagac agccaggatg ttggcttaga    540
agcagccatc atttaaagaa agcgtaatag ctcactggtc gagtcggcct gcgcggaaga    600
tgtaacgggg ctaaaccatg caccgaagct gcggcagcga cgcttatgcg ttgttgggta    660
ggggagcgtt ctgtaagcct gygaaggtgt rctgtgaggy atgctggagg tatcagaagt    720
gcgaatgcta acataagtaa cgataaagcg ggtgaaaagc ccgctcgccg aagaccaag     780 ggttcctgtc caacgttaat cggggcaggg tgagtcgacc cctaaggcga ggccgaaagg    840
cgtagtcgat gggaaacagg ttaatattcc tgtacttggt gttactgcga agggggacg     900 gagaaggcta tgttggccgg gcgacggttg tcccggttta agcgtgtagg ctggttttcc    960
aggcaaatcc ggaaaatcaa ggctgaggcg tgatgacgag ctcgagagga ggaaaaaaaa   1020
atgtcttaca ctgttggtac ctatctgcg  gaacgtctgg ttcaaatcgg tctgaaacat   1080
catttcgcgg tagctggcga ttataacctg gtcctgctgg acaatctgct gctgaataag   1140
aacatggaac aagtgtactg ttgcaatgag ctgaactgtg gcttctctgc tgagggctac   1200
gcgcgtgcga aaggcgccgc tgcggctgtt gttacctact ccgttggcgc actgtctgca   1260
```

```
ttcgatgcta ttggtggcgc ctatgccgag aacctgccgg tgatcctgat ctccggcgct    1320
ccaaacaaca acgatcacgc cgcaggccat gttctgcacc acgctctggg caagactgat    1380
taccactatc agctggagat ggctaagaac attaccgcag ctgccgaagc aatctacact    1440
cctgaagaag cgccggcaaa aatcgaccac gtaattaaga ccgccctgcg tgaaaagaaa    1500
ccggtgtatc tggagatcgc gtgtaacatc gcgtccatgc cgtgcgctgc gccgggtccg    1560
gcgtccgccc tgttcaacga cgaagcctct gacgaagcat ctctgaatgc ggcagtagag    1620
gaaactctga aattcatcgc taaccgcgat aaagttgccg tactggtggg ctctaagctg    1680
cgtgctgcgg cgctgaagaa ggcggcggtg aaattcgctg acgcactggg tggcgcagtc    1740
gctaccatgg cagcggcaaa atctttcttt ccggaggaaa acccgcacta tatcggtact    1800
agctggggcg aagtttctta tcctggcgta gagaaaacca tgaaggaagc ggatgccggta   1860
atcgcactgg cgccggtttt caacgactat agcaccaccg gctggaccga tatcccggac    1920
ccgaagaaac tggtactggc cgaaccgcgt tctgttgttg ttaacggcat ccgtttccca    1980
tctgttcatc tgaaagacta cctgactcgt ctggctcaga aggtatctaa gaaaactggt    2040
gcgctggact tctttaaatc cctgaatgca ggcgaactga gaaaagcggc cccagctgat    2100
ccgtctgcgc cactggtgaa cgcggagatc gctcgtcagg tggaggcgct gctgactccg    2160
aacaccactg tcatcgccga cgggcgac agctggttca acgctcagcg catgaagctg    2220
cctaacggtg ctcgtgtcga gtacgaaatg cagtggggtc atattggctg gtccgtaccg    2280
gcagccttcg gctacgctgt aggtgctccg gaacgtcgta acattctgat ggtaggtgat    2340
ggcagcttcc agctgactgc tcaggaggta gctcagatgg tacgtctgaa actgccggta    2400
attatcttcc tgatcaacaa ctaccggctac acgatcgagg tgatgatcca cgatggtccg    2460
tataacaaca ttaaaaactg ggactacgct ggtctgatgg aggtattcaa tggcaacggc    2520
ggttacgact ctggtgccgg caaaggcctg aaggctaaga ccggtggtga actggccgag    2580
gctatcaaag ttgcgctggc gaacactgat ggtccgaccc tgatcgagtg tttcatcggt    2640
cgtgaggact gcaccgaaga gctggttaaa tggggcaagc gtgtggcggc tgcgaactcc    2700
cgcaaaccgg ttaacaagct gctgtaaagg aggaaaaaaa aatgaaagcg ctgtgatca    2760
ccaaagacca cactattgaa gtaaaagata ccaaactgcg cccgctgaaa tatggcgagg    2820
ctctgctgga aatggaatac tgcggtgtgt gtcataccga tctgcacgtt aagaacggtg    2880
atttcggcga cgaaaccggc cgcatcactg gccacgaggg cattggcatt gtgaaacagg    2940
tcggtgaggt tgttaccttcc ctgaaggttg gtgaccgtgc gtctgttgct ggttcttca     3000
agggctgcgg tcattgtgaa tattgtgtct ctggcaacga aaccctgtgc cgtaacgtag    3060
aaaacgcggg ctacacggtg gatggcgcta tggccgaaga atgcatcgtc gtagcagact    3120
acagcgttaa ggtaccggac ggcctggacc ctgcggttgc atctagcatc acgtgcgcag    3180
gcgttaccac ctataaggct gtgaaagttt cccaaatcca gccaggccaa tggctggcta    3240
tctacggcct gggtggtctg ggcaacctgg cactgcaata tgctaaaaat gttttcaatg    3300
cgaaagtaat cgcaattgac gtgaacgatg agcaactggc tttcgcgaag gagctgggtg    3360
ctgacatggt aattaacccg aaaaacgagg atgctgcgaa atcattcag gaaaaagttg     3420
gcggtgctca cgcaacggtt gttacggctg ttgcgaaaag cgcctttaac agcgcggtag    3480
aagcgatccg tgcgggtggt cgcgttgttg ctgtcggtct gccgcctgag aagatggacc    3540
tgagcatccc tcgtctggtc ctggacgta ttgaggtact gggtagcctg gtaggcacgc     3600
gtgaggacct gaaagaagca ttccaatttg cagccgaagg taaagtaaaa ccgaaggtta    3660
```

```
ctaaacgcaa ggttgaagaa atcaaccaga ttttcgatga aatggaacac ggcaaattca    3720
ctggtcgtat ggtagttgat tttacgcatc attgaaggag gaaaaaaaaa tggcgtccag    3780
cactttctac atcccattcg taaacgagat gggtgagggc tccctggaaa aagctattaa    3840
agacctgaac ggctctggct tcaagaacgc gctgatcgta agcgacgcat tcatgaacaa    3900
gtccggtgtt gtgaaacaag tagcggatct gctgaaggcc cagggcatca actccgctgt    3960
atacgatggt gtaatgccga acccaaccgt gaccgccgta ctggagggcc tgaaaatcct    4020
gaaagacaac aactccgatt tcgtgatctc cctgggcggt ggttctccgc acgattgtgc    4080
caaggcaatc gcactggtag ctactaacgg cggtgaagtc aaagactacg agggcattga    4140
caagtctaag aaaccggcgc tgccgctgat gagcattaac accactgcgg gcactgcaag    4200
cgagatgacc cgtttctgca tcatcaccga cgaggtgcgc catgtaaaaa tggcaattgt    4260
ggaccgccac gtaactccaa tggtgtctgt gaacgatccg ctgctgatgg taggtatgcc    4320
gaaaggcctg actgctgcta cgggtatgga cgcactgact cacgcgtttg aggcctactc    4380
ctctaccgct gcgactccga ttactgatgc gtgcgcgctg aaagcggcgt ccatgattgc    4440
gaaaaacctg aaaaccgcgt gtgataacgg taaagacatg ccagcccgtg aggcgatggc    4500
ctatgcgcag ttcctggcgg gtatggcttt caacaatgcc agcctgggtt acgtacacgc    4560
tatggctcac caactgggtg gctactataa cctgccgcac ggtgtgtgca acgccgtgct    4620
gctgccgcat gttctggcat ataacgcgtc tgtcgtggcc ggtcgcctga aggatgttgg    4680
tgtagcaatg ggcctggaca tcgccaacct gggtgacaaa gagggcgctg aagcgacgat    4740
ccaggcggtg cgtgacctgg ccgcgtctat tggcattccg gcgaacctga ctgaactggg    4800
cgcgaaaaag gaggacgtac ctctgctggc agatcacgct ctgaaagacg catgcgctct    4860
gactaacccg cgccagggtg accagaaaga agttgaggaa ctgttcctga gcgcattcta    4920
atctagatca cacaggaaac catgaagggt gtgaaagaag taatgaaaat ctctctggaa    4980
atggactgta ccgtgaacgg tgacaaattc aaaatcactg gtgacggcac cggcgagccg    5040
tacgagggta cccagaccct gcatctgact gaaaaagagg gcaaaccgct gacctttttcc    5100 ttcgatgtac tgaccccggc attccaatat ggcaaccgca ctttcactaa gtatccgggc    5160
aacatcccgg acttcttcaa acagaccgtc tccggcggtg gctatacttg ggaacgtaaa    5220
atgacttacg aggacggcgg catctctaac gttcgttccg atatcagcgt aaaaggtgac    5280
agcttctact ataaaatcca ctttaccggt gagtttccac cgcacggccc ggtcatgcag    5340
cgcaagactg tcaagtggga gccgtccact gaagttatgt atgtggatga caaatctgat    5400
ggcgtactga aggcgacgt taacatggcg ctgctgctga agatggccg ccacctgcgc    5460 gttgacttca acacctctta cattccgaag aagaaagtag agaacatgcc ggactaccat    5520
ttcattgatc accgtatcga gatcctgggt aaccctgaag ataagccggt gaaactgtac    5580
gaatgcgcgt ggcccgcta ttctctgctg ccggaaaaga caaataatc tagaaaaagc    5640 cagattatta atccggcttt tagatctagc aacaaatgcc ctgcttccag gaaaagcctc    5700
taagcatcag gtaacatcaa atcgtacccc aaaccgacac aggtggtcag gtagagaata    5760
ccaaggcgct tgagagaact cgggtgaagg aactaggcaa aatggtgccg taacttcggg    5820
agaaggcacg ctgatatgta ggtgaggtcc ctcgcggatg gagctgaaat cagtcgaaga    5880
taccagctgg ctgcaactgt ttattaaaaa cacagcactg tgcaaacacg aaagtggacg    5940
tatacggtgt gacgcctgcc cggtgccgga aggttaattg atggggttag cgcaagcgaa    6000
```

| | |
|---|---:|
| gctcttgatc gaagccccgg taaacggcgg ccgtaactat aacggtccta aggtagcgaa | 6060 |
| attccttgtc gggtaagttc cgacctgcac gaatggcgta atgatggcca ggctgtctcc | 6120 |
| acccgagact cagtgaaatt gaactcgctg tgaagatgca gtgtacccgc ggcaagacgg | 6180 |
| aaagaccccg tgaacctta ctatagcttg acactgaaca ttgagccttg atgtgtagga | 6240 |
| taggtgggag gctttgaagt gtggacgcca gtctgcatgg agccgacctt gaaataccac | 6300 |
| cctttaatgt ttgatgttct aacgttgacc cgtaatccgg gttgcggaca gtgtctggtg | 6360 |
| ggtagtttga ctggggcggt ctcctcctaa agagtaacgg aggagcacga aggttggcta | 6420 |
| atcctggtcg gacatcagga ggttagtgca atggcataag ccagcttgac tgcgagcgtg | 6480 |
| acggcgcgag caggtgcgaa agcaggtcat agtgatccgg tggttctgaa tggaagggcc | 6540 |
| atcgctcaac ggataaaagg tactccgggg ataacaggct gataccgccc aagagttcat | 6600 |
| atcgacggcg gtgtttggca cctcgatgtc ggctcatcac atcctggggc tgaagtaggt | 6660 |
| cccaagg | 6667 |

```
<210> SEQ ID NO 6
<211> LENGTH: 5333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
```

| | |
|---|---:|
| cgcccagaac gccattatgc atgacggcaa agcctcagaa ggcgatattc agggccacgt | 60 |
| tgatggctgg atcaaagccc accagcagca gttcgatggc tgggtgaatg aggcgctggc | 120 |
| agcgcagaag taactcgagc tactactatc tagaggactc tatgcacggc accgtgttag | 180 |
| cacagaataa aaaaggctgg caggccacgc tggacctcca gtttcaattt ctcggcggga | 240 |
| aaaccacgct cgcctcccgt cgccatgtcg gtccctcac cgttcagcgc ccgttttatc | 300 |
| ccgaagcaga gacctgccac ctctatctgc ttcatccgcc cggcggcatc gtcggcggcg | 360 |
| atgagctcac cattagcgcg accattgatg ccgattgcca taccctgatc accatgcccg | 420 |
| gcgccagcaa gttttatcgc agcagcggcg cgcaggcgcg gcttcagcaa accctgacgc | 480 |
| tggccgaaaa ctcgacgctc gagtggctgc cgcaggacgc gatcttcttt cccggcgcca | 540 |
| acgccgcttt gtctaccgcc tttcatctcg ccgcctccag cacgctgctg gcctgggacc | 600 |
| tgctgtgcct tggccgaccg gttatcggcg aagcttttag ccacggcgcg ctcgccaatc | 660 |
| ggctggaagt gtgggtcgac ggctctccgc tgctgattga gcgcctgagc ctggccgatg | 720 |
| gacagctggc ctgcgtcgca cagcagccgt gggtgggaac gatgctgttc tacccggcga | 780 |
| acgaaacgct gctggaaggc gtacgcgaaa agcttacgcc gctggcaaat tacgccggcg | 840 |
| ctacgctcac cgacggcctg ctaacggtac gttttttaag cgatgataat ctgctttgcc | 900 |
| agcgggcgat gcgcgatatc tggcaattca tgcgccgca tctgaccggc aaatctccgg | 960 |
| tacttccccg aatctggctg acttaagaga acgctatgga actgacaccc agagaaaaag | 1020 |
| acaagctgtt gctgtttacc gccgcactgg tggcggagcg tcgcctggcc gcggcctga | 1080 |
| agctcaacta tcccgaatcc gtggccctga ttagcgcctt tattatggaa ggcgcgcgcg | 1140 |
| atggcaaaag cgtcgccgag ctgatggaag agggacgcca cgtcctgagc cgtgaccagg | 1200 |
| tcatggaagt cgtgccggaa atgatcccg atatccaggt cgaagccacc ttcccggacg | 1260 |
| gctcgaagct ggtcaccgtt cataatccga taatctgagg tagcgtgatg atccctggag | 1320 |

```
aatatcagat aaagcccgga cagatagccc tcaacgctgg ccgcgcaacc tgcagcatta   1380
ttgttgaaaa tcacggcgac cggccgattc aggtcggctc gcattaccac ttcgccgagg   1440
tcaacccggc gctgaagttc gatcgccagc aggcgaccgg ctatcggctg aatatcgctg   1500
ccggcaccgc agtgcgcttc gagccgggtc aaaaacgcga ggtggagctg gtggcgctgg   1560
ccggaacccg tgcggtgtac ggttttcgcg gcgaggtgat gggcgcgctg gaggcaaacg   1620
atgagtgaaa tttcacgtca ggcctatgcc gacatgttcg ccctaccac cggcgataaa   1680 gttcgcctgg cggacaccga gctatggatc gaggtcgaag atgatttgac cacctacggc   1740
gaagaggtca aatttggcgg cggtaaagtg atccgcgacg gaatggggca gggacagatg   1800 cttccgccg ggtgcgtgga tctggtgctg accaacgccc tgatcgtcga ttactggggg   1860
atcgtcaaag ccgatattgg cgtcaaagac ggacggatct tcgcgatcgg caaagccggc   1920
aatccggata ttcagcccaa cgtcacgatc ccgatcggcg cggccacgga aattattgcg   1980
gcggaaggta agatcgtcac cgccggcggc gtcgatacgc atattcactg gatctgcccg   2040
cagcaggcgg aagaggcgct ggtctccggc gtcaccacca tgatcggcgg cgggaccggc   2100
ccggcggcgg gcaccaacgc cacgacctgt acgccagggc cgtggtatat ctcgcggatg   2160
ctgcaggccc ccgacagcct gccggtcaat atcggcctac tgggtaaagg caacggctcg   2220
aatcccgacg cgctgcgtga gcaggtcgcg gccggggtta tcggcctgaa aattcacgaa   2280
gactggggcg cgaccccggc ggcaatcgac tgcgcgctga ccgtggccga cgaaatggac   2340
gtgcaggtcg cgctgcacag cgacaccctc aatgagtccg gattcgttga ggataccctg   2400
gcggccatcg gcgggcgcac tatccatact ttccataccg aaggcgcggg cggcggccat   2460
gcgccggata ttattaccgc ctgcgcgcac cccaatattt taccgtcgtc gaccaacccg   2520
acgctgccct ataccgtcaa caccattgac gaacatctgg atatgctgat ggtttgccat   2580
cacctcgatc cggatatcgc cgaggacgtg gcgtttgccg aatcgcgcat tcggcgggaa   2640
accatcgccg cggaagacgt cctacacgac ctcggcgcct tctcccttac ctcgtcagat   2700
tcgcaggcga tggggcgcgt cggcgaagtg gtgttacgta cctggcaggt agcgcaccgg   2760
atgaaagttc agcgcggccc gctggcggaa gagagcggcg ataacgacaa cttccgcgta   2820
aagcgctata tcgccaaata cacgattaat ccggcgttga cccacggtat cgcccacgaa   2880
gtcggctcga ttgaagccgg taaactggcg gatctggtgc tgtggtcccc ggcgttcttc   2940
ggcgtgaaac cggcgacaat cgttaaaggc ggcatgatcg ccatggcgcc gatgggcgac   3000
atcaacgcct ctatcccaac gccgcagccg gtgcactatc gcccgatgtt cggcgcgctg   3060
ggcagcgccc gtcaccgctg ccgtttgacc ttcctgtcgc aggcggcggc ggaaaacggc   3120
gtcgctgaac ggctgaacct gcacagcgcg acggcggtgg tgaaaggctg ccgcgaggta   3180
caaaaagctg atatgcacca caacggcctg ctgcccaata ttaccgtgaa ttcgcaaacc   3240
tacgaggtgc gcatcgacgg cgaactgatt accagcgaac cggcggacgt gctaccgatg   3300
gcgcaacgtt atttcctgtt ttaaggagcg cacatgcttt atttaaccca acgggtggag   3360
accccggcgc aggccacggc cagcgttacc ctgccgattg acgtgcgggt aaaaagccgc   3420
ataaaagtca cgcttaacga tggtcgtcag gcgggcctgc tgctgccgcg cggcctgctg   3480
ctgcgcggcg gcgatattct cagcaacgaa aacggcagcg agttcatcga agtgatcgcc   3540
gccgatgaag ccgtttcggt cgtacgctgc gatgacccct ttgtgctggc gaaggcctgc   3600
tatcaccttg gcaatcgcca cgtgccgctg caaattatgc ccggcgagct gcgctatcat   3660
cacgatcacg tcctggacga tatgctgcgc cagtttggtc tggccgtgga tttcgcgcat   3720
```

```
ctgccgtttg aaccggaagc cggcgcctac gccagcgaat cacacggcca tcaccatcat   3780
caccatcatg agcacagcca ctaaatgccg acgccggaaa aacgtctgcg cttaatgcag   3840
cttgccagca gcagcctccc ggttggcggc tacagctggt cccaggggct ggagtgggcg   3900
gtggaagcgg gctgggtagc ggataccgcc gcttttgagc gctggcagct gcggcagatg   3960
gagcagagct tttttaccgt cgatctgccg ctgttcgccc ggctttaccg ggcctgcgaa   4020
gcgggcgatc tggcctgcgc ccggcgctgg accgcttacc tgctcgcctg ccgggaaacc   4080
cgcgagctgc gcgatgaaga gcgcaaccgc ggcgcggcct tcacccggct gctggccgac   4140
tggcagccga actgcccgcc cgagtggcgc aagctgtgcc agcaaagtca gctaaccggc   4200
atggcgtggc tcggcgtacg ctggcaaatc gccattcctg acctagccct gagccttggc   4260
tatagctgga ttgaaagcgc ggtgatggcg ggcgtcaagc tggtgccctt tggccagcag   4320
gcggcccagc agttgattct acgcctgtgc gaccgctacg cggcggacat ggacagcgcc   4380
ctcgccgccc ggacgacgc cctcggttcg gcgacgccgc tggcggctat cgcttccgcc   4440
cggcacgaaa cccagtattc ccgattattc cgttcttagg agaaggtatg aacatgatta   4500
agcaaccgct gcgcgtcggc gtcggcggcc cggtcggctc cggaaaaacg cgctgctgg    4560 aagccctctg caaagccatg cgcgacacct ggcagctggc ggtggtgacc aacgatatct   4620
acaccaaaga agatcagcgc attctcaccg aagccggtgc cctggagcct gaacgaattg   4680
tcggtgtcga accggcggc tgcccgcata ccgccattcg ggaagacgcg tcaatgaacc    4740
ttgccgcggt ggaagcgctg agcgagaaat tcggcaatct cgatctcatc tttgtggaaa   4800
gcggcggcga taatctgagc gccaccttca gcccggagct ggcggatctc accatctacg   4860
tcatcgacgt ggcggaaggg gaaaaaatcc cgcgcaaagg cggaccgggg atcaccaaat   4920
ccgacttcct ggtgatcaat aaaaccgatc ttgcaccgta cgtgggcgcg tctctggaag   4980
tgatggagcg cgatacctg cgcatgcgcg gcgaacgccc gtggagcttc accaacttga    5040
aaagcggcga cggcctgcaa aatatcatcg cctttatcga agacaaaggc atgctcggca   5100
agtaacccct gcaccatccc ggcgcagagg tgtcggatg tgcatgccc tgccctctct     5160 ttagccatcc ccggatcctt tttattcagg cggataaggc gttttttgcct catccgccgc   5220 tctgtacaca atgcctgatg cgacgctgac gcgtcttatc atgcctacaa aatacactca   5280
ttccgtatgg cggataaggc gttttcgccg catccgccgt tctgtgcaca atg           5333
```

<210> SEQ ID NO 7  
<211> LENGTH: 536  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 7

```
gatgacagta cgctgctttc gggtgttttcc gagctggatg ctattccacc gcagtctcag    60
gtgctcacag aacaacggct gaagtattgg tttaaactgg ctgacccaca aacgcgaaat    120
actttcctgc agtgggcgga aaacaaccat tcttcctgag attttgtgc ctgtgcgcag     180 gcttttcgg tctttatctt gcagcgataa gtgcttacag taatctgtag gaaagttaac     240
tacggatgta catttattgc acaggtggca aacgccacct gtttcttacg gtttctcgc     300 caccggcaca tccagatttt tcagtatttc cacaaaggga gagggattct ctttgttaaa    360
cagtgcccat acccgatggc gtgcccgggt cagcgccacg tacattaacc gccgttcttc    420
```

```
agcgtccggg aaatcctcaa ccggtggcag tagcgcctct tccataatcg actcccgcgc    480
cgcagccgga aaaccatcac ttccctcctg caagccaacg atgatgacgt aatccg        536

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cagcagcgaa actgtttgcc a                                               21

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtgcgatgtg gtttgtaggc atgat                                           25

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgatggcaga tgacagtacg ctg                                             23

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggcaacaggc ggattacgtc a                                               21
```

What is claimed is:

1. A recombinant *Escherichia coli* bacterium comprising a *Klebsiella oxytoca* urease operon comprising ureD, A, B, C, E, F and G genes, wherein the chromosome of the recombinant *Escherichia coli* bacterium has a deletion of a methylglyoxal synthase A (mgsA) gene, wherein the nucleotide sequence resulting from the deletion of the mgsA gene on the chromosome of the recombinant *Escherichia coli* bacterium is SEQ ID NO: 7, and wherein the recombinant *Escherichia coli* bacterium is ethanologenic and uptakes and metabolizes xylose, arabinose and glucose into ethanol and organic acids during fermentation.

2. The recombinant bacterium of claim 1, further comprising ethanol production genes.

3. The recombinant bacterium of claim 2 wherein the ethanol production genes comprise a pyruvate decarboxylase (pdc) gene.

4. The recombinant bacterium of claim 2, wherein the ethanol production genes comprise a pyruvate decarboxylase (pdc) gene, an alcohol dehydrogenase A (adhA) gene and/or an alcohol dehydrogenase B (adhB) gene.

5. The recombinant bacterium of claim 4, wherein the pdc, adhA and adhB genes are derived from *Zymomonas mobilis*.

6. The recombinant bacterium of claim 1, wherein one or more genes in a fumarate reductase (frd) operon is deleted in the recombinant *Escherichia coli* bacterium.

7. The recombinant bacterium of claim 6, wherein the frd operon comprises frdA, B, C and D genes.

8. The recombinant bacterium of claim 6, wherein the frd operon comprises frdA, B, C and D genes, wherein the frdA, B, C and D genes are deleted, and wherein deletion of the frdA, B, C and D genes results in a sequence as set forth in SEQ ID NO:2.

9. The recombinant bacterium of claim 1, wherein a lactate dehydrogenase A (ldhA) gene is deleted in the recombinant *Escherichia coli* bacterium.

10. A kit comprising the recombinant bacterium of claim 1 and instructions for use.

11. *Escherichia coli* strain SD7 having Deposit Accession No. NRRL B-50394.

12. A method of producing ethanol comprising culturing the recombinant bacteria of claim 1 under conditions suitable for the production of ethanol.

* * * * *